US011857641B2

(12) United States Patent
Ando et al.

(10) Patent No.: US 11,857,641 B2
(45) Date of Patent: *Jan. 2, 2024

(54) METHOD FOR THE TREATMENT OF MUCOPOLYSACCHARIDOSIS TYPE I

(71) Applicants: Sangamo Therapeutics, Inc., Richmond, CA (US); Roselia C. Santana, Walnut Creek, CA (US)

(72) Inventors: Dale Ando, Richmond, CA (US); Cheryl Wong Po Foo, Richmond, CA (US); Sagar A. Vaidya, Richmond, CA (US); Shelley Q. Wang, Richmond, CA (US)

(73) Assignee: Sangamo Therapeutics, Inc., Brisbane, CA (US)

(*) Notice: Subject to any disclaimer, the term of this patent is extended or adjusted under 35 U.S.C. 154(b) by 675 days.

This patent is subject to a terminal disclaimer.

(21) Appl. No.: 16/534,302

(22) Filed: Aug. 7, 2019

(65) Prior Publication Data

US 2020/0246486 A1 Aug. 6, 2020

Related U.S. Application Data

(60) Provisional application No. 62/802,568, filed on Feb. 7, 2019, provisional application No. 62/802,110, filed on Feb. 6, 2019.

(51) Int. Cl.

| *A61K 48/00* | (2006.01) |
| *A61P 3/00* | (2006.01) |
| *G01N 33/66* | (2006.01) |
| *C12Q 1/34* | (2006.01) |
| *A61K 38/47* | (2006.01) |

(52) U.S. Cl.
CPC ........... *A61K 48/005* (2013.01); *A61K 38/47* (2013.01); *A61P 3/00* (2018.01); *C12Q 1/34* (2013.01); *C12Y 301/06013* (2013.01); *C12Y 302/01076* (2013.01); *G01N 33/66* (2013.01)

(58) Field of Classification Search
CPC ...... C12N 9/22; C12N 15/11; C12N 2800/80; C12N 15/902; C12N 15/62; C12N 15/63; C12N 15/52; C12N 2740/16043; C12N 15/111; C12N 15/86; C12N 15/907; C12N 15/8201; A61K 48/005; A61K 48/00
See application file for complete search history.

(56) References Cited

U.S. PATENT DOCUMENTS

| 4,120,649 A | 10/1978 | Schechter |
| 4,665,077 A | 5/1987 | Stringfellow et al. |
| 5,114,721 A | 5/1992 | Cohen et al. |
| 5,420,032 A | 5/1995 | Marshall et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,379,903 B1 | 4/2002 | Brizzart et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |

(Continued)

FOREIGN PATENT DOCUMENTS

| GB | 2 338 237 A | 12/1999 |
| JP | 7275152 B2 | 5/2023 |

(Continued)

OTHER PUBLICATIONS

Dickson et al., Safety of laronidase delivered into the spinal canal for treatment of cervical stenosis in mucopolysaccharidosis I, Molecular Genetics and Metabolism, vol. 116, pp. 69-74. (Year: 2015).*
Anguela, et al., "ZFN Mediated Targeting of Albumin "Safe Harbor" Results in Therapeutic Levels of Human Factor VIII in a Mouse Model of Hemophilia A," Blood 122(21):720 (2013).
Azadeh et al., "A Rapid Two-Step Iduronate-2-Sulfatatse Enzymatic Activity Assay for MPSII Pharmacokinetic Assessment," Journal of Inherited Metabolic Disease, 2017, vol. 38, (pp. 89-95).
Burrow et al., "Review of the use of idursulfase in the treatment of mucopolysaccharidosis II," Biologics: Targets & Therapy, 2008, vol. 2, No. 2 (pp. 311-320).
Burton and Giugliani, "Diagnosing Hunter syndrome in pediatric practice: practical considerations and common pitfalls," European Journal of Pediatrics, 2012, vol. 171 (pp. 631-639).

(Continued)

*Primary Examiner* — Dana H Shin
(74) *Attorney, Agent, or Firm* — Foley & Lardner LLP

(57) ABSTRACT

Described herein are methods and compositions for treating MPS I (Hurler/Hurler-Scheie/Scheie Syndrome) by administering to the subject a composition comprising a iduronidase (IDUA) polynucleotide. In one aspect, provided is a method of reducing, delaying and/or eliminating one or more of the need for additional treatment procedures, the onset, progression and/or severity of symptoms in a subject with MPS I, by administering to the subject a composition comprising a iduronidase (IDUA) polynucleotide.

31 Claims, 4 Drawing Sheets

Specification includes a Sequence Listing.

(56) References Cited

U.S. PATENT DOCUMENTS

| | | |
|---|---|---|
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,419,829 B2 | 9/2008 | Mitrophanous et al. |
| 7,888,121 B2 | 2/2011 | Urnov et al. |
| 7,914,796 B2 | 3/2011 | Miller et al. |
| 8,034,598 B2 | 10/2011 | Miller |
| 8,409,861 B2 | 4/2013 | Guschin et al. |
| 8,563,314 B2 | 10/2013 | Gregory et al. |
| 8,568,526 B2 | 11/2013 | Gregory et al. |
| 8,623,618 B2 | 1/2014 | Doyon et al. |
| 8,697,359 B1 | 4/2014 | Zhang |
| 8,703,489 B2 | 4/2014 | Wang |
| 8,772,453 B2 | 7/2014 | Paschon et al. |
| 8,823,618 B2 | 9/2014 | Lee et al. |
| 8,932,814 B2 | 1/2015 | Cong et al. |
| 9,005,973 B2 | 4/2015 | Cost et al. |
| 9,200,266 B2 | 12/2015 | Wang |
| 9,458,205 B2 | 10/2016 | Gregory et al. |
| 10,081,661 B2 | 9/2018 | Miller et al. |
| 10,968,261 B2 | 4/2021 | Miller et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0129357 A1* | 6/2006 | Francis .......... G16H 20/10 702/188 |
| 2006/0188987 A1 | 8/2006 | Guschin et al. |
| 2007/0117128 A1 | 5/2007 | Smith et al. |
| 2007/0218528 A1 | 9/2007 | Miller |
| 2009/0068164 A1 | 3/2009 | Segal et al. |
| 2011/0301073 A1 | 12/2011 | Gregory et al. |
| 2013/0189718 A1 | 7/2013 | Ruiz et al. |
| 2014/0017212 A1 | 1/2014 | Rebar |
| 2014/0335063 A1 | 11/2014 | Cannon et al. |
| 2015/0056705 A1 | 2/2015 | Conway et al. |
| 2015/0159172 A1 | 6/2015 | Miller et al. |
| 2015/0166615 A1 | 6/2015 | Xia et al. |
| 2016/0060656 A1 | 3/2016 | Rebar |
| 2016/0326548 A1 | 11/2016 | Cost |
| 2016/0375110 A1* | 12/2016 | High .......... A61K 38/4846 514/44 R |
| 2017/0016027 A1 | 1/2017 | Lee et al. |
| 2017/0119906 A1 | 5/2017 | Riley |
| 2017/0189375 A1* | 7/2017 | Masson .......... A61K 9/2054 |
| 2017/0216456 A1 | 8/2017 | Alexander et al. |
| 2018/0087072 A1 | 3/2018 | Miller et al. |
| 2018/0185495 A1 | 7/2018 | Heller et al. |
| 2018/0303914 A1* | 10/2018 | Lee .......... A61K 38/465 |
| 2019/0038772 A1* | 2/2019 | Hinderer .......... C12N 9/2402 |
| 2019/0078119 A1* | 3/2019 | Wilson .......... C12N 15/86 |
| 2019/0241877 A1 | 8/2019 | DeKelver et al. |
| 2020/0063160 A1 | 2/2020 | Ando et al. |
| 2020/0071743 A1 | 3/2020 | Cao et al. |

FOREIGN PATENT DOCUMENTS

| | | |
|---|---|---|
| WO | WO 1990/008187 A1 | 7/1990 |
| WO | WO 1990/011294 A1 | 10/1990 |
| WO | WO 1991/001133 A1 | 2/1991 |
| WO | WO 1995/019431 A1 | 7/1995 |
| WO | WO 1996/006166 A1 | 2/1996 |
| WO | WO 1998/037186 A1 | 8/1998 |
| WO | WO 1998/053057 A1 | 11/1998 |
| WO | WO 1998/053058 A1 | 11/1998 |
| WO | WO 1998/053059 A1 | 11/1998 |
| WO | WO 1998/053060 A1 | 11/1998 |
| WO | WO 1998/054311 A1 | 12/1998 |
| WO | WO 2000/027878 A1 | 5/2000 |
| WO | WO 2001/060970 A2 | 8/2001 |
| WO | WO 2001/088197 A2 | 11/2001 |
| WO | WO-02/07752 | 1/2002 |
| WO | WO 2002/016536 A1 | 2/2002 |
| WO | WO 2002/077227 A2 | 10/2002 |
| WO | WO 2002/099084 A2 | 12/2002 |
| WO | WO 2003/016496 A2 | 2/2003 |
| WO | WO 2007/014275 A2 | 2/2007 |
| WO | WO 2010/079430 A1 | 7/2010 |
| WO | WO-2012/177020 A9 | 12/2012 |
| WO | 2014/097113 A2 | 6/2014 |
| WO | WO-2016/100603 A1 | 6/2016 |
| WO | 2017/123757 A1 | 7/2017 |
| WO | WO-2019/118875 | 6/2019 |

OTHER PUBLICATIONS

Cardone et al., "Correction of Hunter syndrome in the MPSII mouse model by AAV2/8-mediated gene delivery," Human Molecular Genetics 15(7):1225-1236 (2006).

Chistiakov at al., "Genetic analysis of 17 children with Hunter syndrome: identification and functional characterization of four novel mutations in the iduronate-2-sulfatase gene," Journal of Genetics and Genomics, Apr. 20, 2014, vol. 41, No. 4 (pp. 197-203).

Choi et al., "Optimization of AAV expression cassettes to improve packaging capacity and transgene expression in neurons", Molecular Brain, 2014, vol. 7, Issue No. 17, pp. 1-10.

De Camargo Pinto et al., "Are MPS II heterozygotes actually asymptomatic? A study based on clinical and biochemical data, X-inactivation analysis and imaging evaluations," American Journal of Medical Genetics, Dec. 28, 2010, vol. 155, No. 1 (pp. 50-57).

Donello et al., "Woodchuck Hepatitis Virus Contains a Tripartite Posttranscriptional Regulatory Element," Journal of Virology, Jun. 1998, vol. 72, No. 6 (pp. 5085-5092).

Eliahu et al., "The Correction of Hunter Fibroblasts by Exogenous Iduronate Sulfate Sulfatase: Biochemical and Ultrastructural Studies," American Journal of Human Genetics, 1981, vol. 33 (pp. 576-583).

Flajolet et al., "Woodchuck Hepatitis Virus Enhancer I and Enhancer II Are Both Involved in N-myc2 Activation in Woodchuck Liver Tumors," Journal of Virology, Jul. 1998, vol. 72, No. 7 (pp. 6175-6180).

Garcia et al., "Preclinical dose ranging studies for enzyme replacement therapy with idursulfase in a knock-out mouse model of MPS II," Molecular Genetics and Metabolism 91(2):183-190 (2007).

GenBank NM_000202.7 Homo sapiens iduronate 2-sulfatase (IDS), transcript variant 1, mRNA(2018).

Guffon et al., Bone Marrow Transplantation in Children with Hunter Syndrome: Outcome after 7 to 17 Years, the Journal of Pediatrics, May 1, 2009, vol. 154, No. 5 (pp. 733-737).

Hohne et al., "Malignant transformation of immortalized transgenic hepatocytes after transfection with hepatitis B virus DNA," The EMBO Journal, 1990, vol. 9, No. 4 (pp. 1137-1145).

Jinek et al., "A Programmable Dual-RNA-Guided DNA Endonuclease in Adaptive Bacterial Immunity," Science, Aug. 17, 2012, vol. 337 (7 pages).

Kim et al., "Comparative study of idursulfase beta and idursulfase in vitro and in vivo," Journal of Human Genetics, Official journal of the Japan Society of Human Genetics, 2017, vol. 62 (pp. 167-174).

Kim et al., "Correlation between urinary GAG and anti-idursulfase ERT neutralizing antibodies during treatment with NICIT immune tolerance regimen: A case report," Molecular Genetics and Metabolism, Sep. 2017, vol. 122, Nos. 1-2 (pp. 92-99).

Lampe, et al., "Long-term experience with enzyme replacement therapy (ERT) in MPS II patients with a severe phenotype: an international case series," J. Inherit Metab Dis 37(5):823-9 (2014).

Laoharawee, et al., "Dose-Dependent Prevention of Metabolic and Neurologi Cisease in Murine MPS II by ZFN-Mediated in Vivo Genome Editing," Molecular Therapy 26(4):1127-1136 (2018).

Laoharawee, et al., "In Vivo Zinc-Finger Nuclease Mediated Iduronate-2-Sulfatase (IDS) Target Gene Insertion and Correction of Metabolic Disease in a Mouse Model of Mucopolysaccharidosis Type II (MPS II)," Molecular Therapy 24:S192 (2016).

(56) References Cited

OTHER PUBLICATIONS

Lee et al., "Direct assay of iduronate-2-sulfatase for Hunter disease using UPLC-tandem mass spectrometry and fluorogenic substrate," Clinical Biochemistry, Dec. 2015, vol. 48, No. 18 (pp. 1350-1353).
Lin et al., "Detection of Hunter syndrome (mucopolysaccharidosis type II) in Taiwanese: Biochemical and linkage studies of the iduronate-2-sulfatase gene defects in MPS II patients and carriers," Clinica Chimica Acta; International Journal of Clinical Chemistry, Aug. 2006, vol. 369, No. 1 (pp. 29-34).
Loeb et al., "Enhanced expression of transgenes from adeno-associated virus vectors with the woodchuck hepatitis virus post-transcriptional regulatory element: implications for gene therapy," Human Gene Therapy, Sep. 20, 1999, vol. 10, No. 14 (dated 2295-2305).
Newfoundland Labrador, "Standardized Adult (40-130 kg) IVIG Infusion Rate Tables 3.0," pp. 13-18, https://www.gov.nl.ca/hcs/files/bloodservices-resources-pdf-adult-invig-inf-table.pdf (2018).
Non-Final Office Action on U.S. Appl. No. 16/534,280 dated May 10, 2022.
Pardridge, W., "The Blood-Brain Barrier: Bottleneck in Brain Drug Development," NeuroRx: The Journal of the American Society for Experimental NeuroTherapeutics, Jan. 2005, vol. 2, No. 1 (pp. 3-14).
Parini et al., "Enzymatic replacement therapy for Hunter disease: Up to 9 years experience with 17 patients," Molecular Genetics and Metabolism Reports, 2015, vol. 3 (pp. 65-74).
Quaio et al., "Report of a Large Brazilian Family With a Very Attenuated Form of Hunter Syndrome (MPS II)," Journal of Inherited Metabolic Disease (JIMD), Published online: Nov. 8, 2011 (4 pages).
Raluy-Callado et al., "The impact of Hunter syndrome (mucopolysaccharidosis type II) on health-related quality of life," Orphanet Journal of Rare Diseases, 2013, vol. 8, No. 101 (pp. 1-10).
Sasaki et al., "Hunter's Syndrome: A Study in Airway Obstruction," Laryngoscope, Mar. 1987, vol. 97 (pp. 280-285).
Sato et al., "Massive Accumulation of Glycosaminoglycans in the Aortic Valve of a Patient With Hunter Syndrome During Enzyme Replacement Therapy," Pediatric Cardiology, 2013, vol. 34 (pp. 2077-2079).
Schwartz et al., "Clinical and biochemical studies in mucopolysaccharidosis type II carriers," Journal of Inherited Metabolic Disease, Dec. 2009, vol. 32, No. 6 (pp. 732-738).
Sestito, et al., Genetics and Gene Therapy in Hunter Disease, Current Gene Therapy 18(2):90-5.
Sharma, "In vivo genome editing: Proof of Concept in Neonatal and Adult Mouse Liver," University of Pennsylvania Dissertations 1130 (2015).
Sohn et al., "Phase I/II clinical trial of enzyme replacement therapy with idursulfase beta in patients with mucopolysaccharidosis II (Hunter Syndrome," Orphanet Journal of Rare Diseases, 2013, vol. 8, No. 42 (8 pages).
Sukegawa-Hayasaka et al., "Effect of Hunter disease (mucopolysaccharidosis type II) mutations on molecular phenotypes of iduronate-2-sulfatase: Enzymatic activity, protein processing and structural analysis," Journal of Inherited Metabolic Disease, Dec. 2006, vol. 29, No. 6 (pp. 755-761).
Tomanin et al., "Clinical efficacy of Enzyme Replacement Therapy in paediatric Hunter patients, an independent study of 3.5 years," Orphanet Journal of Rare Diseases, 2014, vol. 9, No. 129 (16 pages).
Voznyi et al., "A fluorimetric enzyme assay for the diagnosis of MPS II (Hunter disease)," Journal of Inherited Metabolic Disease, Nov. 2001, vol. 24, No. 6 (pp. 675-680).
Wechsler, et al., "ZFN-Mediated Gene Targeting at the Albumin Locus in Liver Results in Therapeutic Levels of Human FIX in Mice and Non-Human Primates," Blood 126(23):200 (2015).
Young et al., "A clinical and genetic study of Hunter's syndrome. 2 Differences between the mild and severe forms," Journal of Medical Genetics, 1982, vol. 19 (pp. 408-411).

Zanta-Boussif et al., "Validation of a mutated PRE sequence allowing high and sustained transgene expression while abrogating WHV-X protein synthesis: application to the gene therapy of WAS," Gene Therapy, 2009, vol. 16 (pp. 605-619).
Chuang et al., "Status of newborn screening and follow up investigations for Mucopolysaccharidoses I and II in Taiwan," Orphanet Journal of Rare Diseases, 2018, vol. 13, No. 84 (pp. 1-14).
Harmatz et al., "Update on phase 1/2 clinical trials for MPS I and MPS II using ZFN-mediated in vivo genome editing," Molecular Genetics and Metabolism, Feb. 2018, vol. 123, No. 2 (pp. S59-S60).
Laoharawee, et al. "Dose-Dependent Prevention of Metabolic and Neurologic Disease in Murine MPS II by ZFN-Mediated In Vivo Genome Editing," Molecular Therapy, Apr. 4, 2018, vol. 26, No. 4 (pp. 1127-1136).
Mashima et al., "Quantification of the enzyme activities of iduronate-2-sulfatase, Nacetylgalactosamine-6-sulfatase and N-acetylgalactosamine-4-sulfataseusing liquid chromatography-tandem mass spectrometry," Molecular Genetics and Metabolism Reports, 2018, vol. 14 (pp. 36-40).
Restriction Requirement mailed in U.S. Appl. No. 16/534,280 dated Nov. 16, 2021, 8 pages.
Alves, et al., "Characterization of the Nuclear Localization Signal of the Hepatitis Delta Virus Antigen," *Virology* 370(1):12-21 (2008).
Argast, et al., "I-PPOI and I-CREI Homing Site Sequence Degeneracy Determined by Random Mutagenesis and Sequential in Vitro Enrichment," *J. Mol. Biol.* 280(3):345-353 (1998).
Aronovich, et al., "Molecular Genetic Defect Underlying α-L-Lduronidase Pseudodeficiency," *Am. J. Hum. Genet.* 58:75-85 (1986).
Ashworth, et al., "Computational Redesign of Endonuclease DNA Binding and Cleavage Specificity," *Nature* 441:656-659 (2006).
Bartelink, et al., "Guidelines on Paediatric Dosing on the Basis of Developmental Physiology and Pharmacokinetic Considerations," *Clin Pharm* 45(11):1077-1097 (2006).
Beerli, et al., "Engineering Polydactyl Zinc-Finger Transcription Factors," *Nature Biotechnology* 20:135-141 (2002).
Belfort, et al., "Homing Endonucleases: Keeping the House in Order," *Nucleic Acids Res.* 25(17):3379-3388 (1997).
Bitinaite, et al., "FOKI Dimerization is Required for DNA Cleavage," *Proc. Natl. Acad Sci USA* 95:10,570-10,575 (1998).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From Xanthomonas Campestris PV. Vesicatoria," *Mol Gen Genet* 218:127-136 (1989).
Burstein, et al., "New CRISPR-CAS Systems From Uncultivated Microbes," *Nature* 542(7640):237-241 (2017).
Campos, et al., "Identification of Mucopolysaccharidosis I Heterozygotes Based on Biochemical Characteristics of L-Iduronidase From Dried Blood Spots," *Clinica Chimica Acta* 430:24-27 (2014).
Cebrian-Serrano, et al., "CRISPR-CAS Orthologues and Variants: Optimizing the Repertoire, Specificity and Delivery of Genome Engineering Tools," *Mamm Genome* 28(7):247-261 (2017).
Chevalier, et al., "Design, Activity, and Structure of a Highly Specific Artificial Endonuclease," *Molecular Cell* 10:895-905 (2002).
Choo, et al., "Advances in Zinc Finger Engineering," *Current Opinion in Structural Biology* 10:411-416 (2000).
Christian, et al., "Targeting DNA Double-Strand Breaks With TAL Effector Nucleases," *Genetics* 186(2):757-761 epub 10.1534/genetics.110.120717 (2010).
Clarke, et al., "Hunter Disease (Mucopolysaccharidosis Type II) in a Karyotypically Normal Girl," *Clin Genet* 37(5):355-362 (1990).
Cong, et al., "Multiplex Genome Engineering Using CRISPR/CAS Systems," *Science* 339(6121):819-823, DOI: 10.1126/science.1231143 (2013).
D'Aco, et al., "Diagnosis and Treatment Trends in Mucopolysaccharidosis I: Findings From the MPS I Registry," *Eur J Pediatr.* 171(6):911-919 (2012).
Dang, et al., "Identification of the Human C-MYC Protein Nuclear Translocation Signal," *Mol Cell Biol* 8(10):4048-54 (1988).
De Jong, et al., "Dimethylmethylene Blue-Based Spectrophotometry of Glycosaminoglycans in Untreated Urine: A Rapid Screening Procedure for Mucopolysaccharidoses," *Clin Chem* 35(7):1472-1477 (1989).

(56) References Cited

OTHER PUBLICATIONS

Desmet, et al., "Classification of Chronic Hepatitis: Diagnosis, Grading and Staging," *Hepatology* 19(6):1513-20 (1994).
Dingwall, et al., "The Nucleoplasmin Nuclear Location Sequence is Larger and More Complex Than That of SV-40 Large T Antigen," *J Cell Biol* 107(3):841-849 (1988).
Dujon, et al., "Mobile Introns: Definition of Terms and Recommended Nomenclaure," *Gene* 82(1):115-118 (1989).
Epinat, et al., "A Novel Engineered Meganuclease Induces Homologous Recombination in Yeast and Mammalian Cells," *Nucleic Acids Res.* 31(11):2952-2962 (2003).
Fagerlund, et al., "The CPF1 CRISPR-CAS Protein Expands Genome-Editing Tools," *Genom Bio* 16:251 (2015).
Gabathuler, "Approaches to Transport Therapeutic Drugs Across the Blood-Brain Barrier to Treat Brain Diseases," *Neurobiol Dis.* 37(1):48-57 (2010).
Garcia-Rivera, et al., "Characterization of an Immunodeficient Mouse Model of Mucopolysaccharidosis Type I Suitable for Preclinical Testing of Human Stem Cell and Gene Therapy," *Brain Res Bull.* 74(6):429-438 (2007).
Gimble, et al., "Substrate Recognition and Induced DNA Distortion by the PL-SCEL Endonuclease, An Enzyme Generated by Protein Splicing," *J. Mol. Biol.* 263(2):163-180 (1996).
Gucciardi, et al., "A Column-Switching HPLC-MS/MS Method for Mucopolysaccharidosis Type I Analysis in a Multiplex Assay for the Simultaneous Newborn Screening of Six Lysosomal Storage Disorders," *Biomed Chromatogr* 28(2):1131-9 (2014).
Guilinger, et al., "Fusion of Catalytically Inactive CAS9 to FOKL Nuclease Improves the Specificity of Genome Modification," *Nature Biotech.* 32(6):577-582 (2014).
Guo, et al., "Directed Evolution of an Enhanced and Highly Efficient FOKI Cleavage Domain for Zinc Finger Nucleases," *Journal of Molecular Biology* 400(1):96-107 (2010).
Haft, et al., "A Guild of 45 CRISPR-Associated (CAS) Protein Families and Multiple CRISPR/CAS Subtypes Exist in Prokaryotic Genomes," *PLoS Computational Biology* 1(6)e60:474-483 (2005).
Heuer, et al., "Repeat Domain Diversity of avrBs3-Like Genes in *Ralstonia solanacearum* Strains and Association With Host Preferences in the Field," *Applied and Environmental Microbiology* 73(13):4379-4384 (2007).
Hochuli, et al., "Genetic Approach to Facilitate Purification of Recombinant Proteins With a Novel Metal Chelate Adsorbent," *Bio/Technol* 6(11):1321-5 (1988).
Hopp, et al., "A Short Polypeptide Marker Sequence Useful for Recombinant Protein Identification and Purification," *Bio/Technol* 6(10):1204-10 (1988).
Hopwood, et al., "A Fluorometric Assay Using 4-Methylumbelliferyl Alpha-L-Iduronide for the Estimation of Alpha-L-Iduronidase Activity and the Detection of Hurler and Scheie Syndromes," *Clin Chim Acta.* 92(2):257-265 (1979).
Huynh, et al., "Computerized Liver Volumetry on MRI by Using 3D Geodesic Active Contour Segmentation," *AJR Am J Roentgenol* 202(1):152-59 (2014).
Isalan, et al., "A Rapid, Generally Applicable Method to Engineer Zinc Fingers Illustrated by Targeting the HIV-1 Promoter," *Nature Biotechnology* 19(7):656-660 (2001).
Isman, et al., "Lysosomal Enzymes in Human Peripheral Blood Mononuclear Cells and Granulocytes," *Clin Chem* 51(3):646-9 (2005).
Janeway, "Immunotherapy by Peptides?" *Nature* 341(6242):482-483 (1989).
Jansen, et al., "Identification of Genes That Are Associated With DNA Repeats in Prokaryotes," *Molecular Microbiology* 43(6):1565-1575 (2002).
Jasin, "Genetic Manipulation of Genomes With Rare-Cutting Endonucleases," *Trends Genet* 12:224-228 (1996).
Jinek, et al., "A Programmable Dual-RNA-Guided DNA Endonuclease in Adaptive Bacterial Immunity," *Science* 337:816-821 (2012).
Jinek, et al., "RNA-Programmed Genome Editing in Human Cells," *eLife* 2:e00471. DOI: 10.7554/eLife.00471 (2013).

Kakkis, et al., "Enzyme-Replacement Therapy in Mucopolysaccharidosis I," *NEJM* 344(3):182-8 (2001).
Kalderon, et al., "Sequence Requirements for Nuclear Location of Simian Virus 40 Large-T Antigen," *Nature* 311(5981):33-8 (1984).
Kay, et al., "A Bacterial Effector Acts As a Plant Transcription Factor and Induces a Cell Size Regulator," *Science* 318:648-651 (2007).
Kim, et al., "Hybrid Restriction Enzymes: Zinc Finger Fusions to FOK I Cleavage Domain," *Proc Nat'l Acad Sci USA* 93(3):1156-1160 (1996).
Kleinstiver, et al., "High-Fidelity CRISPR-CAS9 Variants With Undetectable Genome-Wide Off-Targets," *Nature* 529(7587):490-495, doi:10.1038/nature16526 (2016).
Krieg, et al., "Functional Messenger RNAS Are Produced by SP6 in Vitro Transcription of Cloned CDNAS," *Nuc Acid Res* 12(18):7057-70 (1984).
Langereis, et al., "A Multiplex Assay for the Diagnosis of Mucopolydsaccharidoses and Mucolipidoses," *PLoS One* 10(9):e0138622 (2015).
Ma, et al., "Rational Design of Mini-CAS9 for Transcriptional Activation," *ACS Synth Biol* 7(4):978-985 (2018).
Makarova, et al., "A DNA Repair System Specific for Thermophilic Archaea and Bacteria Predicted by Genomic Context Anlysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1(7):1-26 (2006).
Mandelli, et al., "Detection of Mucopolysaccharidosis Type I Heterozygotes Based on the Biochemical Characteristics of Leukocyte Alpha-L-Iduronidase," *Archives of Medical Research* 33(1):20-24 (2002).
McCaffery, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11 doi:10.1093/nar/gkv878. (2016).
Miao, et al., "Inclusion of the Hepatic Locus Control Region, an Intron, and Untranslated Region Increases and Stabilizes Hepatic Factor IX Gene Expression in Vivo but Not in Vitro," *Mol. Ther.* 1(6):522-532 (2000).
Moscou, et al., "A Simple Cipher Governs DNA Recognition by TAL Effectors," *Science* 326:1501 (2009).
Muenzer, "Early Initiation of Enzyme Replacement Therapy for the Mucopolysaccharidoses," *Mol Gen Metabol* 111:63-72 (2014).
Muenzer, et al., "Mucopolysaccharidosis I: Management and Treatment Guidelines," *Pediatrics* 123(1):19-29 (2009).
Offner, et al., "T Cell Receptor Peptide Therapy Triggers Autoregulation of Experimental Encephalomyelitis," *Science* 251(4992):430-432 (1991).
Okuyama, et al., "Liver-Directed Gene Therapy: A Retroviral Vector With a Complete LTR and the APOE Enhancer-Alpha 1-Antitrypsin Promoter Dramatically Increases Expression of Human Alpha 1-Antitrypsin in Vivo," *Hum Gen Ther* 7(5):637-45 (1996).
Olovnikov, et al., "Bacterial Argonaute Samples the Transcriptome to Identify Foreign DNA," *Molecular Cell* 51:594-605 (2013).
Ou, et al., "High-Dose Enzyme Replacement Therapy in Murine Hurler Syndrome," *Mol Genet Metab.* 111(2):116-122 (2014).
Ou, et al., "RTB Lectin-Mediated Delivery of Lysosomal A-L-Iduronidase Mitigates Disease Manifestations Systemically Including the Central Nervous System," *Mol Genet Metab* 123(2):105-111 (2018).
Pabo, et al., "Design and Selection of Novel CYS2-HIS2 Zinc Finger Proteins," *Ann. Rev. Biochem.* 70:313-340 (2001).
Pâques, et al., "Meganucleases and DNA Double-Strand Break-Induced Recombination: Perspectives for Gene Therapy," *Current Gene Therapy* 7(1):49-66 (2007).
Perler, et al., "Protein Splicing Elements: Inteins and Exteins—A Definition of Terms and Recommended Nomenclature," *Nucleic Acids Res.* 22(7):1125-1127 (1994).
Ponder, "Immune Response Hinders Therapy for Lysosomal Storage Diseases," *J Clin Invest* 118(8):2686-9 (2008).

(56) References Cited

OTHER PUBLICATIONS

Richardson, et al., "Nuclear Location Signals in Polyoma Virus Large-T," *Cell* 44(1):77-85 (1986).
Robbins, et al., "Two Interdependent Basic Domains in Nucleoplasmin Nuclear Targeting Sequence: Identification of a Class of Bipartite Nuclear Targeting Sequence," *Cell* 64(3):615-23 (1991).
Rome, et al., "Direct Demonstration of Binding of a Lysosomal Enzyme, Alpha-L-Iduronidase, to Receptors on Cultured Fibroblasts," *Proc Natl Acad Sci U S A* 76(5):2331-2334 (1979).
Scarpa, et al., "Mucopolysaccharidosis Type II: European Recommendations for the Diagnosis and Multidisciplinary Management of a Rare Disease," *Orphanet Journal of Rare Diseases* 6:72 (2011).
Schornack, et al., "Gene-for-Gene-Mediated Recognition of Nuclear-Targeted AVRBS3-Like Bacterial Effector Proteins," *Journal of Plant Physiology* 163(3):256-272 (2006).
Segal, et al., "Custom DNA-Binding Proteins Come of Age: Polydactyl Zinc-Finger Proteins," *Current Opinion Biotechnology* 12:632-637 (2001).
Shapiro, et al., "Neurocognition Across the Spectrum of Mucopolysaccharidosis Type I: Age, Severity, and Treatment," *Mol Genet Metab* 116(1-2):61-68 (2015).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Siomi, et al., "A Nuclear Localization Domain in the HNRNP A1 Protein," *J Cell Biol* 129(3):551-560 (1995).
Siomi, et al., "Sequence Requirements for Nucleolar Localization of Human T Cell Leukemia Virus Type I PX Protein, Which Regulates Viral RNA Processing," *Cell* 55(2):197-209 (1988).
Swarts, et al., "CRISPR Interference Directs Strand Specific Spacer Acquisition," *PLoS One* 7(4):e35888 (2012).
Swarts, et al., "DNA-Guided DNA Interference by a Prokaryotic Argonaute," *Nature* 507(7491):258-261 (2014).
Tebas, et al., "Gene Editing of CCR5 in Autologous CD4 T Cells of Persons Infected With HIV," *New Eng J Med* 370(10):901-910 (2014).
Tomatsu, et al., "Assay for Glycosaminoglycans by Tandem Mass Spectrometry and Its Applications," *J Anal Bioanal Tech.* Mar. 1(Suppl 2):006 (2014).
Troung, et al., "Development of an Intein-Mediated Split-CAS9 System for Gene Therapy," *Nucl Acid Res* 43(13):6450-8 (2015).
Vogel, "A Bacterial Seek-and-Destroy System for Foreign DNA," *Science* 344(6187):972-973 (2014).
Wasteson, et al., "Iduronate Sulfatase From Human Plasma," *Meth Enzymol* 83:573-578 (1982).
Whitley, et al., "Bone Marrow Transplantation for Hurler Syndrome: Assessment of Metabolic Correction," *Birth Defects Orig Artic Ser.* 22(1):7-24 (1986).
Whitley, et al., "A Nonpathologic Allele (IW) for Low Alpha-L-Iduronidase Enzyme Activity Vis-A-Vis Prenatal Diagnosis of Hurler Syndrome," *Am J Med Genet* 28(1):233-243 (1987).
Woychik, et al., "Requirement for the 3' Flanking Region of the Bovine Growth Hormone Gene for Accurate Polyadenylation," *Proc Natl Acad Sci* 81(13):3944-8 (1984).
Wraith, et al., "Mucopolysaccharidosis Type II (Hunter Syndrome): A Clinical Review and Recommendations for Treatment in the Era of Enzyme Replacement Therapy," *Eur J Pediatr.* 167(3):267-277 (2008).
Yang, et al., "Estimation of Standard Liver Volume Using CT Volume, Body Composition, and Abdominal Geometry Measurements," *Yonsei Med J* 59(4):546-553 (2018).
Yuan, et al., "Crystal Structure of *A. aerolicus* Argonaute, A Site-Specific DNA-Guided Endoribonuclease Provides Insights Into RISC-Mediated mRNA Cleavage," *Molecular Cell* 19:405-419 (2005).
Yuan, et al., "Estimation of Standard Liver Volume for Liver Transplantation in the Chinese Population," *Transplant Proc* 40(10):3536-40 (2008).
Zetsche, et al., "Cpf1 Is a Single RNA-Guided Endonuclease of a Class 2 CRISPR-Cas System," *Cell* 163:759-771 (2015).
Zetsche, et al., "A Split-CAS9 Architecture for Inducible Genome Editing and Transcription Modulation," *Nat Biotechnol* 33(2):139-142 (2015).
Dean, et al., "Detection of Mucopolysaccharidosis Type II by Measurement of Iduronate-2-Sulfatase in Dried Blood Spots and Plasma Samples," Clinical Chemistry 52(4):643-649 (2006).
Non-Final Office Action on U.S. Appl. No. 16/534,483 dated Aug. 17, 2022.
Au et al., "Gene therapy advances: a meta-analysis of AAV Usage in Clinical Settings," Front. Med., Sec. Translational Medicine, pp. 1-14, Feb. 9, 2022.
Harmatz, et al., "First-in-human in vivo genome editing via AAV-zinc-finger nucleases for mucopolysaccharidosis I/II and hemophilia B," Molecular Therapy, 30*12):3587-3600 (Dec. 2022).
Naso et al., "Adeno-Associated Virus (AAV) as a Vector for Gene Therapy", BioDrugs, 2017, vol. 31, pp. 317-334.
Azadeh et al., "A Rapid Two-Step Iduronate-2-Sulfatatse Enzymatic Activity Assay for MPSII Pharmacokinetic Assessment," JMD Reports, Jun. 23, 2017, 7 pgs.
Dean et al., "Detection of Mucopolysaccharidosis Type II by Measurement of Iduronate-2-Sulfatase in Dried Blood Spots and Plasma Samples," Clinical Chemistry 52:4, 2006, pp. 643-649.
Office Action in JP Patent Application No. 2021-512419, dated May 29, 2023, 9 pgs. (with translation).
Extended European Search Report in EP 19914311.6 dated Sep. 23, 2022 (7 pages).

\* cited by examiner

METHOD FOR THE TREATMENT OF MUCOPOLYSACCHARIDOSIS TYPE I

CROSS-REFERENCE TO RELATED APPLICATIONS

The present application claims the benefit of U.S. Provisional Application No. 62/802,110, filed Feb. 6, 2019 and U.S. Provisional Application No. 62/802,568, filed Feb. 7, 2019, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 20, 2019, is named 8325-01890_SL.txt and is 41,734 bytes in size.

TECHNICAL FIELD

The present invention concerns methods for treating mucopolysaccharidosis type I (MPS I), also known as Hurler syndrome, and gene therapy.

BACKGROUND

Lysosomal storage diseases (LSDs) are a group of rare metabolic monogenic diseases characterized by the lack of functional individual lysosomal proteins normally involved in the breakdown of cellular waste products, including lipids, mucopolysaccharides such as glycosoaminoglycans or GAGs. Mucopolysaccharidosis type I (MPS I), also referred to as Hurler/Hurler-Scheie/Scheie syndrome, is a recessive lysosomal storage disorder. According to the National Institute of Neurological Disorders and Stroke (NINDS) factsheet for MPS I, the estimated incidence is 1 in about 100,000 births for severe MPS I, 1 in about 500,000 births for attenuated MPS I, and 1 in about 115,000 births for disease that falls between severe and attenuated.

MPS I is associated with mutations in the gene encoding the iduronidase (IDUA) enzyme, which degrades glycosaminoglycans (sulfated carbohydrate polymers; GAGs). Mutations in the IDUA gene diminish or eliminate IDUA enzyme activity, which results in the accumulation of toxic GAGs in urine, plasma, and body tissues.

Depending upon the specific type of IDUA mutation (more than 100 different mutations have been described) and the levels of the resulting residual IDUA enzyme, patients will develop either Hurler syndrome (MPS I H) or the attenuated variants (MPS I H/S and MPS I S). It has been estimated that 50%-80% of all MPS I patients present with the severe form, which could be partly attributed to the relative ease of diagnosis (Muenzer et al. (2009) *Pediatrics* 123(1):19-29). MPS I H patients show symptoms of developmental delay before the end of their first year as well as halted growth and progressive mental decline between ages 2-4 yrs. Other symptoms include organomegaly, corneal clouding, joint stiffness and skeletal deformities (including abnormal spinal bones), coarse facial features with enlarged tongue, hearing loss and hernias. The life expectancy of these MPS I H patients is less than 10 years. Patients with the attenuated form share most of these clinical manifestations but with less severe symptoms. The clinical severity of MPS I depends on the nature of the mutational changes and the degree of residual IDUA enzyme activity. Affected individuals may develop mental retardation; other central nervous system manifestations (e.g., hydrocephalus, cervical cord compression with paraplegia/quadriplegia); organomegaly; corneal clouding; joint stiffness and contractures; skeletal deformities (including abnormal spinal bones); hearing loss (deafness); hernias; chronic restrictive and obstructive pulmonary disease; and cardiac disease including arrhythmias, valve disease, coronary artery narrowing, and, rarely, cardiomyopathy and cardiac failure.

Many of these patients can survive into adulthood but with significant morbidity. Current therapies for MPS I include hematopoietic stem cell transplant (HSCT) and enzyme replacement therapy (ERT). If patients suffering from the severe MPS I form (MPS I-H) can be diagnosed early (<2.5 yr), therapeutic intervention by HSCT (bone marrow or umbilical cord stems cells) can prevent or reverse most clinical features including neurocognition. Currently, almost all patients with MPS I H undergo HSCT. For MPS I the mortality rate after HSCT is 15% and survival rate with successful engraftment is 56%. ERT with a polymorphic recombinant protein produced in Chinese Hamster Ovary cells, Aldurazyme® (laronidase, Sanofi Genzyme), has been in use for non-CNS therapy since 2003. This enzyme has been shown to improve pulmonary function, hepatosplenomegaly, and exercise capacity and leads to improved health related quality of life. ERT should be instituted as early as possible. Limitations to enzyme replacement therapy includes the need for life-long treatment, development of neutralizing antibodies, inability to cross the blood brain barrier, continued cardiac, orthopedic, ocular complications and the inconvenience of weekly intravenous infusions. Together, these limitations underscore the urgent need to develop a broader array of curative therapies for MPS I.

SUMMARY

Disclosed herein are compositions and methods for treating and/or preventing Hurler/Hurler-Scheie/Scheie syndrome (MPS I) in a subject. The present disclosure provides methods and compositions for genome editing and/or gene transfer. The disclosure provides methods of treating a subject with MPS I comprising administering one or more polynucleotides to the subject wherein the subject is treated. Methods of treatment provided herein include methods that reduce, delay, and/or eliminate additional treatment procedures and/or the onset, progression or severity of one or more symptoms associated with MPS I. In some embodiments, the methods of treatment provided herein include methods that reduce, stabilize or eliminate GAGs in the urine of a treated subject. In some embodiments, the methods reduce, stabilize or eliminate urinary GAG levels in a subject, including before, during and after additional treatment procedures. In some embodiments, the methods of treatment provided herein increase or stabilize the concentration of active IDUA in the plasma. In some embodiments, the methods of treatment provided herein increase or stabilize the concentration of active IDUA in blood leukocytes. In some embodiments, the methods of treatment provided herein result in a reduction, stabilization or elimination of urinary GAG levels while increasing or stabilizing the concentration of IDUA in the plasma and/or leukocytes. In some embodiments, the methods of treatment provided herein result in a reduction, stabilization or elimination of urinary GAG levels wherein the concentration of IDUA in the plasma and/or leukocytes increases, stays the same or is below the level of detection. In some embodiments, the total AAV dose includes two vectors comprising ZFN encoding sequences, and 1 vector comprising the IDUA donor sequence in a fixed ratio of 1:1:8.

In some embodiments, additional treatment procedures that are reduced, delayed, and/or eliminated include enzyme replacement therapy (ERT) and/or bone marrow transplant and/or supportive surgical procedures for orthopedic, cardiac and/or upper airway obstruction (e.g. adenotonsillectomy, hernia repair, ventriculoperitoneal shunt, cardiac valve replacement, carpal tunnel release, spinal decompression, see D'aca et al. (2012) *Eur J Pediatr.* 171(6):911-919). In some embodiments, the symptoms associated with MPS I whose onset, progression or severity are reduced, delayed or eliminated, include a decline in functional abilities, neurologic deterioration, joint stiffness, becoming wheelchair dependent, progression of disability, the requirement for forced air positive ventilation (requirement for a ventilator) and a shortened life span.

An objective and rationale for the compositions and methods provided herein is to use for example, in vivo genome editing to abrogate or decrease the need for enzyme replacement therapy. Methods of treatment provided herein employ an effective dose of engineered zinc finger nucleases (ZFNs) including to site-specifically integrate a corrective copy of the enzyme α-L-iduronidase (hIDUA) transgene into the genome of a subject's own hepatocytes in vivo. In some embodiments, integration of the hIDUA transgene is targeted to intron 1 of the albumin locus, resulting in stable, liver-specific expression and secretion of α-L-iduronidase, measurable in the blood. In some embodiments, placement of the hIDUA transgene under the control of the highly expressed endogenous albumin locus provides permanent, liver-specific expression of a subject with MPS I subject.

Disclosed herein are compositions and methods for treating a subject with MPS I comprising three polynucleotides: two polynucleotides encode partner halves (also referred to as a "paired ZFN" or "left and right ZFNs") of a zinc finger nuclease and a third polynucleotide comprising a sequence encoding a functional α-L-iduronidase (IDUA) enzyme. In some embodiments, the zinc finger nuclease binds and cleaves the human albumin gene. Optionally, the nuclease-encoding polynucleotides further comprise sequences encoding small peptides (including but not limited to peptide tags and nuclear localization sequences), and/or comprise mutations in one or more of the DNA binding domain regions (e.g., the backbone of a zinc finger protein or TALE) and/or one or more mutations in a FokI nuclease cleavage domain or cleavage half domain. When these polynucleotide components are used individually or in any combination (e.g., peptide sequence such as FLAG, NLS, WPRE and/or poly A signal in any combination), the methods and compositions of the invention provide surprising and unexpected increases in expression of artificial nucleases with increased efficiency (e.g., 2, 3, 4, 5, 6, 10, 20 or more fold cleavage as compared to nucleases without the sequences/modifications described herein) and/or targeting specificity. In further embodiments, the polynucleotides encoding the zinc finger nuclease may comprise SB-47171 (SB-A6P-ZLEFT) or SB-47898 (SB-A6P-ZRIGHT) as disclosed herein. In further embodiments, the polynucleotides encoding the zinc finger nuclease may comprise SB-71557 (SB-A6P-ZL2) or SB-71728 (SB-A6P-ZR2). The composition may further comprise a polynucleotide comprising any donor nucleotide that encodes an α-L-iduronidase (IDUA) enzyme. In some embodiments, the donor nucleotide may comprise SB-IDUA (SB-A6P-HRL) as disclosed herein. In some embodiments, the three polynucleotides are delivered to the subject with MPS I who is lacking a functional IDUA gene such that a functional IDUA protein is expressed in the subject. In some embodiments, the exogenous IDUA gene is delivered to a cell in the subject together with the albumin-specific ZFN partner halves, such that the IDUA gene is integrated (inserted) into the albumin gene. In further embodiments, the IDUA gene expresses the IDUA protein such that the subject with MPS I is treated. In some embodiments, the concentration of GAGs in the urine (e.g. urinary GAG levels) in the subject is reduced, stabilized or eliminated following administration of the composition and/or treatment according to the methods provided herein.

In some embodiments, the composition comprises an effective dose of engineered zinc finger nucleases (ZFNs) to site-specifically integrate a corrective copy of a human enzyme α-L-iduronidase (hIDUA) transgene into the albumin locus of the subject's own hepatocytes in vivo. In some embodiments, the polynucleotides of the composition are carried on (delivered via) one or more AAV particles. In other embodiments, the AAV particles are AAV2/6 particles. The combination of the three AAV2/6 components, including the IDUA donor AAV, Left ZFN AAV and Right ZFN AAV, is collectively a composition of the invention. Compositions and methods for treating a subject with MPS I are effective to provide hIDUA which is active (functional) and able to degrade mucopolysaccharides glycosaminoglycans or GAGs in vivo in the subject such that the concentration of GAGs in the urine (e.g. urinary GAG level) is reduced, stabilized or eliminated following treatment and/or provide a measurable increase in the amount of active IDUA in the plasma or in leukocytes isolated from the blood. Methods for insertion of a transgene sequence into the albumin locus are provided herein wherein the transgene encodes an hIDUA protein (e.g., a functional full length or truncated IDUA protein) that is expressed (e.g. is detectable in body fluIDUA and tissues), the IDUA protein is expressed and secreted or released from a hepatocyte comprising the transgene such that the expressed IDUA protein is able to affect or be taken up by other cells that do not harbor the transgene (also referred to as a bystander effect or cross correction) and/or the IDUA is active such that urine GAGs (e.g. total GAGs, DS-GAG and/or HS-GAG) is stabilized or decreased as compared to baseline (prior to treatment as described herein).

In some embodiments, provided herein are methods of treatment that reduce, delay, and/or eliminate additional treatment procedures as compared with a subject that has not been treated with the methods and compositions as disclosed herein, for example wherein an effective amount of hIDUA transgene and zinc finger nucleases (ZFN) is administered to the subject, wherein the subject has a reduced, delayed, and/or eliminated need for additional treatment procedures after treatment. In some embodiments, the additional treatment procedures can include a bone marrow transplant, enzyme replacement therapy and/or surgical procedures for supportive treatment of cardiac, airway or orthopedic conditions associated with MPS I.

In some embodiments, the hIDUA transgene (e.g. SEQ ID NO:27) useful in the of the compositions and methods described herein is delivered (e.g. to the hepatocyte) via AAV2/6 delivery, and an hIDUA delivery vector further comprises homology arms (e.g. SEQ ID NO:13 and SEQ ID NO:16) flanking the hIDUA transgene for example, with specificity for the regions flanking the ZFN cut site in the albumin locus. In some embodiments, the left arm of homology (LA) contains about 280 nucleotides (e.g. SEQ ID NO:13) of identical sequence upstream of the albumin intron 1 cleavage site, and the right arm of homology (RA)

contains about 100 nucleotides (e.g. SEQ ID NO:16) of identical sequence downstream of the cleavage site. In some embodiments, the arms of homology are used to help facilitate targeted integration of the hIDUA transgene at the albumin intron 1 locus via homology directed repair. In some embodiments, the size of the homology arms are chosen to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises a stop codon at the 3' end, for example, to prevent further transcription of the endogenous albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-14 (SEQ ID NO:27). In some embodiments, the splice acceptor site (e.g. SA, SEQ ID NO:14) derived from hF9 exon 2 is present, for example, to allow efficient splicing of the hIDUA transcript into the mature mRNA from the albumin locus, and is effective with both types of the donor integration mechanisms (e.g. NHEJ or HDR). In some embodiments the donor comprises a sequence designated SB-IDUA AAV (e.g. Table 5; SEQ ID NO:28).

In some embodiments, the ZFN useful in the compositions and methods disclosed herein (e.g., a ZFN in which the members of the ZFN pair (left and right) ZFNs are delivered on two separate vectors) include AAV vectors designated SB-47171 AAV and SB-47898 AAV as shown in Tables 1 and 2 and the sequences following these Tables, respectively. In further embodiments, the polynucleotides encoding the zinc finger nuclease may comprise SB-71557 (SB-A6P-ZL2) or SB-71728 (SB-A6P-ZR2). In some embodiments, the ZFNs in the albumin-specific pair are delivered (e.g. to the hepatocytes) via AAV2/6 delivery, for example, wherein one AAV comprises the left ZFN (e.g. SBS-47171; SEQ ID NO:9) and another comprises the right ZFN (e.g. SBS-47898; SEQ ID NO:12). In further embodiments, the polynucleotides encoding the zinc finger nuclease may comprise SB-71557 (SB-A6P-ZL2, SEQ ID NO:23) or SB-71728 (SB-A6P-ZR2, SEQ ID NO:26). In some embodiments, ZFN expression is under control of a liver-specific enhancer and promoter, for example, comprised of the human ApoE enhancer and human α1-anti-trypsin (hAAT) promoter (Miao C H et al. (2000) *Mol. Ther.* 1(6):522-532 (200)). In some embodiments, the liver specific promoter comprises one or more ApoE enhancer sequences (e.g., 1, 2, 3 and/or 4; see Okuyama et al. (1996) *Hum Gen Ther* 7(5):637-45). In some embodiments, the promoter is linked to an intron. In some embodiments, the intron is an HGG-IGG chimeric intron comprising the 5' donor site from the first intron of the human β-globin gene and the branch and 3' acceptor site from the intron of an immunoglobulin gene heavy chain variable region. In some embodiments, the ApoE/hAAT promoter is specifically and highly active in hepatocytes, the intended target tissue, but is inactive in non-liver cell and tissue types; this prevents ZFN expression and activity in non-target tissues. In some embodiments, the transthyretin minimal promoter is used (see U.S. Patent Publication No. 2017/0119906). In some embodiments, the composition comprises SB-47171 AAV (Table 1 and sequence following Table 1); SB-47898 (Table 2 and sequence following Table 2); and SB-IDUA AAV (Table 5 and sequence following Table 5). In further embodiments, the composition comprises SB-71557 AAV (Table 3 and sequence following); SB-71728 AAV (Table 4 and sequence following); and SB-IDUA AAV (Table 5 and sequence following Table 5).

Optionally, the nuclease-encoding polynucleotides further comprise sequences encoding small peptides (including but not limited to peptide tags and nuclear localization sequences), and/or comprise mutations in one or more of the DNA binding domain regions (e.g., the backbone of a zinc finger protein or TALE) and/or one or more mutations in a FokI nuclease cleavage domain or cleavage half domain. When these polynucleotide components are used individually or in any combination (e.g., peptide sequence such as FLAG, NLS, WPRE and/or poly A signal in any combination), the methods and compositions of the invention provide surprising and unexpected increases in expression of artificial nucleases with increased efficiency (e.g., 2, 3, 4, 5, 6, 10, 20 or more fold cleavage as compared to nucleases without the sequences/modifications described herein) and/or targeting specificity. In some embodiments, the nuclease is encoded by an mRNA and the mRNA optionally comprises elements for increasing transcriptional and translational efficiency. In some embodiments, the elements comprise untranslated sequences such as natural or artificial 5' and/or 3' UTR sequences. In some aspects, a 5' UTR sequence is included in an expression cassette, while in others, a 3' UTR sequence is used. In some embodiments, an mRNA encoding an artificial nuclease comprises both a 5' UTR and a 3' UTR. In one embodiment, the 5' UTR is a *Xenopus* β-globin UTR (see Krieg and Melton (1994) *Nuc Acid Res* 12(18):7057). In some embodiments, the DNA sequence encoding the *Xenopus* β-globin UTR is 5' TGCTTGTTCTTTTTGCAGAAGCTCAGAATAAACGCT-CAACTTTGGCAGAT (SEQ ID NO:18). In some embodiments, the mRNA encoding the nuclease comprises a 3' WPRE sequence (see U.S. Patent Publication No. 2016/0326548). In some embodiments, the WPRE element is a mutated in the 'X' region to prevent expression of Protein X (see U.S. Pat. No. 7,419,829). In some embodiments, the 3' UTR comprises a poly A signal sequence. The poly A signal may be 3' or 5' to the WPRE sequence when these elements are used in combination. In some embodiments, the poly A signal sequence is the bovine Growth Hormone signal sequence (see Woychik et al. (1984) *Proc Natl Acad Sci* 81(13):3944-8).

The methods and compositions of the invention can also include mutations to one or more amino acids within the DNA binding domain outside the residues that recognize the nucleotides of the target sequence (e.g., one or more mutations to the 'ZFP backbone' (outside the DNA recognition helix region)) that can interact non-specifically with phosphates on the DNA backbone. Thus, in some embodiments, the methods and compositions disclosed herein includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In some embodiments, mutations at made at position (−5), (−9) and/or position (−14) relative to the DNA binding helix. In some embodiments, a zinc finger may comprise one or more mutations at (−5), (−9) and/or (−14). In some embodiments, one or more zinc fingers in a multi-finger zinc finger protein may comprise mutations in (−5), (−9) and/or (−14). In some embodiments, the amino acids at (−5), (−9) and/or (−14) (e.g. an arginine (R) or lysine (K))

are mutated to an alanine (A), leucine (L), Ser (S), Asp (N), Glu (E), Tyr (Y) and/or glutamine (Q). See, e.g., U.S. Patent Publication No. 2018/0087072.

In some aspects, the methods and compositions of the invention include the use of sequences encoding exogenous peptide sequences fused to eukaryotic transgene sequences. In some embodiments, exogenous peptides are fused to protein sequences post-translationally, and in other embodiments, the sequences encoding the exogenous peptides are linked in frame (3' and/or 5') to sequences encoding the artificial nuclease (e.g., a fusion protein). The exogenous peptides may encode sequences useful for purification or labeling, e.g. affinity purification or immunohistochemistry. Examples of such peptides are polyhistidine tags ("His tag", Hochuli et al. (1988) *Bio/Technol* 6(11):1321-5) or cationic peptide tags such as Flag tags (Hopp et al. (1988) *Bio/Technol* 6(10):1204-10). One or more (1, 2, 3, 4, 5 or more) of these peptide tag sequences can be used in any combinations. In some embodiments, the sequence encoding an exogenous Flag peptide comprising the sequence N-term DYKDDDK (SEQ ID NO:30) is fused in frame at the C-terminus or N-terminus of a sequence encoding an artificial nuclease. In preferred embodiments, a sequence encoding 3 FLAG sequences (3×FLAG peptide) is used (see U.S. Pat. No. 6,379,903), wherein the amino acid sequence is N-term DYKDHDG-DYKDHDI-DYKDDDDK (SEQ ID NO:31). Inclusion of one or more of such peptide sequences (e.g., 3×FLAG) can increase nuclease (cleavage) activity by 2, 3, 4, 5, 6, 7, 8, 9, 10, 11 or more fold) as compared to nucleases without the peptide sequences.

In some aspects, the mRNA encoding an artificial nuclease comprises a nuclear localization peptide sequence (NLS). In some embodiments, the NLS comprises the sequence PKKKRKV (SEQ ID NO:32) from the SV40 virus large T gene (see Kalderon et al. (1984) *Nature* 311(5981): 33-8) while in others, the NLS comprises the sequence PAAKRVKLD (SEQ ID NO:33) from the c-myc protein (see Dang and Lee (1988) *Mol Cell Biol* 8(10):4048-54). In some embodiments, the NLS comprises the sequence EGAPPAKRAR (SEQ ID NO:34) from the hepatitis delta virus (see Alves et al. (2008) *Virology* 370:12-21) or VSRKRPRP (SEQ ID NO:35) from the polyoma T protein (Richardson et al. (1986) *Cell* 44(1):77-85). In other embodiments, the NLS comprises the sequence KRPAATK-KAGQAKKKKLD (SEQ ID NO:36), derived from the nucleoplasmin carboxy tail (see Dingwall (1988) *J Cell Biol* 107:841-849 and Robbins et al. (1991) *Cell* 64(3):615-23), while in some embodiments, the NLS comprises the sequence NQSSNFGPMKGGNFG-GRSSGPYGGGGQYFAKPRNQGGY (SEQ ID NO:37) first described by Siomi and Dreyfuss (Siomi and Dreyfus (1995) *J Cell Biol* 129(3):551-560). In further embodiments, the NLS comprises the sequence PKTRRRPRRSQRKRPPT (SEQ ID NO:38) from the Rex protein in HTLV-1 (Siomi et al. (1988) *Cell* 55(2):197-209). Inclusion of one or more of NLS sequences as described herein can increase nuclease (cleavage) activity by 2, 3, 4, 5, 6, 7, 8, 9, 10, 11 or more fold) as compared to nucleases without the peptide sequences.

In some embodiments, the need for additional therapeutic procedures, such as bone marrow transplant, ERT therapy and/or supportive surgical procedures, in the subject is delayed, reduced or eliminated in the subject after treatment. In some embodiments, the delayed, reduced or eliminated need for additional therapeutic procedures is measured by a change in IDUA activity and/or level in the plasma or in leukocytes. Methods to detect IDUA in the plasma and/or in subject leukocytes are known in the art. See for example Campos et al. (2014) *Clinica Chimica Acta* 430:24-27 or Gucciardi et al. (2014) *Biomed Chromatogr* 28(2):1131-9 for methods for detection IDUA in dried blood spots, Ou et al. (2014) *Mol Genet Metab* 111(2):113-115 for methods for detection of IDUA in tissues and leukocytes, and Mandelli et al. (2002) *Archives of Medical Research* 1:20-24 which describes methods for detection of leukocyte IDUA. In some embodiments, the activity and/or level of IDUA in the plasma or in leukocytes increases post treatment, stays the same, or is below the level of detection. In some embodiments, the delayed, reduced or eliminated need for additional therapeutic procedures in the subject is measured, for example, by a change in total GAG, DS GAG (GAG comprising dermatan sulfate), and HS GAG (GAG comprising heparan sulfate) levels (for example, expressed as a ratio to creatinine) measured in the treated subject's urine. In some embodiments, the delayed, reduced or eliminated need for additional therapeutic procedures is measured, for example, by a change from baseline in forced vital capacity measured by a pulmonary function test. In some embodiments, the delayed, reduced or eliminated need for additional therapeutic procedures is measured by a change from base line, for example, in distance walked as measured by a 6-minute walk test of the subject. In some embodiments, the delayed, reduced or eliminated need for additional therapeutic procedures in the subject is measured, for example, by a change from baseline in joint range of motion (JROM). In some embodiments, the delayed, reduced or eliminated need for additional therapeutic procedures in the subject is measured, for example, by a change from baseline in spleen and/or liver volume, for example as measured by MM (before and after treatment). In some embodiments, the delayed, reduced or eliminated need for additional therapeutic procedures is measured, for example, by a change from baseline in neurocognitive abilities as measured, for example, by WASI-II (Wechsler Abbreviated Scale of Intelligence, Second Edition (Shapiro et al. (2015) *Mol Genet Metab* 116(1-2):61-68). In some embodiments, the delayed, reduced or eliminated need for additional therapeutic procedures is measured, for example, by a change from baseline in total GAG, DS GAG, and HS GAG levels measured, for example, in liver tissue and CSF.

In some embodiments, the subject has received ERT at baseline or has received ERT in the past, while in other embodiments, the subject has not received ERT.

In some embodiments, the methods and compositions disclosed herein comprise dosing of a composition of the invention, for example, via a peripheral vein catheter. In some embodiments, the composition is added to a normal saline (NS) or phosphate buffered saline (PBS) diluent, wherein the diluent may further comprise, for example, human serum albumin. In some embodiments, the subject receives a total AAV dose, for example, of 5e12 vg/kg comprising 5e11 vg/kg of each ZFN AAV2/6 comprising either a left ZFN or a right ZFN (e.g., SB-47171 AAV and SB-47898 AAV or SB-71557 AAV and SB-71728 AAV), and 4e12 vg/kg of a hIDUA donor AAV (e.g., SB-IDUA AAV). In some embodiments, the subject receives a total AAV dose, for example, of 1e13 vg/kg comprising 1e12 vg/kg of each ZFN AAV2/6 comprising, for example, either a left ZFN or a right ZFN, and 8e12 vg/kg of the hIDUA donor AAV. In further embodiments, the subject receives a total AAV dose, for example, of 5e13 vg/kg comprising 5e12 vg/kg of each ZFN AAV comprising, for example, either a left ZFN or a right ZFN, and 4e13 of the hIDUA donor AAV. In some embodiments, the subject receives a total AAV dose, for example, of 1e14 vg/kg comprising 1e13 vg/kg of each ZFN AAV2/6 comprising, for example, either a left ZFN or a right ZFN, and 8e13 vg/kg of the hIDUA donor AAV. In other embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In other embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. Any dose in the range of 1e12 to 1e16 may be used. The components may be administered separately, or, preferably a composition comprising all components (paired ZFNs on the same or different vectors and IDUA donor), for example, a composition which comprises SB-47171 AAV (Table 1), SB-47898 AAV (Table 2) and SB-IDUA AAV (Table 5). In some embodiments, the composition comprises SB-71557 AAV (Table 3), SB-71728 AAV (Table 4) and SB-IDUA AAV (Table 5).

In some embodiments, the subject has delayed, reduced or eliminated need, for example, for additional therapeutic procedures after receiving a total dose of between about 1e11 and 1e16 vg/kg, including, for example 5e12 vg/kg of the composition, of 1e13 vg/kg of the composition, of 5e13 vg/kg of the composition, of 1e14 vg/kg of the composition, of 5e14 vg/kg of the composition and/or 1e15 vg/kg of the composition. In some embodiments, the subject has delayed, reduced or eliminated need, for example, for additional therapeutic procedures (e.g., ERT) after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In another aspect, disclosed herein is a method of reducing, delaying or eliminating the symptoms in a subject with MPS I as compared with a subject that has not been treated with the methods and compositions of the invention, the method comprising, for example, administering to the subject an effective amount of hIDUA transgene and zinc finger nucleases (ZFN) wherein the subject has reduced, delayed or eliminated symptoms after treatment. In some embodiments, organomegaly, hyperactivity, aggressiveness, neurologic deterioration, joint stiffness, skeletal deformities, heart valve thickening, hearing loss, corneal clouding and vision impairment, hernias, and/or upper respiratory infections are reduced, delayed or eliminated by the compositions and methods disclosed herein. In some embodiments, the hIDUA transgene (e.g. SEQ ID NO:27) is delivered (e.g. to the hepatocyte) via AAV2/6 delivery, and the hIDUA delivery vector (e.g. as shown in SB-IDUA AAV, Table 5, e.g. SEQ ID NO:28), which further comprises homology arms (e.g. SEQ ID NO:13 and SEQ ID NO:16) flanking the hIDUA transgene with specificity for the regions flanking the ZFN cut site, for example, in the albumin locus. The left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site of the ZFNs useful in the methods and compositions disclosed herein. In some embodiments, the arms of homology are used to help facilitate targeted integration, for example, of the hIDUA transgene at the albumin intron 1 locus (e.g. via homology directed repair). In some embodiments, the size of the homology arms are chosen to avoid repetitive sequences and splicing elements, for example, in the albumin locus that can inhibit targeted integration or transgene expression. In some embodiments, the polyA sequences are derived from the bovine growth hormone gene. In some embodiments, the hIDUA transgene donor further comprises a stop codon at the 3' end, for example, to prevent further transcription of the albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-14 (SEQ ID NO:27). The splice acceptor site (SA, SEQ ID NO:14) derived from hF9 exon 2 is present to allow efficient splicing of the hIDUA transcript into the mature mRNA from the albumin locus, and is effective with both types of the donor integration mechanisms (NHEJ or HDR).

In some embodiments, the ZFNs in the albumin-specific pair are similarly delivered to the hepatocytes via AAV2/6 delivery wherein one AAV comprises the left ZFN (SBS-47171; SEQ ID NO:9) and another comprises the right ZFN (SBS-47898; SEQ ID NO:12). In some embodiments, the ZFNs in the albumin-specific pair are similarly delivered to the hepatocytes via AAV2/6 delivery wherein one AAV comprises the left ZFN (SBS-71557; SEQ ID NO:23) and another comprises the right ZFN (SBS-71728; SEQ ID NO:26). In some embodiments, the ZFN comprises two separate polynucleotides (carried on AAV vectors): SB-47171 AAV (e.g. Table 1, SEQ ID NO:9) and SB-47898 (e.g. Table 2, SEQ ID NO:12). In some embodiments, the ZFN comprises two separate polynucleotides (carried on AAV vectors): SB-71557 AAV (e.g. Table 3, SEQ ID NO:23) and SB-71728 (e.g. Table 4, SEQ ID NO:26). In some embodiments, ZFN expression is under control of a liver-specific enhancer and promoter, comprised of, for example, the human ApoE enhancer and human α1-antitrypsin (hAAT) promoter (Miao C H et al. (2000) *Mol. Ther.* 1(6):522-532 (200)). In some embodiments, the ApoE/hAAT promoter (e.g. SEQ ID NO:2) is specifically and highly active in hepatocytes, the intended target tissue in some embodiments, but is inactive in non-liver cell and tissue types; this prevents ZFN expression and activity in non-target tissues. In some embodiments, the composition comprises SB-47171 AAV (e.g. Table 1, SEQ ID NO:9); SB-47898 (e.g. Table 2, SEQ ID NO:12); and SB-IDUA AAV (e.g. Table 5, SEQ ID NO:28). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, reduced, delayed or eliminated MPS I symptoms in the subject after treatment is measured by a change in IDUA activity or level in the plasma by comparing activity or level before and after treatment. In some embodiments, the activity and/or level of IDUA in the plasma increases, stays the same, or is below the level of detection following treatment. In some embodiments, reduced, delayed or eliminated MPS I symptoms in the subject after treatment is measured by a change in IDUA activity or level in leukocytes by comparing activity or level before and after treatment. In some embodiments, the activity and/or level of IDUA in leukocytes increases, stays the same, or is below the level of detection. In some embodiments, reduced, delayed or eliminated MPS I symptoms in the subject after treatment is measured, for example, by a change in total GAG, DS GAG (e.g. GAG comprising dermatan sulfate), and HS GAG (e.g. GAG comprising heparan sulfate) levels (expressed as a ratio to creatinine) measured in the treated subject's urine. In some embodiments, reduced, delayed or eliminated MPS I symptoms in the subject after treatment is measured, for example, by a change from baseline or a stabilization in forced vital capacity measured by a pulmonary function test. In some embodiments, reduced, delayed or eliminated MPS I symptoms in the subject after treatment is measured, for example, by a change or stabilization from base line in distance walked as measured by the subject performing a 6-minute walk test before and after treatment to determine the change from base line due to treatment. In some embodiments, reduced, delayed or eliminated MPS I symptoms in the subject after treatment is measured, for example, by a change from baseline or a stabilization in joint range of motion (JROM). In some embodiments, reduced, delayed or eliminated MPS I symptoms in the subject after treatment is measured, for example, by a change from baseline or a stabilization in spleen and/or liver volume as measured by MRI. In some embodiments, reduced, delayed or eliminated MPS I symptoms in the subject after treatment is measured, for example, by a change from baseline or stabilization in neurocognitive abilities as measured by WASI-II (Wechsler Abbreviated Scale of Intelligence, Second Edition (Shapiro et al., ibid). In some embodiments, reduced, delayed or eliminated MPS I symptoms in the subject after treatment is measured, for example, by a change from baseline or stabilization in total GAG, DS GAG, and HS GAG levels measured in liver tissue and CSF.

In some embodiments, the subject has received ERT at baseline or has received ERT in the past, while in other embodiments, the subject has not received ERT.

In some embodiments, the methods and compositions disclosed herein comprise dosing of the composition, for example, via a peripheral vein catheter. In some embodiments, the composition is added to a normal saline (NS) or phosphate buffered saline (PBS) diluent, wherein the diluent may further comprise, for example, human serum albumin. In some embodiments, the subject receives a total AAV dose, for example, of 5e12 vg/kg comprising 5e11 vg/kg of each ZFN AAV2/6 comprising either a left ZFN or a right ZFN, and 4e12 vg/kg of the hIDUA donor AAV. In other embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV. In further embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV. In some embodiments, the subject receives a total AAV dose anywhere from 1e11 to 1e16, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. The method and compositions disclosed herein may be administered separately, or, preferably a composition comprising all components (e.g. paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the reduced, delayed or eliminated MPS I symptoms exhibited in the subject after use of the methods and compositions disclosed herein with a composition of the invention is seen when the subject receives a total dose, for example, of 5e12 vg/kg, of 1e13 vg/kg, of 5e13 vg/kg, of 1e14 vg/kg, of 5e14 vg/kg and/or 1e15 vg/kg. In some embodiments, the subject has reduced, delayed, or eliminated MPS I symptoms after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, methods and compositions as disclosed herein of delaying the need for ERT initiation in a subject with MPS I as compared with a subject that has not been treated with the methods and compositions of the invention as disclosed herein, the methods comprising administering to the subject, for example, an effective amount of hIDUA transgene and zinc finger nucleases (ZFN) useful in the invention, wherein the need for ERT in the subject is delayed after treatment. The hIDUA transgene (e.g. SEQ ID NO:27) is delivered (e.g. to the hepatocyte) via AAV2/6 delivery, and the hIDUA delivery vector further comprises, for example, homology arms (e.g. SEQ ID NO:13 and SEQ ID NO:16) flanking the hIDUA transgene with specificity, for example, for the regions flanking the ZFN cut site in the albumin locus. The left arm of homology (LA) contains about 280 nucleotides (e.g. SEQ ID NO:13), for example, of identical sequence upstream of the albumin intron 1 cleavage site, and the right arm of homology (RA) contains, for example, about 100 nucleotides (e.g. SEQ ID NO:16) of identical sequence downstream of the cleavage site. In some embodiments, the arms of homology are used, for example, to help facilitate targeted integration of the hIDUA transgene at the albumin intron 1 locus via homology directed repair. In some embodiments, the size of the homology arms are chosen, for example, to avoid repetitive sequences and splicing elements in the albumin locus that can inhibit targeted integration or transgene expression. The polyA sequences are derived from the bovine growth hormone gene. In some embodiments, the hIDUA transgene donor further comprises, for example, a stop codon at the 3' end to prevent further transcription of the albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-9 (e.g. SEQ ID NO:27). In some embodiments, the splice acceptor site (e.g. SA, SEQ ID NO:14), for example, derived from hF9 exon 2, is present to allow efficient splicing of the hIDUA transcript into the mature mRNA from the albumin locus, and is effective with both types of the donor integration mechanisms (e.g. NHEJ or HDR).

In some embodiments the ZFNs useful for the compositions and methods disclosed herein are similarly delivered (e.g. to the hepatocytes) via AAV2/6 delivery. In some embodiments, the ZFN is albumin-specific, for example, and the halves (left and right components) of the albumin-specific ZFNs are carried by separate AAV vectors. In some embodiments, one AAV comprises the left ZFN (e.g. SBS-47171; SEQ ID NO:9) and another comprises the right ZFN (e.g. SBS-47898; SEQ ID NO:12). In some embodiments, one AAV comprises the left ZFN (e.g. SB-71557, Table 3, SEQ ID NO:23); and another comprises the right ZFN (e.g.

SB-71728 Table 4, SEQ ID NO:26). In some embodiments, expression of the ZFNs useful in the methods and compositions disclosed herein is under control of a liver-specific enhancer and promoter, for example, comprised of the human ApoE enhancer and human α1-anti-trypsin (hAAT) promoter (Miao C H et al. (2000) *Mol. Ther.* 1(6): 522-532 (200)). In some embodiments, the ApoE/hAAT promoter (e.g. SEQ ID NO:2) is specifically and highly active (e.g. in hepatocytes and/or the intended target tissue), but is inactive in non-liver cell and tissue types; this prevents ZFN expression and activity in non-target tissues. In some embodiments, the AAV vectors comprise SB-47171 AAV (e.g. Table 1) and SB-47898 (e.g. Table 2). In some embodiments, the composition administered comprises SB-47171 AAV (e.g. Table 1, SEQ ID NO:9); SB-47898 (e.g. Table 2, SEQ ID NO:12); and SB-IDUA AAV (e.g. Table 5, SEQ ID NO:28). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the delayed need for ERT is measured, for example, in the subject after treatment. In some embodiments, the delayed need for ERT is measured, for example, by a change in IDUA activity or level in the plasma or in leukocytes. In some embodiments, the activity and/or level of IDUA in the plasma and/or leukocytes increases, stays the same, or is below the level of detection. In some embodiments, the delayed need for ERT is measured, for example, by a change or stabilization in total GAG, DS GAG (e.g. GAG comprising dermatan sulfate), and HS GAG (e.g. GAG comprising heparan sulfate) levels (for example, expressed as a ratio to creatinine) measured in the treated subject's urine (e.g. urine GAG level). In some embodiments, the delayed need for ERT is measured, for example, by a change from baseline or stabilization in forced vital capacity measured by a pulmonary function test. In some embodiments, the delayed need for ERT is measured, for example, by a change from base line or stabilization in distance walked as measured by a 6-minute walk test. In some embodiments, the delayed need for ERT is measured, for example, by a change from baseline or stabilization in joint range of motion (JROM). In some embodiments, the delayed need for ERT is measured, for example, by a change from baseline or stabilization in spleen and/or liver volume as measured by MRI. In some embodiments, the delayed need for ERT is measured, for example, by a change from baseline or stabilization in neurocognitive abilities as measured by WASI-II (Wechsler Abbreviated Scale of Intelligence, Second Edition (Shapiro et al., ibid)). In some embodiments, the delayed need for ERT is measured, for example, by a change from baseline or stabilization in total GAG, DS GAG, and HS GAG levels in liver tissue and CSF.

In some embodiments, the subject has received ERT at baseline or has received ERT in the past, while in other embodiments, the subject has not received ERT.

In some embodiments, the treatment comprises dosing of the composition, for example, via a peripheral vein catheter. In some embodiments, the composition is added to a normal saline (NS) or phosphate buffered saline (PBS) diluent. In some embodiments, the subject receives a total AAV dose, for example, of 5e12 vg/kg comprising 5e11 vg/kg of each ZFN AAV2/6 comprising either a left ZFN or a right ZFN (e.g., SB-47171 AAV or SB-71557 and SB-47898 or SB-71728 AAV), and 4e12 vg/kg of the hIDUA donor AAV (e.g., SB-IDUA AAV). In some embodiments, the subject receives a total AAV dose, for example, of 1e13 vg/kg comprising 1e12 vg/kg of each ZFN AAV2/6 comprising either a left ZFN or a right ZFN (e.g., SB-47171 or SB-71557 AAV and SB-47898 or SB-71728 AAV), and 8e12 vg/kg of the hIDUA donor AAV (e.g., SB-IDUA AAV). In some embodiments, the subject receives a total AAV dose, for example, of 5e13 vg/kg comprising 5e12 vg/kg of each ZFN AAV comprising either a left ZFN or a right ZFN (e.g., SB-47171 or SB-71557 AAV and SB-47898 or SB-71728 AAV), and 4e13 of the hIDUA donor AAV (e.g., SB-IDUA AAV). In some embodiments, the subject receives a total AAV dose of 1e11 to 1e16 vg/kg, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments, the components may be administered separately, or, preferably as a composition comprising all components (for example, paired ZFNs on the same or different vectors and IDUA donor), for example a composition which comprises SB-47171 or SB-71557 AAV (e.g. Table 1 or Table 3), SB-47898 or SB-71728 AAV (e.g. Table 2 or Table 4) and SB-IDUA AAV (e.g. Table 5).

In some embodiments, the delayed need for ERT is measured for the subject, for example, after treatment with a composition with a total dose of 5e12 vg/kg, of 1e13 vg/kg, of 5e13 vg/kg, of 1e14 vg/kg, of 5e14 vg/kg and/or 1e15 vg/kg. In some embodiments, the delayed need for ERT is measured after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In another aspect, disclosed herein is a method for removing (withdrawing) ERT in a subject with MPS I, the method comprising, for example, (a) administering to a subject receiving ERT an effective amount of an hIDUA transgene and zinc finger nucleases (ZFN) as described herein; and (b) withdrawing ERT from the subject after step (a). The ERT may be withdrawn at any time after administration, including, hours (0-48), days (1-7 days), weeks (1-4 weeks), months (1-12) or years (1-10 years) after administration of the transgene and ZFN(s). In certain embodiments, ERT is withdrawn completely while in other embodiments, ERT may be withdrawn for any period of time, including for example, a longer period of time as compared to a subject that has not been administered the transgene and ZFN(s). In some embodiments, the methods may further comprise assessing the ability to withdraw ERT in a subject by, for example, measuring one or more symptoms associated with MPS I, for example by assessing changes in organomegaly, corneal clouding and vision impairment, hyperactivity, aggressiveness, neurologic deterioration, joint stiffness, skeletal deformities, heart valve thickening, hearing loss, hernias, and/or upper respiratory infections in the subject following administration of the transgene and ZFN(s), wherein if the measurements demonstrate that one or more of these (MPS I) symptoms are reduced, delayed or eliminated by the compositions and methods disclosed herein such that ERT is no longer needed. In some embodiments, the method comprises a hIDUA transgene (e.g. SEQ ID NO:27) that is delivered (e.g. to the hepatocyte) via AAV2/6 delivery, and the hIDUA delivery vector (e.g. as shown in SB-IDUA AAV, Table 3, e.g. SEQ ID NO:28), which further comprises homology arms (e.g. SEQ ID NO:13 and SEQ ID NO:16) flanking the hIDUA transgene with specificity for the regions flanking the ZFN cut site, for example, in the albumin locus. The left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site of the ZFNs useful in the methods and compositions disclosed herein. In some embodiments, the arms of homology are used to help facilitate targeted integration, for example, of the hIDUA transgene at the albumin intron 1 locus (e.g. via homology directed repair). In some embodiments, the size of the homology arms are chosen to avoid repetitive sequences and splicing elements, for example, in the albumin locus that can inhibit targeted integration or transgene expression. In some embodiments, the polyA sequences are derived from the bovine growth hormone gene. In some embodiments, the hIDUA transgene donor further comprises a stop codon at the 3' end, for example, to prevent further transcription of the albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-14 (SEQ ID NO:27). The splice acceptor site (SA, SEQ ID NO:14) derived from hF9 exon 2 is present to allow efficient splicing of the hIDUA transcript into the mature mRNA from the albumin locus, and is effective with both types of the donor integration mechanisms (NHEJ or HDR).

In some embodiments, the ZFNs in the albumin-specific pair are similarly delivered to the hepatocytes via AAV2/6 delivery wherein one AAV comprises the left ZFN (SBS-47171 or SB-71557; SEQ ID NO:9 or SEQ ID NO:23 respectively) and another comprises the right ZFN (SBS-47898 or SB-71728; SEQ ID NO:12 or SEQ ID NO:26, respectively). In some embodiments, the ZFN comprises two separate polynucleotides (carried on AAV vectors): SB-47171 or SB-71557 AAV (e.g. Table 1, SEQ ID NO:9 or SEQ ID NO:23, respectively) and SB-47898 or SB-71728 (e.g. Table 2, SEQ ID NO:12 or SEQ ID NO:26, respectively). In some embodiments, ZFN expression is under control of a liver-specific enhancer and promoter, comprised of, for example, the human ApoE enhancer and human α1-anti-trypsin (hAAT) promoter (Miao C H et al. (2000) *Mol. Ther.* 1(6):522-532 (200)). In some embodiments, the ApoE/hAAT promoter (e.g. SEQ ID NO:2) is specifically and highly active in hepatocytes, the intended target tissue in some embodiments, but is inactive in non-liver cell and tissue types; this prevents ZFN expression and activity in non-target tissues. In some embodiments, the composition comprises SB-47171 AAV (e.g. Table 1, SEQ ID NO:9); SB-47898 (e.g. Table 2, SEQ ID NO:12); and SB-IDUA AAV (e.g. Table 3, SEQ ID NO:28). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, withdrawal of ERT in a subject with MPS I after treatment with the methods and compositions disclosed herein is assessed by one or more of the following before and after treatment: measuring a change or stabilization in IDUA activity or level in the plasma as between before and after treatment, in which increased IDUA activity after treatment is indicative that ERT can be delayed or withdrawn; measuring a change or stabilization in IDUA activity or level in the subject's leukocytes as between before and after treatment, in which increased IDUA activity after treatment is indicative that ERT can be delayed or withdrawn; measuring a change or stabilization in total GAG, DS GAG (e.g. GAG comprising dermatan sulfate), and/or HS GAG (e.g. GAG comprising heparan sulfate) levels (expressed as a ratio to creatinine) in the treated subject's urine as between before and after treatment, wherein a reduction or stabilization in levels of total GAG, DS GAG and/or HS GAG after treatment is indicative that ERT can be withdrawn or delayed; measuring a change from baseline or stabilization in forced vital capacity measured by a pulmonary function test as between before and after treatment, wherein an increase or stabilization in the forced vital capacity after treatment is indicative that ERT can be withdrawn or delayed; measuring a change from base line or stabilization in distance walked as measured by the subject performing a 6 minute walk test before and after treatment to determine the change from base line due to treatment, wherein an increase or stabilization in the distance walked by the subject after treatment is indicative that ERT can be withdrawn or delayed; measuring a change from baseline or stabilization in joint range of motion (JROM) as between before and after treatment, wherein an increase or stabilization in the range of motion after treatment is indicative that ERT can be withdrawn; measuring a change from baseline or stabilization in spleen and/or liver volume as measured by MM as between before and after treatment, wherein a decrease or stabilization in the spleen and/or liver volume after treatment is indicative that ERT can be withdrawn or delayed; measuring a change from baseline or stabilization (before treatment) in neurocognitive abilities as measured by WASI-II (Wechsler Abbreviated Scale of Intelligence, Second Edition (Shapiro et al., ibid)) wherein improvement or stabilization in neurocognitive abilities as between baseline (before) and after treatment are indicative that ERT can be withdrawn or delayed; and/or measuring a change from baseline in total GAG, DS GAG, and/or HS GAG levels measured in liver tissue and CSF before and after treatment, wherein a reduction or stabilization in total GAG, DS GAG and/or HS GAG levels after treatment are indicative that ERT can be withdrawn or delayed. ERT may thus be withdrawn or delayed in which a positive change or a stabilization is seen in one or more of these assessments after treatment (as compared to before treatment (baseline)). In some embodiments, the subject has received ERT at baseline or has received ERT in the past.

In some embodiments, the methods and compositions disclosed herein comprise dosing of the composition, for example, via a peripheral vein catheter. In some embodiments, the composition is added to a normal saline (NS) or phosphate buffered saline (PBS) diluent, wherein the diluent may further comprise, for example, human serum albumin. In some embodiments, the subject receives a total AAV dose, for example, of 5e12 vg/kg comprising 5e11 vg/kg of each ZFN AAV2/6 comprising either a left ZFN or a right ZFN, and 4e12 vg/kg of the hIDUA donor AAV. In other embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV. In further embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV. In some embodiments, the subject receives a total AAV dose of 1e11 to 1e16 vg/kg, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. The method and compositions disclosed herein may be administered separately, or, preferably a composition comprising all components (e.g. paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the ability to withdraw ERT in the subject after use of the methods and compositions disclosed herein with a composition of the invention is seen when the subject receives a total dose, for example, of 5e12 vg/kg, of 1e13 vg/kg, of 5e13 vg/kg, of 1e14 vg/kg, of 5e14 vg/kg and/or 1e15 vg/kg. In some embodiments, the ability to withdraw ERT in the subject after use of the methods and compositions disclosed herein is seen after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of delaying, reducing or preventing the need for a bone marrow transplant in a subject with MPS I as compared with a subject that has not been treated with the methods and compositions of the invention as disclosed herein, the method comprising administering to the subject an effective amount of hIDUA transgene and zinc finger nucleases (ZFN) wherein the subject has a delayed, reduced or prevented need, for example, for a bone marrow transplant after treatment with the methods and compositions disclosed herein. In some embodiments, the hIDUA transgene (e.g. SEQ ID NO:27) is delivered (e.g. to the hepatocyte) via AAV2/6 delivery, and the hIDUA delivery vector further comprises homology arms (e.g. SEQ ID NO:13 and SEQ ID NO:16) flanking the hIDUA transgene with specificity for the regions flanking the ZFN cut site in the albumin locus. The left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used, for example, to help facilitate targeted integration of the hIDUA transgene at the albumin intron 1 locus (e.g. via homology directed repair). In some embodiments, the size of the homology arms are chosen, for example, to avoid repetitive sequences and splicing elements in the albumin locus that can inhibit targeted integration or transgene expression. In some embodiment, the polyA sequences are derived from the bovine growth hormone gene. In some embodiments, the hIDUA transgene donor further comprises, for example, a stop codon at the 3' end to prevent further transcription of the albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-14 (e.g. SEQ ID NO:27). In some embodiments, the splice acceptor site (e.g. SA, SEQ ID NO:14) is derived, for example, from hF9 exon 2 to allow efficient splicing of the hIDUA transcript, for example, into the mature mRNA from the albumin locus, and is effective with both types of the donor integration mechanisms (e.g. NHEJ or HDR). In some embodiments, the donor is the donor designated SB-IDUA AAV (e.g. Table 5, SEQ ID NO:28).

In some embodiments, the ZFNs useful in the methods and compositions disclosed herein delivered to the subject are an albumin-specific pair (e.g. delivered to the hepatocytes) via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is under control, for example, of a liver-specific enhancer and promoter, comprised of the human ApoE enhancer and human α1-anti-trypsin (hAAT) promoter (Miao C H et al. (2000) *Mol. Ther.* 1(6):522-532 (200)). In some embodiments, ZFN expression is under the minimal transthyretin promoter. In some embodiments, the expression cassette comprising a ZFN comprises one or more FLAG tags (e.g., N-terminal peptide), a nuclear localization sequence (NLS), a WPRE sequence, an alternate poly A sequence, a 5' UTR or a 3' UTR as described above. In some embodiments, the ApoE/hAAT promoter (e.g. SEQ ID NO:2) is specifically and highly active (e.g. in hepatocytes, the intended target tissue), but is inactive in non-liver cell and tissue types; this prevents ZFN expression and activity in non-target tissues. In some embodiments, the ZFN pair useful in the methods and compositions disclosed herein is delivered using two separate AAV vectors, namely SB-47171 or SB-71557 AAV (e.g. Table 1, SEQ ID NO:9 or SEQ ID NO:23, respectively) and SB-47898 or SB-71728 AAV (e.g. Table 2, SEQ ID NO:12 or SEQ ID NO:26, respectively). In some embodiments, any of the methods and compositions described herein may use a three component AAV system (2 AAVs for each component of a paired ZFN and 1 AAV carrying the donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the delayed, reduced or prevented need for a bone marrow transplant is measured in the subject after treatment using the methods and compositions disclosed herein. In some embodiments, the delayed, reduced or prevented need for a bone marrow transplant is measured by a change in IDUA activity or level in the plasma. In some embodiments, the activity and/or level of IDUA in the plasma increases, stays the same, or is below the level of detection. In some embodiments, the delayed, reduced or prevented need for a bone marrow transplant is measured by a change in IDUA activity or level in the subject's leukocytes. In some embodiments, the activity and/or level of IDUA in the leukocytes increases, stays the same, or is below the level of detection. In some embodiments, the delayed, reduced or prevented need for a bone marrow transplant is measured by a change or stabilization in total GAG, DS GAG (e.g. GAG comprising dermatan sulfate), and HS GAG (e.g. GAG comprising heparan sulfate) levels (for example, expressed as a ratio to creatinine) measured in the treated subject's urine (e.g. urine GAG levels). In some embodiments, the delayed, reduced or prevented need for a bone marrow transplant is measured, for example, by a change from baseline or stabilization in forced vital capacity measured by a pulmonary function test. In some embodiments, the delayed or reduced need for a bone marrow transplant is measured, for example, by a change from base line or stabilization in distance walked as measured by a 6-minute walk test. In some embodiments, the delayed or reduced need for a bone marrow transplant is measured, for example, by a change from baseline or stabilization in joint range of motion (JROM). In some embodiments, the need for a bone marrow transplant is decreased by a change from baseline or stabilization in spleen and/or liver volume as measured, for example, by MRI. In some embodiments, the reduced, delayed or prevented need for a bone marrow transplant is measured, for example, by a change from baseline or stabilization in neurocognitive abilities as measured by WASI-II (Wechsler Abbreviated Scale of Intelligence, Second Edition (Shapiro et al., ibid)). In some embodiments, the reduced or delayed need for ERT is measured, for example, by a change from baseline or stabilization in total GAG, DS GAG, and HS GAG levels measured in liver tissue and CSF.

In some embodiments, the subject has received ERT at baseline, while in other embodiments, the subject has not received ERT.

In some embodiments, the methods and compositions disclosed herein comprises dosing of a composition (e.g. via a peripheral vein catheter). In some embodiments, the composition is added to a normal saline (NS) or phosphate buffered saline (PBS) diluent, wherein the diluent further comprises, for example, human serum albumin. In some embodiments, the subject receives a total AAV dose, for example, of 5e12 vg/kg comprising 5e11 vg/kg of each ZFN AAV2/6 comprising either a left ZFN or a right ZFN, and 4e12 vg/kg of the hIDUA donor AAV as disclosed herein. In some embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments, the components may be administered separately, or, preferably a composition comprising all components (paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the reduced, delayed or prevented need for a bone marrow transplant is measured for the subject after treatment with the methods and compositions disclosed herein, comprising a total dose of, for example, 5e12 vg/kg, of 1e13 vg/kg, of 5e13 vg/kg, of 1e14 vg/kg, of 5 vg/kg and/or 1e15 vg/kg. In some embodiments, reduced, delayed or prevented need for a bond marrow transplant is measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of reducing, stabilizing or eliminating urine GAGs (e.g. urine GAG levels) by treatment with the methods and compositions disclosed herein as compared with a subject that has not been treated, the method comprising, for example, administering to the subject an effective amount of nuclease(s) and donor(s) as described herein (e.g., a three-component composition comprising an hIDUA transgene and zinc finger nucleases (ZFN)), wherein the subject has reduced, stabilized or eliminated urine GAGs (e.g. urine GAG levels) after treatment. In some embodiments, the activity or level of IDUA in the plasma is increased, stays the same, or is below the level of detection. In some embodiments, the activity or level of IDUA in the subject's leukocytes increases, stays the same, or is below the level of detection. In some embodiments, the hIDUA transgene (e.g. SEQ ID NO:27) is delivered (e.g. to the hepatocyte) via AAV2/6 delivery, and the hIDUA delivery vector further comprises, for example, homology arms (e.g. SEQ ID NO:13 and SEQ ID NO:16) flanking the hIDUA transgene with specificity for the regions flanking the ZFN cut site in the albumin locus. In some embodiments, the left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used to help facilitate targeted integration, for example, of the hIDUA transgene at the albumin intron 1 locus via homology directed repair. In some embodiments, the size of the homology arms are chosen, for example, to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises, for example, a stop codon at the 3' end to prevent further transcription of the albumin sequences into which the IDUA transgene is inserted. In some embodiments, the rAAV2/6 donor vector comprising the human IDUA transgene (e.g. SB-IDUA donor) is a promoterless construct that comprises a partial IDUA cDNA comprising parts of exon 1 plus exons 2-14 (e.g. SEQ ID NO:27). In some embodiments, the splice acceptor site (e.g. SA, SEQ ID NO:14), for example, derived from hF9 exon 2 is present to allow efficient splicing of the hIDUA transcript into the mature mRNA from the albumin locus, and is effective with both types of the donor integration mechanisms (e.g. NHEJ or HDR). In some embodiments, the donor is the donor designated SB-IDUA AAV (e.g. Table 3, SEQ ID NO:28).

In some embodiments, the amount of total urine GAGs are stabilized or reduced in a subject by the methods and compositions disclosed herein as compared to the amount of total urine GAGs in the subject prior to treatment or as compared to total urine GAGs in a patient that has not been treated. In some embodiments, the total urine GAGs are reduced 5%, 10%, 15%, 20%, 25%, 30%, 35%, 40%, 45%, 50%, 55%, 60%, 65%, 70%, 75%, 80%, 85%, 90%, 95% or 100%, or any value there between. In some embodiments, the amount of urine dermatan sulfate GAGs are stabilized or reduced in a subject by the methods and compositions disclosed herein as compared to the amount of urine dermatan sulfate GAGs in the subject prior to treatment or as compared to urine dermatan sulfate GAGs in a patient that has not been treated. In some embodiments, the urine dermatan sulfate GAGs are reduced 5%, 10%, 15%, 20%, 25%, 30%, 35%, 40%, 45%, 50%, 55%, 60%, 65%, 70%, 75%, 80%, 85%, 90%, 95% or 100%, or any value there between. In some embodiments, the amount of urine heparan sulfate GAGs are stabilized or reduced in a subject by the methods and compositions disclosed herein as compared to the amount of urine heparan sulfate GAGs in the subject prior to treatment or as compared to urine heparan sulfate GAGs in a patient that has not been treated. In some embodiments, the urine heparan sulfate GAGs are reduced 5%, 10%, 15%, 20%, 25%, 30%, 35%, 40%, 45%, 50%, 55%, 60%, 65%, 70%, 75%, 80%, 85%, 90%, 95% or 100%, or any value there between. In some embodiments, GAG levels are used as a biochemical marker to assess treatment effect once a patient has withdrawn from ERT following treatment with the compositions disclosed herein. GAG measurements are most useful when used in conjunction with an assessment of other clinical parameters for the patient.

In some embodiments, the ZFNs useful in the methods and compositions disclosed herein in the albumin-specific pair are similarly delivered (e.g. to the hepatocytes) via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is under control, for example, by a liver-specific enhancer and promoter, comprised of the human ApoE enhancer and human α1-anti-trypsin (hAAT) promoter (Miao C H et al. (2000) Mol. Ther. 1(6):522-532 (200)). In some embodiments, the ApoE/hAAT promoter (e.g. SEQ ID NO:2) is specifically and highly active (e.g. in hepatocytes, the intended target tissue), but is inactive in non-liver cell and tissue types; this prevents ZFN expression and activity in non-target tissues. In some embodiments, ZFN expression is under the minimal transthyretin promoter. In some embodiments, the expression cassette comprising a ZFN comprises one or more FLAG tags (e.g. N-terminal peptide), a nuclear localization sequence (NLS), a WPRE sequence, an alternate poly A sequence, a 5' UTR or a 3' UTR as described above. In some embodiments, the ZFNs and IDUA donor are delivered, for example, using a composition comprising all three components: two AAV vectors for each component of a paired ZFN and 1 AAV carrying the donor (e.g., a composition which comprises SB-47171 or SB-71557 AAV (e.g. Table 1), SB-47898 or SB-71728 AAV (e.g. Table 2) and SB-IDUA AAV (e.g. Table 5)).

In some embodiments, reduced, stabilized or eliminated urine GAGs (e.g. urine GAG levels) is measured in the subject's urine after treatment with the methods and compositions disclosed herein. In some embodiments, reduced, stabilized or eliminated GAGs in the urine (for example urine GAG levels, heparan sulfate GAGs, and/or dermatan sulfate GAGs) is measured by any method known in the art. Exemplary methods to measure urine GAGs include the Dimethyl Methylene Blue (DMB) assay (see e.g. de Jong et al. (1989) Clin Chem 35/7:1472-1479); a method dependent on serine proteases and a labeled substrate for the serine protease, an inhibitor of the serine protease, and a urine sample suspected of comprising one or more glycosaminoglycans (see e.g. U.S. Patent Publication No. 2013/0189718); a multiplex assay (Langereis et al. (2015) PLoS One 10(9):e0138622) based on enzymatic digestion the of heparan sulfate (HS), dermatan sulfate (DS) and keratan sulfate (KS) found in the urine, followed by quantification by LC-MS/MS; and an assay that can be used to determine the concentration of specific types of GAGs that utilizes a RapidFire (RF, Agilent) high-throughput mass spectrometry system (see Tomatsu et al. (2014) J Anal Bioanal Tech. March 1; 2014 (Suppl 2):006).

In some embodiments, the subject has received ERT at baseline or has received ERT in the past, while in other embodiments, the subject has not received ERT.

In some embodiments, the treatment using the methods and compositions as disclosed herein of the subject comprises dosing of a composition of the invention, for example, via a peripheral vein catheter. In some embodiments, the composition is added to a normal saline (NS) or phosphate buffered saline (PBS) diluent, wherein the diluent further comprises, for example, human serum albumin. In some embodiments, the subject receives a total AAV dose, for example, of 5e12 vg/kg comprising 5e11 vg/kg of each ZFN AAV2/6 comprising either a left ZFN or a right ZFN, and 4e12 vg/kg of the hIDUA donor AAV as disclosed herein. In some embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose of 1e11 to 1e16 vg/kg, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments, the components may be administered separately, or, preferably a composition comprising all components (paired ZFNs on the same or different vectors and IDUA donor), for example a composition which comprises SB-47171 AAV (e.g. Table 1), SB-47898 AAV (e.g., Table 2) and SB-IDUA AAV (e.g. Table 3). In some embodiments, the composition comprises SB-71557 AAV (e.g. Table 4, SEQ ID NO:23); SB-71728 (e.g. Table 5, SEQ ID NO:26); and SB-IDUA AAV (e.g. Table 5, SEQ ID NO:28).

In some embodiments, the reduced, stabilized or eliminated urine GAGs is measured for the subject, for example after a treatment with a composition of the invention at a total dose of 5e12 vg/kg, of 1e13 vg/kg, of 5e13 vg/kg, of 1e14 vg/kg, of 5e14 vg/kg and/or 1e15 vg/kg. In some embodiments, the reduced, stabilized or eliminated urine GAGs is measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of improving, delaying a decline or maintaining the functional ability in a subject with MPS I by treating the subject with a standard dosing regimen, for example, of ERT in combination with treatment with a composition of the invention as disclosed herein, as compared with a subject that has not been treated, the method comprising administering to the subject an effective amount of hIDUA transgene and zinc finger nucleases (ZFN) and with a standard ERT dose, wherein the subject has, for example, an improvement in functional ability, a delay in decline or maintenance of functional ability after treatment. In some embodiments, the hIDUA transgene (e.g. SEQ ID NO:27) is delivered to the hepatocyte via AAV2/6 delivery, and the hIDUA delivery vector further comprises homology arms (e.g. SEQ ID NO:13 and SEQ ID NO:16) flanking the hIDUA transgene with specificity for the regions flanking the ZFN cut site in the albumin locus. In some embodiments, the left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used, for example, to help facilitate targeted integration of the hIDUA transgene at the albumin intron 1 locus via homology directed repair. In some embodiments, the size of the homology arms are chosen, for example, to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises a stop codon, for example, at the 3' end to prevent further transcription of the albumin sequences into which the IDUA transgene is inserted. In some embodiments, the rAAV2/6 donor vector containing the human IDUA transgene (e.g. SB-IDUA donor) is a promoterless construct, for example, that comprises a partial IDUA cDNA comprising parts of exon 1 plus exons 2-14 (e.g. SEQ ID NO:27). In some embodiments, the splice acceptor site (e.g. SA, SEQ ID NO:14) derived, for example, from hF9 exon 2 is present to allow efficient splicing of hIDUA transgene into the mature mRNA from the albumin locus, and is effective with both types of the donor integration mechanisms (e.g. NHEJ or HDR). In some embodiments, the donor is the donor designated SB-IDUA AAV (e.g. Table 5, SEQ ID NO:28).

In some embodiments, the ZFNs in the albumin-specific pair are similarly delivered (e.g. to the hepatocytes) via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is under control, for example, by a liver-specific enhancer and promoter, comprised of the human ApoE enhancer and human α1-anti-trypsin (hAAT) promoter (Miao C H et al. (2000) *Mol. Ther.* 1(6):522-532 (200)). In some embodiments, ZFN expression is under the minimal transthyretin promoter. In some embodiments, the expression cassette comprising a ZFN comprises one or more FLAG tags (e.g. N-terminal peptide), a nuclear localization sequence (NLS), a WPRE sequence, an alternate poly A sequence, a 5' UTR or a 3' UTR as described above. In some embodiments, the ApoE/hAAT promoter (e.g. SEQ ID NO:2) is specifically and highly active (e.g., in hepatocytes, the intended target tissue), but is inactive in non-liver cell and tissue types; this prevents ZFN expression and activity in non-target tissues.

In some embodiments, improvement in, delay in decline or maintenance of functional ability after treatment with the methods and compositions disclosed herein, is measured in the subject after treatment. In some embodiments, an improvement in, delay in decline or maintenance of functional ability is measured, for example, by a change from baseline in forced vital capacity measured by a pulmonary function test. In some embodiments, an improvement in, delay in decline or maintenance of functional ability is measured, for example, by a change from base line in distance walked measured by a 6-minute walk test. In some embodiments, the improvement in, delay in decline or maintenance of functional ability is measured, for example, by a change from baseline in joint range of motion. In some embodiments, the improvement in, delay in decline or maintenance of functional ability is measured, for example, by a change from baseline in neurocognitive abilities as measured by WASI-II (Wechsler Abbreviated Scale of Intelligence, Second Edition (Shapiro et al., ibid)).

In some embodiments, the subject has received ERT at baseline or has received ERT in the past, while in other embodiments, the subject has not received ERT.

In some embodiments, the treatment comprises dosing of a composition of the invention (e.g. via a peripheral vein catheter). In some embodiments, the composition is added to a normal saline (NS) or phosphate buffered saline (PBS) diluent, wherein the diluent further comprises human serum albumin. In some embodiments, the subject receives a total AAV dose, for example, of 5e12 vg/kg comprising 5e11 vg/kg of each ZFN AAV2/6 comprising either a left ZFN or a right ZFN, and 4e12 vg/kg of the hIDUA donor AAV as disclosed herein. In other embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose of 1e11 to 1e16 vg/kg, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiment the components may be administered separately, or, preferably a composition comprising all components (paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the improvement in, delay in decline or maintenance of function ability is measured for the subject, for example, after a treatment with a composition of the invention at a total dose of 5e12 vg/kg, of 1e13 vg/kg, of 5e13 vg/kg, of 1e14 vg/kg, of 5e14 vg/kg and/or 1e15 vg/kg. In some embodiments, the improvement in, delay in decline, or maintenance of functional ability is measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of suppressing or delaying disability progression in a human subject having MPS I as compared with a subject that has not been treated with the methods and compositions of the invention, the method comprising administering to the subject an effective amount of hIDUA transgene and zinc finger nucleases (ZFN) wherein the subject has a stabilization, suppression or delay in disability progression after treatment with the methods and compositions as disclosed herein. In some embodiment, the hIDUA transgene (e.g. SEQ ID NO:27) is delivered (e.g. to the hepatocyte) via AAV2/6 delivery, and the hIDUA delivery vector further comprises homology arms (e.g. SEQ ID NO:13 and SEQ ID NO:16) flanking the hIDUA transgene that have specificity for the regions flanking the ZFN cut site in the albumin locus. In some embodiments, the left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used, for example, to help facilitate targeted integration of the hIDUA transgene at the albumin intron 1 locus via homology directed repair. In some embodiments, the size of the homology arms were chosen, for example, to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises, for example, a stop codon at the 3' end to prevent further transcription of the albumin sequences into which the IDUA transgene is inserted. In some embodiments, the rAAV2/6 donor vector containing the human IDUA transgene (e.g. SB-IDUA donor) is a promoterless construct that comprises, for example, a partial IDUA cDNA comprising parts of exon 1 plus exons 2-14 (e.g. SEQ ID NO:27). In some embodiments, the splice acceptor site (e.g. SA, SEQ ID NO:14) derived, for example, from hF9 exon 2 is present to allow efficient splicing of the hIDUA transcript into the mature mRNA from the albumin locus, and is effective with both types of the donor integration mechanisms (NHEJ or HDR). In some embodiments, the donor is the donor designated SB-IDUA AAV (e.g. Table 5, SEQ ID NO:28).

In some embodiments, the ZFNs in the albumin-specific pair are similarly delivered (e.g. to the hepatocytes) via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is controlled by a liver-specific enhancer and promoter, for example, comprised of the human ApoE enhancer and human α1-anti-trypsin (hAAT) promoter (Miao C H et al. (2000) Mol. Ther. 1(6):522-532 (200)). In some embodiments, ZFN expression is under the minimal transthyretin promoter. In some embodiments, the expression cassette comprising a ZFN comprises one or more FLAG tags (e.g. N-terminal peptide), a nuclear localization sequence (NLS), a WPRE sequence, an alternate poly A sequence, a 5' UTR or a 3' UTR as described above. In some embodiments, the ApoE/hAAT promoter (e.g., SEQ ID NO:2) is specifically and highly active in hepatocytes, the intended target tissue, but is inactive in non-liver cell and tissue types; this prevents ZFN expression and activity in non-target tissues.

In some embodiments, stabilization, suppression or delay of disability progression is measured in the subject after treatment with the methods and compositions as disclosed herein. In some embodiments, stabilization, suppression or delay of disability progression is measured, for example, by a change from baseline or stabilization in forced vital capacity measured by a pulmonary function test. In some embodiments, stabilization, suppression or delay of disability progression is measured, for example, by a change from base line or stabilization in distance walked measured by a 6-minute walk test. In some embodiments, stabilization, suppression or delay of disability progression is measured, for example, by a change from baseline or stabilization in joint range of motion (JROM). In some embodiments, stabilization, suppression or delay of disability progression is measured, for example, by a change from baseline or stabilization in neurocognitive abilities as measured by WASI-II (Wechsler Abbreviated Scale of Intelligence, Second Edition (Shapiro et al., ibid)).

In some embodiments, the subject has received ERT at baseline or has received ERT in the past, while in other embodiments, the subject has not received ERT.

In some embodiments, the treatment comprises dosing of a composition of the invention (e.g. via a peripheral vein catheter). In some embodiments, the composition is added to a normal saline (NS) or phosphate buffered saline (PBS) diluent. In some embodiments, the subject receives a total AAV dose, for example of 5e12 vg/kg comprising 5e11 vg/kg of each ZFN AAV2/6 comprising either a left ZFN or a right ZFN, and 4e12 vg/kg of the hIDUA donor AAV as disclosed herein. In some embodiments, the subject receives a total AAV dose, for example of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments the components may be administered separately, or, preferably a composition comprising all components (paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the delayed need for ERT is measured for the subject after treatment with a composition of the invention via a total dose of 5e12 vg/kg, of 1e13 vg/kg, of 5e13 vg/kg of 1e14 vg/kg, of 5e14 vg/kg and/or 1e15 vg/kg. In some embodiments, the delayed need for ERT measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of stabilizing, delaying, reducing or preventing the need for the use of a medical ventilator device in a subject with MPS I as compared with a subject that has not been treated with the methods and compositions as disclosed herein, the method comprising administering to the subject an effective amount of hIDUA transgene and zinc finger nucleases (ZFN) wherein the subject has a delay, reduction or prevention of the need for the use of a medical ventilator device. In some embodiments, the hIDUA transgene (SEQ ID NO:27) is delivered (e.g. to the hepatocyte) via AAV2/6 delivery, and the hIDUA delivery vector further comprises homology arms (e.g. SEQ ID NO:13 and SEQ ID NO:16) flanking the hIDUA transgene with specificity for the regions flanking the ZFN cut site in the albumin locus. In some embodiments, the left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used to help facilitate targeted integration of the hIDUA transgene at the albumin intron 1 locus via homology directed repair. In some embodiments, the size of the homology arms were chosen to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises a stop codon at the 3' end to prevent further transcription of the albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-14 (e.g. SEQ ID NO:27). The splice acceptor site (e.g. SA, SEQ ID NO:14) derived from hF9 exon 2 is present to allow efficient splicing of hIDUA transgene into the mature mRNA from the albumin locus, and is effective with both types of the donor integration mechanisms (e.g. NHEJ or HDR). In some embodiments, the donor is the donor designated SB-IDUA AAV (e.g. Table 5, SEQ ID NO:28).

In some embodiments, the ZFNs in the albumin-specific pair are similarly delivered to the hepatocytes via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is controlled by a liver-specific enhancer and promoter, comprised of the human ApoE enhancer and human al-antitrypsin (hAAT) promoter (Miao C H et al. (2000) *Mol. Ther.* 1(6):522-532 (200)). In some embodiments, ZFN expression is under the minimal transthyretin promoter. In some embodiments, the expression cassette comprising a ZFN comprises one or more FLAG tags (e.g. N-terminal peptide), a nuclear localization sequence (NLS), a WPRE sequence, an alternate poly A sequence, a 5' UTR or a 3' UTR as described above. In some embodiments, the ApoE/hAAT promoter (e.g. SEQ ID NO:2) is specifically and highly active in hepatocytes, the intended target tissue, but is inactive in non-liver cell and tissue types; this prevents ZFN expression and activity in non-target tissues. In some embodiments, the stabilized, delayed, reduced or prevented need for the use of a ventilator is measured in the subject after treatment. In some embodiments, the stabilized, delayed, reduced or prevented need for use of a ventilator is measured, for example, by a change from baseline in forced vital capacity measured by a pulmonary function test. In some embodiments, the stabilized, delayed, reduced or prevented need for use of a ventilator is measured, for example, by a change from base line in distance walked measured by a 6-minute walk test.

In some embodiments, the treatment using the methods and compositions as disclosed herein comprises dosing of with a composition of the invention (e.g. via a peripheral vein catheter). In some embodiments, the composition is added to a normal saline (NS) or phosphate buffered saline (PBS) diluent, wherein the diluent further comprises human serum albumin. In some embodiments, the subject receives a total AAV dose, for example of 5e12 vg/kg comprising 5e11 vg/kg of each ZFN AAV2/6 comprising either a left ZFN or a right ZFN, and 4e12 vg/kg of the hIDUA donor AAV as disclosed herein. In other embodiments, the subject receives a total AAV dose, for example of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments, the components may be administered separately, or, preferably a composition comprising all components (paired ZFNs on the same or different vectors and IDUA donor), for example a composition which comprises SB-47171 AAV (e.g., Table 1), SB-47898 AAV (e.g., Table 2) and SB-IDUA AAV (e.g., Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the reduced or delayed need for use of a ventilator is measured for the subject after treatment with a composition of the invention with a total dose of 5e12 vg/kg, of 1e13 vg/kg, of 5e13 vg/kg, of 1e14 vg/kg, of 5e14 vg/kg and/or 1e15 vg/kg. In some embodiments, the reduced or delayed need for use of a ventilator is measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of stabilizing, delaying, reducing or preventing the onset of a subject being wheelchair dependent in a human subject having MPS I as compared to a subject that that has not been treated with the methods and compositions as disclosed herein, the method comprising administering to the subject an effective amount of hIDUA transgene and zinc finger nucleases (ZFN) wherein the subject has a stabilized, delayed, reduced or prevented onset of being wheelchair dependent after treatment. In some embodiments, the hIDUA transgene (e.g. SEQ ID NO:27) is delivered to the hepatocyte via AAV2/6 delivery, and the hIDUA delivery vector further comprises homology arms (e.g. SEQ ID NO:13 and SEQ ID NO:16) flanking the hIDUA transgene that are specific for the regions flanking the ZFN cut site in the albumin locus. In some embodiments the left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used to help facilitate targeted integration of the hIDUA transgene at the albumin intron 1 locus via homology directed repair. In some embodiments, the size of the homology arms are chosen to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises a stop codon at the 3' end to prevent further transcription of the albumin sequences into which the IDUA transgene is inserted. In some embodiments, the rAAV2/6 donor vector containing the human IDUA transgene (e.g. SB-IDUA donor) is a promoterless construct that comprises a partial IDUA cDNA comprising parts of exon 1 plus exons 2-14 (e.g. SEQ ID NO:27). The splice acceptor site (e.g. SA, SEQ ID NO:14) derived from hF9 exon 2 is present to allow efficient splicing of the hIDUA transcript into the mature mRNA from the albumin locus, and is effective with both types of the donor integration mechanisms (e.g. NHEJ or HDR). In certain embodiments, the donor is the donor designated SB-IDUA AAV (e.g. Table 5, SEQ ID NO:28).

In some embodiments, the ZFNs in the albumin-specific pair are similarly delivered to the hepatocytes via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is controlled by a liver-specific enhancer and promoter, comprised of the human ApoE enhancer and human al-antitrypsin (hAAT) promoter (Miao C H et al. (2000) *Mol. Ther.* 1(6):522-532 (200)). In some embodiments, the expression cassette comprising a ZFN comprises one or more FLAG tags (e.g. N-terminal peptide), a nuclear localization sequence (NLS), a WPRE sequence, an alternate poly A sequence, a 5' UTR or a 3' UTR as described above. In some embodiments, the ApoE/hAAT promoter (e.g. SEQ ID NO:2) is specifically and highly active in hepatocytes, the intended target tissue, but is inactive in non-liver cell and tissue types; this prevents ZFN expression and activity in non-target tissues.

In some embodiments, stabilized, delayed, reduced or the prevention of the onset of being wheelchair dependent is measured in the subject after treatment. In some embodiments, stabilized, delayed, reduced or prevention of the onset of being wheelchair dependent is measured by a change from baseline in forced vital capacity measured by a pulmonary function test. In some embodiments, stabilized, delayed, reduced or prevention of the onset of being wheelchair dependent is measured by a change from base line or stabilization in distance walked measured by a 6-minute walk test. In some embodiments, stabilized, delayed, reduced or prevention of onset of being wheelchair dependent is measured by a change from baseline or stabilization in joint range of motion. In some embodiments stabilization, delay, reduction or prevention of the onset of being wheelchair dependent is measured by WASI-II (Wechsler Abbreviated Scale of Intelligence, Second Edition (Shapiro et al., ibid)). In some embodiments, stabilization or delaying onset of confirmed disability progression or reducing the risk of confirmed disability progression is measured by a change from baseline or stabilization in total GAG, DS GAG, and HS GAG levels measured in liver tissue and CSF.

In some embodiments, the subject has received ERT at baseline or has received ERT in the past, while in other embodiments, the subject has not received ERT.

In some embodiments, the treatment comprises dosing with a composition of the invention via a peripheral vein catheter. In some embodiments, the composition is added to a normal saline (NS) or phosphate buffered saline (PBS) diluent, wherein the diluent further comprises human serum albumin. In some embodiments, the subject receives a total AAV dose of 5e12 vg/kg comprising 5e11 vg/kg of each ZFN AAV2/6 comprising either a left ZFN or a right ZFN, and 4e12 vg/kg of the hIDUA donor AAV. In other embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose of 1e11 to 1e16 vg/kg, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments, the components may be administered separately, or, preferably a composition comprising all components (e.g. paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the stabilized, delayed, reduced or the prevention of the onset of being wheelchair dependent is measured for the subject after a total dose of 5e12 vg/kg SB-913, of 1e13 vg/kg, of 5e13 vg/kg of 1e14 vg/kg, of 5e14 vg/kg and/or 1e15 vg/kg. In some embodiments, the stabilized, delayed, reduced or prevention of the onset of being wheelchair dependent is measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In some embodiments, provided herein is a method of extending life expectancy in a subject with MPS I as compared with a subject that has not been treated with the methods and compositions as disclosed herein, the method comprising administering to the subject an effective amount of hIDUA transgene and zinc finger nucleases (ZFN) wherein the subject has an extended life expectancy. In some embodiments, the hIDUA transgene (e.g. SEQ ID NO:27) is delivered to the hepatocyte via AAV2/6 delivery, and the hIDUA delivery vector further comprises homology arms (e.g. SEQ ID NO:13 and SEQ ID NO:16) flanking the hIDUA transgene that are specific for the regions flanking the ZFN cut site in the albumin locus. The left arm of homology (LA) contains about 280 nucleotides (e.g. SEQ ID NO:13) of identical sequence upstream of the albumin intron 1 cleavage site, and the right arm of homology (RA) contains about 100 nucleotides (e.g. SEQ ID NO:16) of identical sequence downstream of the cleavage site. In some embodiments, the arms of homology are used to help facilitate targeted integration of the hIDUA transgene at the albumin intron 1 locus via homology directed repair. In some embodiments, the size of the homology arms were chosen to avoid repetitive sequences and splicing elements in the albumin locus that can inhibit targeted integration or transgene expression. In some embodiments, the polyA sequences are derived from the bovine growth hormone gene. In some embodiments, the hIDUA transgene donor further comprises a stop codon at the 3' end to prevent further transcription of the albumin sequences into which the IDUA transgene is inserted. In some embodiments, the rAAV2/6 donor vector containing the human IDUA transgene (SB-IDUA donor) is a promoterless construct that comprises a partial IDUA cDNA comprising parts of exon 1 plus exons 2-14 (SEQ ID NO:27). In some embodiments, the splice acceptor site (e.g. SA, SEQ ID NO:14) derived from hF9 exon 2 is present to allow efficient splicing of the hIDUA transcript into the mature mRNA from the albumin locus, and is effective with both types of the donor integration mechanisms (e.g. NHEJ or HDR). In certain embodiments, the donor is the donor designated SB-IDUA AAV (e.g. Table 5 and sequence following Table 5).

In some embodiments, the ZFNs in the albumin-specific pair are similarly delivered to the hepatocytes via AAV2/6 delivery wherein one AAV comprises the left ZFN (e.g. SBS-47171 or SB-71557; SEQ ID NO:9 or SEQ ID NO:23, respectively) and another comprises the right ZFN (e.g. SBS-47898 or SB-71728; SEQ ID NO:12 or SEQ ID NO:26, respectively). In some embodiments, ZFN expression is controlled by a liver-specific enhancer and promoter, comprised of the human ApoE enhancer and human al-antitrypsin (hAAT) promoter (Miao C H et al. (2000) *Mol. Ther.* 1(6):522-532). In some embodiments, ZFN expression is under the minimal transthyretin promoter. In some embodiments, the expression cassette comprising a ZFN comprises one or more FLAG tags (e.g. N-terminal peptide), a nuclear localization sequence (NLS), a WPRE sequence, an alternate poly A sequence, a 5' UTR or a 3' UTR as described above. In some embodiments, the ApoE/hAAT promoter (e.g. SEQ ID NO:2) is specifically and highly active in hepatocytes, the intended target tissue, but is inactive in non-liver cell and tissue types; this prevents ZFN expression and activity in non-target tissues. In some embodiments, the extension of life expectancy measured in the subject after treatment.

In some embodiments, the treatment comprises dosing of a composition as disclosed herein via a peripheral vein catheter. In some embodiments, the composition is added to a normal saline (NS) or phosphate buffered saline (PBS) diluent, wherein the diluent further comprises human serum albumin. In some embodiments, the subject receives a total AAV dose, for example, of 5e12 vg/kg comprising 5e11 vg/kg of each ZFN AAV2/6 comprising either a left ZFN or a right ZFN, and 4e12 vg/kg of the hIDUA donor AAV as disclosed herein. In some embodiments, the subject receives a total AAV dose, for example, of 1e13 vg/kg comprising 1e12 vg/kg of each ZFN AAV2/6 comprising either a left ZFN or a right ZFN, and 8e12 vg/kg of the hIDUA donor AAV as disclosed herein. In some embodiments, the subject receives a total AAV dose, for example, of 5e13 vg/kg comprising 5e12 vg/kg of each ZFN AAV comprising either a left ZFN or a right ZFN, and 4e13 of the hIDUA donor AAV as disclosed herein. In some embodiments, the subject receives a total AAV dose, for example, of 1e14 vg/kg comprising 1e13 vg/kg of each ZFN AAV2/6 comprising, for example, either a left ZFN or a right ZFN, and 8e13 vg/kg of the hIDUA donor AAV. In some embodiments, the subject receives a total AAV dose, for example, of 5e14 vg/kg comprising 5e13 vg/kg of each ZFN AAV2/6 comprising, for example, either a left ZFN or a right ZFN, and 4e14 vg/kg of the hIDUA donor AAV. In some embodiments, the subject receives a total AAV dose, for example, of 1e15 vg/kg comprising 1e14 vg/kg of each ZFN AAV2/6 comprising, for example, either a left ZFN or a right ZFN, and 8e14 vg/kg of the hIDUA donor AAV. In some embodiments, the components may be administered separately, or, preferably a composition comprising all components (paired ZFNs on the same or different vectors and IDUA donor), for example a composition which comprises SB-47171 AAV (e.g. Table 1), SB-47898 AAV (e.g. Table 2) and SB-IDUA AAV (e.g. Table 5). In some embodiments, the composition comprises SB-71557 AAV (e.g. Table 3, SEQ ID NO:23); SB-71728 (e.g. Table 4, SEQ ID NO:26); and SB-IDUA AAV (e.g. Table 5, SEQ ID NO:28).

In some embodiments, the extended life expectancy is measured for the subject after treatment with a composition of the invention at a total dose of 5e12 vg/kg, of 1e13 vg/kg, of 5e13 vg/kg, of 1e14 vg/kg, of 5e14 vg/kg and/or 1e15 vg/kg. In some embodiments, the extended life expectancy is measured for the subject after receiving a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg).

In certain embodiments, a) the need for additional therapeutic procedures in a subject having MPS I is decreased or stabilized; b) the symptoms in a subject having MPS I are decreased or stabilized, c) the amount of GAGs in the urine of a subject with MPS I are reduced, stabilized or eliminated; d) the functional ability in a subject having MPS I is improved or stabilized; e) the need for ERT in a subject with MPS I is decreased or stabilized; f) the need for ERT in a subject with MPS I is delayed or stabilized; g) the dose and/or frequency of ERT treatment stabilizes or decreases in a subject with MPS I that is also treated with a composition as disclosed herein, and/or the subject has stabilized or increased functional ability as compared to a MPS-I subject treated with ERT alone; h) the risk of disability progression in a subject with MPS I is stabilized or decreased; i) the onset of confirmed disability progression is stabilized or delayed in a subject treated with a composition of the invention, j) there is a delay in becoming wheelchair dependent or the need for a wheelchair is abolished; k) the need for the use of a mechanical ventilator is stabilized, reduced, delayed or prevented; 1) life expectancy in a subject treated with a composition of the invention is expanded as compared to a subject that has not been treated with the composition.

In some embodiments, the subject is premedicated prior to infusion with a composition of the invention. In some embodiments, the subject is premedicated with prednisone or an equivalent corticosteroid the day prior to infusion with the composition. In some embodiments, the subject is premedicated with prednisone or equivalent corticosteroid on the day prior to infusion with the composition and again on the day of infusion. In some embodiments, the subject is premedicated with prednisone or equivalent corticosteroid on the day prior to infusion with the composition, again on the day of infusion, and/or again on day 7, and/or at week 2, and/or week 4, and/or week 6, and/or week 8 up to a maximum duration of week 20.

In some embodiments of the methods described above and herein, the MPS I is the early onset, severe form of the disease with somatic and cognitive involvement, while in other embodiments, the MPS I is the attenuated MPS I characterized by later onset of somatic disease and little or no central nervous system disease. In further embodiments, the MPS I disease is on the continuum between the two. In some embodiments, the subjects are adults while in some embodiments, the subjects are from the pediatric population.

In certain embodiments according to (or as applied to) any of the embodiments above, the subject is selected for treatment based on having the early onset, severe form of MPS I, while in other embodiments, the subject has the attenuated MPS I characterized by a later onset of somatic disease with little or no central nervous system disease, while in some embodiments, the subject is selected for treatment based on having MPS I disease that is on the continuum between the two.

In some embodiments of the methods described above and herein, a composition of the invention is administered at a total dose of 5e12 vg/kg, of 1e13 vg/kg, of 5e13 vg/kg, of 1e14 vg/kg, of 5e14 vg/kg and/or 1e15 vg/kg. In some embodiments of the method described above and herein, a composition of the invention is administered at a total dose of between 5e12 vg/kg to 1e15 vg/kg (for example, between 5e12 vg/kg and 5e13 vg/kg, between 5e12 vg/kg and 1e14 vg/kg, between 5e12 vg/kg and 5e14 vg/kg and/or between 5e12 vg/kg and 1e15 vg/kg). In some embodiments of the methods described above and herein, the composition is administered intravenously.

In any of the methods above or herein, a stabilization, reduction or decrease or improvement after administration of a composition of the invention can be compared to a baseline level, to a level in untreated subject(s) and/or to a level in subject(s) receiving a different treatment (such as ERT). In some embodiments, a reduction or decrease or improvement after administration of the composition can be compared to a level in subject(s) receiving Aldurazyme®.

In another aspect, provided herein is an article of manufacture comprising one or more of the compositions described herein. In certain embodiments, the article of manufacture comprises a formulation that includes three pharmaceutical compositions (e.g., in different containers such as vials) as described herein: a first pharmaceutical composition comprising one member of a ZFN pair (e.g., left ZFN); a second pharmaceutical composition comprising the second member of the ZFN pair (e.g., right ZFN); and a third pharmaceutical composition comprising an IDUA donor (e.g., AAV IDUA donor). Any concentration of the components can be used, including but not limited to the concentrations shown in Table 6. Further, any ratio of the three pharmaceutical compositions can be used, for example 1:1:8 (left ZFN:right ZFN:IDUA donor). The different components may be labeled in any way, for example with different colors used for each composition. In certain embodiments, the article of manufacture comprises: a set of drug product vials comprising i) the ZFN1 vector drug product (SB-A6P-ZLEFT), optionally in a container (e.g., vial) comprising an aluminum flip-top seal having a first color (e.g., white); ii) the ZFN 2 vector drug product (SB-A6P-ZRIGHT), optionally in a container (e.g., vial) comprising an aluminum flip-top seal having a second color different from the first color (e.g., blue); and iii) the third vector SB-A6P-HRL drug product, encoding a DNA repair template encoding a promotorless IDUA transgene, optionally in a container (e.g., vial) comprising a third color different from the first and second colors (e.g., red) aluminum flip-top seal. In further embodiments, a set of drug products comprising AAV vectors encoding SB-71557 (SB-A6P-ZL2, SEQ ID NO:23) or SB-71728 (SB-A6P-ZR2, SEQ ID NO:26) and SB-A6P-HRL vector is provided. In any of the compositions described herein, the purified lots of recombinant vector may be formulated in phosphate buffered saline (PBS) containing $CaCl_2$), MgCl2, NaCl, Sucrose and poloxamer 188 filled at volumes of 5 mL into glass drug product vials, b) a package insert with instructions for treating MPS I in a subject according to any one of the methods described above and herein. The article of manufacture (drug product) is administered (e.g., intravenously) to a subject in need thereof such that IDUA is expressed in the subject, including at therapeutic levels for treatment of MPS I at any concentration suitable for the subject (e.g., determined based on weight as described herein). Administration may be one-time or multiple times at any frequency. In addition, the set of drug products may be administered separately or may be combined prior to administration, for example in an intravenous infusion bag.

In another aspect, a method of determining the dose of compositions (e.g., to form an article of manufacture/set of drug products) as described herein for a selected subject is provided, the method comprising: determining the subject's weight (rounded to two decimal points) before treatment (baseline); dividing the subject's weight by the vg/mL concentration to determine the dose to be used. For example, for a 50 kg subject to be treated at Cohort 1, 0.5e14 vg of ZFN1 (e.g. 47171 or 71557), 0.5e14 vg of ZFN2 (e.g. 47898 or 71729) and 4e14 SB-IDUA are used. Further, these steps are carried out: (i) Calculate the three product component volumes by multiplying the cohort dose by the patient weight at Baseline and then dividing by the VG concentration, for example as follows: (a). Obtain the cohort and patient weight at Baseline from the study coordinator (b). Obtain the VG concentrations from the Clinical Certificates of Analysis. (ii) Calculate the total volume by adding together the three product component volumes and the NS/PB S volume. (iii) Calculate the volume of HSA intravenous solution required to achieve a final concentration of 0.25% HSA, and (iv) Calculate the adjusted NS/PBS volume. The methods may further comprise providing a formulation (e.g., including an article of manufacture comprising three drug products as described herein) with the correct dosage for the subject's weight, by determining a total volume; and calculating the volume of human serum albumin (HSA) intravenous solution needed, thereby achieving the correct component concentration for the selected subject.

In some embodiments, the dose is determined by volume of the liver of the subject. Weight of a subject does not always directly correlate with liver volume, especially in heavier patients. In pediatric patients less than 2 months of age, optimal dosage of different therapeutics can be based on liver volume to avoid hepatic toxicity (see Bartelink et al. (2006) *Clin Pharm* 45(11):1077-1097). Thus, for some subjects, dose may be determined by approximate liver volume. In these instances, liver volume may be estimated by methods known in the art, for example by use of formulas based on a combination of parameters such as age, gender, body weight, body height, body mass index and body surface area (Yuan et al. (2008) *Transplant Proc* 40(10): 3536-40). Other methods for estimating or determining of liver volume known in the art include CT or MRI scans and estimations of abdominal geometry (Yang et al. (2018) *Yonsei Med J* 59(4):546-553; Huynh et al. (2014) *AJR Am J Roentgenol* 202(1):152-59).

In another aspect, provided herein is a method of administering a composition as described herein, the method comprising providing an article of manufacture as described herein (e.g., a drug product comprising three (AAV) pharmaceutical compositions (left ZFN, right ZFN, AAV donor) separately or together as described herein), formulating one or more intravenous solutions at a selected dose for a subject (e.g., using the methods described herein) and intravenously administering the intravenous solution to the subject in need thereof. In certain embodiments, the three components (ZFN1, ZFN2 and IDUA donor) of the article of manufacture are added separately to an approximately 200 mL IV infusion bag, for example an IV infusion bag containing 0.25% HSA in NS or PBS. Total infusion volumes are calculated according to the subject's cohort assignment and body weight (kg) and are expected to be between approximately 240-800 mL depending on subject's cohort assignment and body weight (kg). The prepared infusion product will be administered via intravenous infusion at 100 mL/hour using a constant rate infusion pump, while the subject is in the hospital or acute care facility. Any of the methods described herein may be delivered using an infusion pump, at any rate, for example, 10 to 200 mL/hour (or any value therebetween). In certain embodiments, the intravenous solution is delivered at a rate of 100 mL/hour. Subjects may be receiving ERT or received ERT in the past. In certain embodiments, ERT not given during the week of infusion of the intravenous solution.

Also provided are methods of increasing levels (activity) of IDUA in leukocytes of a subject, the methods comprising administering an intravenous solution as described herein (e.g., a system comprising three pharmaceutical compositions). In certain embodiments, the IDUA levels are increased from below normal (in MPS I subjects) to levels in the normal range (levels in non-MPS I subjects). Increased IDUA levels/activity can be determined by measuring IDUA levels/activity directly and/or measuring GAG levels. IDUA levels (activity) in plasma and urine may also be increased using the methods and compositions described herein.

In any of the methods described herein, the subject may receive a corticosteroid (e.g., prednisone), for example 1, 2, 3, 4, 5, 6, 7 or more days before infusion of the intravenous, the day of infusion and/or up to 20 or more weeks after infusion, wherein the dosage is determined based on the subject's weight. An exemplary schedule of oral prednisone tapering dose over time determined by the subject's weight is shown below in Table A:

TABLE A

Tapering steroid dose

| | Oral Prednisone (mg/day) | | | | | |
|---|---|---|---|---|---|---|
| Weight of subject | Day −2 to Day 1 | Week 1 | Week 2 | Week 3-16 | Week 17-19 | Week 20 |
| ≥60 | 60 | 60 | 30 | 15 | 5 | STOP |
| 55 | 60 | 60 | 30 | 15 | 5 | STOP |
| 50 | 50 | 50 | 25 | 15 | 5 | STOP |
| 45 | 45 | 45 | 25 | 15 | 5 | STOP |
| 40 | 40 | 40 | 20 | 10 | 5 | STOP |
| 35 | 35 | 35 | 20 | 10 | 5 | STOP |
| 30 | 30 | 30 | 15 | 10 | 5 | STOP |

In some embodiments, other doses (including higher or lower) of corticosteroid or other immunosuppressants may be used (e.g. 2.0, 1.5 mg/kg/day of prednisolone or more, or methotrexate at 7.5-15.5 mg/week) than those exemplified in Table A. In some embodiments, initiation of the taper occurs later (for example, at 4, 5, 6, 7, or 8 or more weeks) than exemplified in Table A.

These and other aspects will be readily apparent to the skilled artisan in light of disclosure as a whole.

BRIEF DESCRIPTION OF THE DRAWINGS

FIG. 1A shows the catabolic breakdown of dermatan sulfate. FIG. 1B shows the catabolic breakdown of heparan sulfate. MPS I disease results in the inability to participate in the process of breaking down both dermatan sulfate and heparan sulfate, leading to the accumulation of these GAGs in nearly all organs and body tissues and in the urine of a subject with MPS I. Chronic accumulation of GAGs inside cellular lysosomes results in cellular engorgement, organomegaly, tissue destruction, and organ system dysfunction in MPS I patients.

DETAILED DESCRIPTION

Figure 1A:
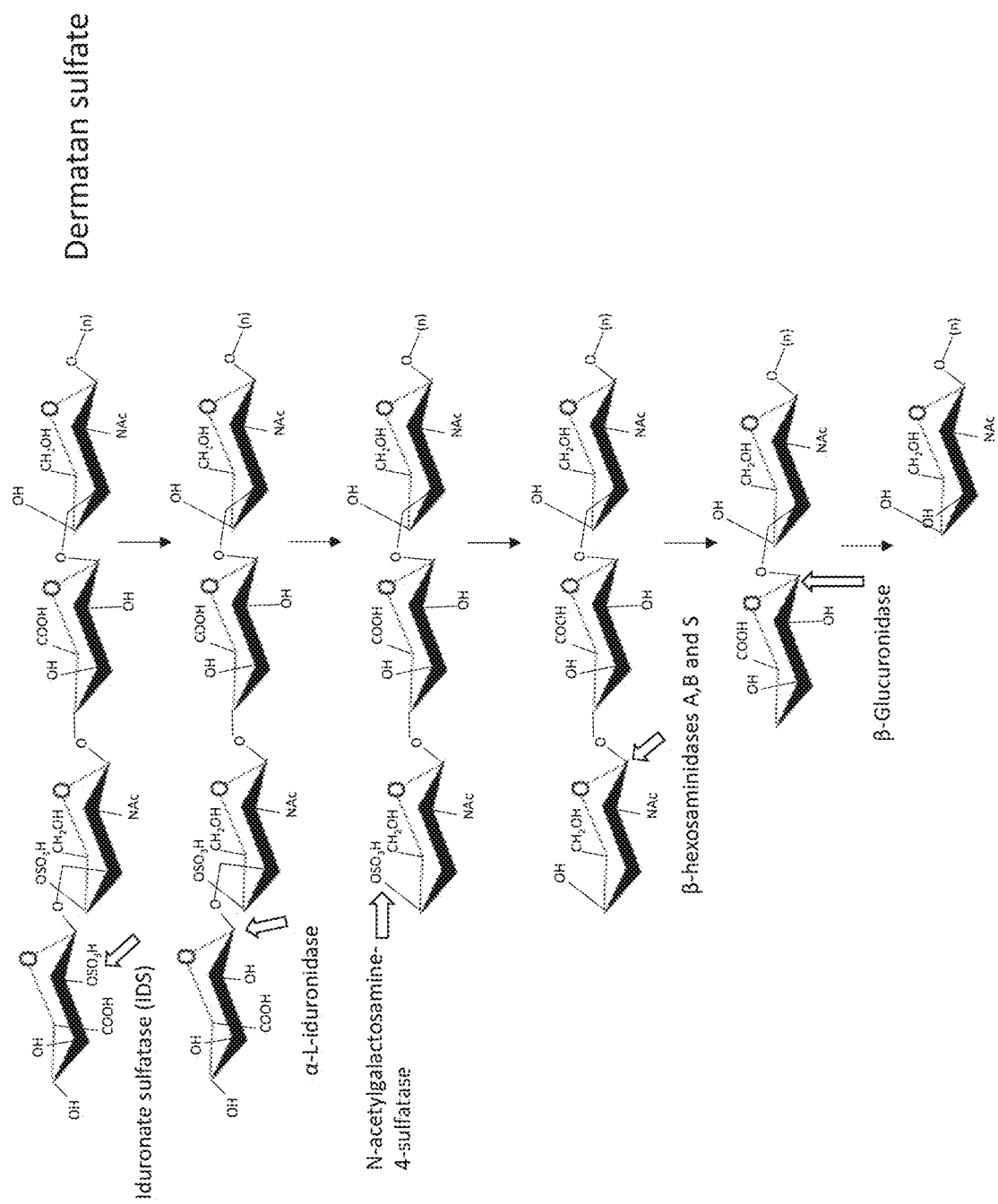
FIGS. 1A and 1B are diagrams depicting the breakdown of glucosaminoglycans (GAGs).

Disclosed herein are methods and compositions for treating and/or preventing Hurler/Hurler-Scheie/Scheie (MPS I) syndrome in a human subject comprising insertion of a suitable transgene sequence in a target cell. The treatment employs engineered zinc finger nucleases (ZFNs) to site-specifically integrate a corrective copy of the enzyme iduronidase (hIDUA) transgene into the albumin locus of the subject's own hepatocytes in vivo. Once expressed from the integrated transgene, the hIDUA is active and able to degrade mucopolysaccharides glycosaminoglycans (GAG). The invention describes methods of prevention or treatment for MPS I subjects.

Normally, IDUA enzyme is produced inside the cell and a small amount of it may leak out into the circulation due to cells' imperfect internal transport system. A steady state is established as extracellular enzyme is taken back up by receptors on the cells' surface. As a result, most of the enzyme normally produced in the body is found in the tissues, and there are generally very small concentrations of enzyme found in circulation. In contrast, ERT is an infusion directly into the bloodstream of a large bolus of enzyme designed to create high concentrations in the circulation to allow uptake into IDUA-deficient tissues. However, ERT only produces transient high levels of IDUA enzyme, followed by rapid clearance from the circulation within a matter of minutes to hours due to the short half-life of the enzyme, and because large amounts are taken up by the liver. This limits the effectiveness of ERT because it only provides a short window of exposure of enzyme to the tissues, and we know that enzyme uptake by the cells is a slow receptor-mediated process. Instead, an ideal therapy for MPS I would allow prolonged and sustained exposure of the IDUA enzyme to the tissues by producing and maintaining continuous, stable levels of enzyme in the circulation. Even low amounts of IDUA secreted continuously into the circulation could be adequate to reduce tissue GAGs and potentially provide efficacy for the compositions disclosed herein.

ERT has been shown to increase the amount of IDUA activity in patient's leukocytes following treatment, presumably because the cells take up the enzyme from the plasma (leukocytes are lysosome-rich cells). For example, in a study of patients receiving recombinant IDUA, it was reported (see Kakkis et al. (2001) *NEJM* 344(3):182-8) that the mean activity of IDUA in leukocytes was 0.04 U per mg prior to treatment, and following treatment, it was measured at 4.98 U per mg seven days after infusion (i.e. immediately prior to the next treatment). Thus measurement of IDUA in the circulating leukocytes can be useful for determining the presence of the enzyme in the blood.

Lysosomal storage diseases (LSDs) are a group of rare metabolic monogenic diseases characterized by the lack of functional individual lysosomal proteins normally involved in the breakdown of waste lipids, mucopolysaccharides (i.e. glycosoaminoglycans (GAG)). These diseases are characterized by a buildup of these compounds in the cell since it is unable to process them for recycling due to the mis-functioning of a specific enzyme in the breakdown pathway. The pathophysiology of LSD was initially thought to be tied to the simple deposition of GAG, but current research has led to an appreciation of the complexities of these diseases. GAG storage appears to lead to the perturbation of cellular, tissue and organ homeostasis, and has also been linked to increased secretion of cytokine and inflammatory modulators leading to an activation of the inflammatory response (Muenzer (2014) *Mol Gen Metabol* 111:63-72).

Mucopolysaccharidosis type I (MPS I), also referred to as Hurler/Hurler-Scheie/Scheie syndrome, is a recessive lysosomal storage disorder. According to the National Institute of Neurological Disorders and Stroke (NINDS) factsheet for MPS I, the estimated incidence is 1 in about 100,000 births for severe MPS I, 1 in about 500,000 births for attenuated MPS I, and 1 in about 115,000 births for disease that falls between severe and attenuated.

MPS I is associated with mutations in the gene encoding the iduronidase (IDUA) enzyme, which degrades and/or helps recycle glycosaminoglycans (sulfated carbohydrate polymers; GAGs). Mutations in the IDUA gene diminish or eliminate IDUA enzyme activity, which results in the accumulation of toxic GAGs in urine, plasma, and body tissues which leads to widespread tissue and organ damage.

Depending upon the specific type of IDUA mutation (more than 100 different mutations have been described) and the levels of the resulting residual IDUA enzyme, patients will develop either Hurler syndrome (MPS I H) or the attenuated variants (MPS I H/S and MPS I S). It has been estimated that 50%-80% of all MPS I patients present with the severe form, which could be partly attributed to the relative ease of diagnosis (Muenzer et al., ibid). MPS I H patients show symptoms of developmental delay before the end of their first year as well as halted growth and progressive mental decline between ages 2-4 yrs. Other symptoms include organomegaly, corneal clouding, joint stiffness and skeletal deformities (including abnormal spinal bones), coarse facial features with enlarged tongue, hearing loss and hernias. The life expectancy of these MPS I H patients is less than 10 years. Patients with the attenuated form share most of these clinical manifestations but with less severe symptoms. In addition, there is no CNS involvement and therefore they do not suffer from mental retardation.

Many of these patients can survive into adulthood but with significant morbidity. Current standard of care for MPS I include hematopoietic stem cell transplant (HSCT) for severe patients, and enzyme replacement therapy (ERT) given through frequent intravenous infusions. If patients suffering from the severe MPS I form (MPS I-H) can be diagnosed early (<2.5 yr), therapeutic intervention by HSCT (bone marrow or umbilical cord stems cells) can prevent or reverse most clinical features including neurocognition. Currently, almost all patients with MPS I H undergo HSCT. For MPS I the mortality rate after HSCT is 15% and survival rate with successful engraftment is 56% ERT with a polymorphic recombinant protein produced in Chinese Hamster Ovary cells, Aldurazyme®, has been in use since 2003. This enzyme has been shown to improve pulmonary function, hepatosplenomegaly, and exercise capacity and leads to improved health related quality of life. ERT should be instituted as early as possible. Limitations to enzyme replacement therapy includes the need for life-long treatment, development of neutralizing antibodies, inability to cross the blood brain barrier, continued cardiac, orthopedic, ocular complications and the inconvenience of weekly intravenous infusions. Together, these limitations underscore the urgent need to develop a broader array of curative therapies for MPS I.

The objective and rationale for the methods and compositions disclosed herein is to abrogate or decrease the need for enzyme replacement therapy by in vivo genome editing. The proposed treatment employs engineered zinc finger nucleases (ZFNs) to site-specifically integrate a corrective copy of the iduronidase enzyme (hIDUA) transgene into the genome of the subject's own hepatocytes in vivo. Integration of the hIDUA transgene is targeted to intron 1 of the albumin locus, resulting in stable, high level, liver-specific expression and secretion of iduronidase into the blood. Placement of the huIDUA transgene under the control of the highly expressed endogenous albumin locus is expected to provide permanent, liver-specific expression of iduronidase for the lifetime of an MPS I patient.

Patients with mild MPS I receiving weekly ERT were enrolled in the study. One patient has been dosed with 1e13 vg/kg of the compositions disclosed herein and two patients have been dosed with 5e13 vg/kg. None of the three patients enrolled in the study have received bone marrow transplant. Interim data results show dose-dependent increases in leukocyte IDUA enzyme activity in all three subjects treated with the methods and compositions disclosed herein. Leukocytes are an easily accessible target tissue for IDUA and therefore provide one estimate of tissue enzyme activity for patients with MPS I. In patients with MPS I who have received a bone marrow transplant, increased leukocyte IDUA activity is associated with successful engraftment and improved clinical outcomes.

Administration of the composition described herein was generally well-tolerated. No treatment related serious adverse events (SAEs) have been reported. Of the 6 total adverse events (AEs) reported, all were mild or moderate and consistent with ongoing MPS I disease, and none were considered related to treatment with the compositions described herein. A dose-dependent increase in leukocyte IDUA activity was observed in all three patients treated with the compositions described herein, with activity levels rising above baseline and in the normal range (normal range is 6.0-71.4 nmol/hr/mg). Plasma IDUA activity was unchanged from baseline in all three patients. Baseline urine GAG measurements for the three patients were in a range considered to be at or slightly above normal. In the limited duration preliminary data set urine GAG measurements show no clear trend with no meaningful change at this time. Additional follow up is needed to observe whether any meaningful change in urine GAGs emerges.

Second-generation, potentially more potent ZFN constructs (for example, SB-71557 and SB-71728) were designed to increase editing efficiency, among other improvements. The preclinical data showed three potential ZFN 2.0 advantages: (1) a 5- to 30-fold improvement in efficiency and potency due to structural changes; (2) the ability to function equally well in the patients who have a single nucleotide polymorphism (SNP) in the target locus in the albumin gene (approximately 20% of the population); and, (3) improved specificity (see U.S. Provisional Patent Application No. 62/758,786). These ZFN compositions will also be tested.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. The term "zinc finger nuclease" includes one ZFN as well as a pair of ZFNs (the members of the pair are referred to as "left and right" or "first and second" or "pair") that dimerize to cleave the target gene.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. Nos. 8,586,526 and 9,458,205. The term "TALEN" includes one TALEN as well as a pair of TALENs (the members of the pair are referred to as "left and right" or "first and second" or "pair") that dimerize to cleave the target gene. Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,568,526; 6,140,081; 6,453,242; and 6,534,261; see also International Patent Publication Nos. WO 98/53058; WO 98/53059; WO 98/53060; WO 02/016536; and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197; and WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing" in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, U.S. Pat. Nos. 7,888,121; 7,914,796; 8,034,598; and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "disease associated gene" is one that is defective in some manner in a monogenic disease. Non-limiting examples of monogenic diseases include severe combined immunodeficiency, cystic fibrosis, lysosomal storage diseases (e.g. Gaucher's, Hurler's Hunter's, Fabry's, Neimann-Pick, Tay-Sach's etc), sickle cell anemia, and thalassemia.

The "blood brain barrier" is a highly selective permeability barrier that separates the circulating blood from the brain in the central nervous system. The blood brain barrier is formed by brain endothelial cells which are connected by tight junctions in the CNS vessels that restrict the passage of blood solutes. The blood brain barrier has long been thought to prevent the uptake of large molecule therapeutics and prevent the uptake of most small molecule therapeutics (Pardridge (2005) *NeuroRx* 2(1):3-14).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmIDUA and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene" for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Red Blood Cells" (RBCs) or erythrocytes are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry $CO_2$ produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional" protein, polypeptide or nucleic acid includes any protein, polypeptide or nucleic acid that provides the same function as the wild-type protein, polypeptide or nucleic acid. A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Figure 1B:
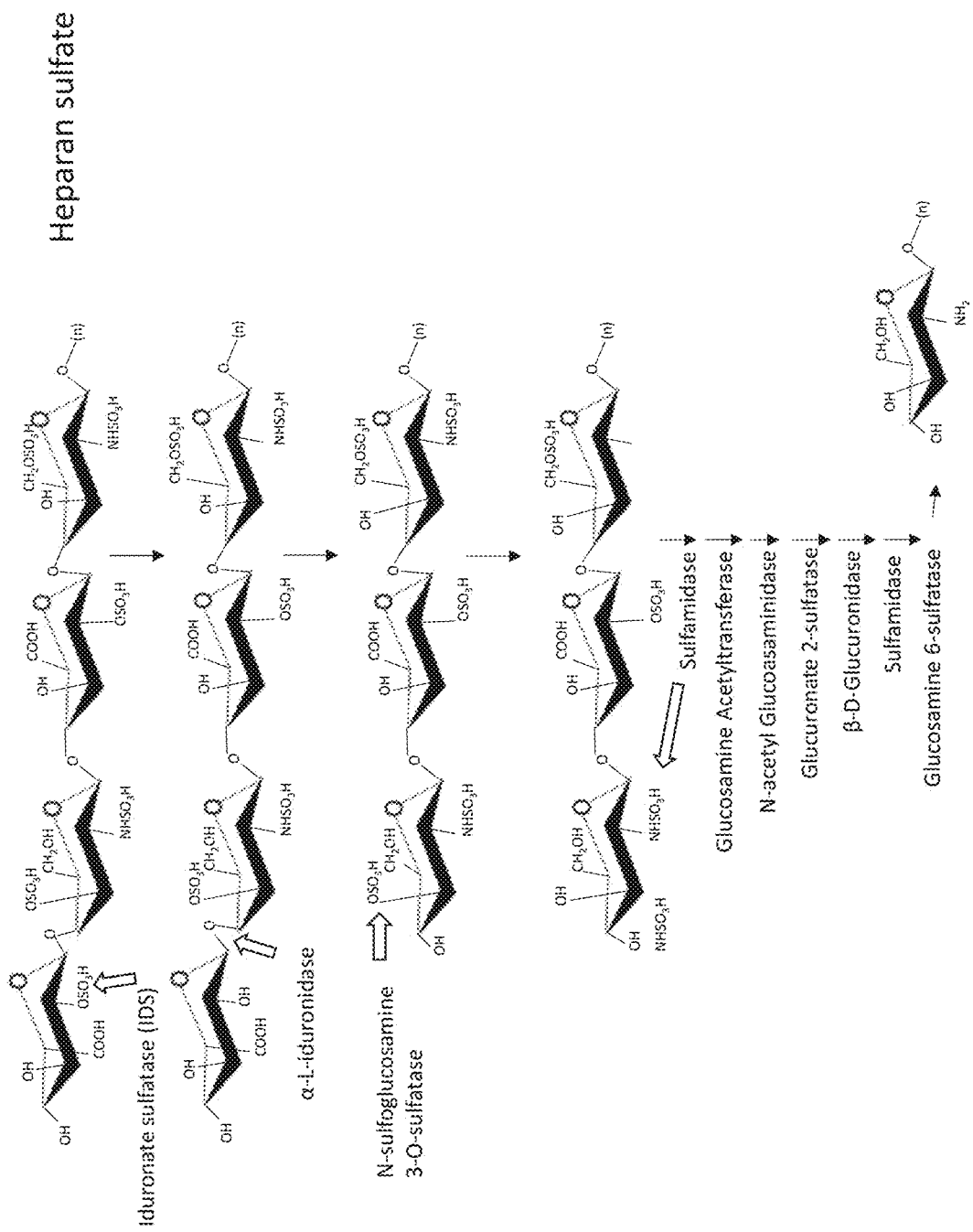

The extracellular matrix that surrounds and binds certain types of cells is composed of numerous components, including fibrous structural proteins, such as various collagens, adhesive proteins like laminin and fibronectin, and proteoglycans that form the gel into which the fibrous structural proteins are embedded. Proteoglycans are very large macromolecules consisting of a core protein to which many long polysaccharide chains called glycosaminoglycans are covalently bound. Due to the high negative charge of the glycosaminoglycans, the proteoglycans are very highly hydrated, a property that allows the proteoglycans to form a gel-like matrix that can expand and contract. The proteoglycans are also effective lubricants. "Glycosoaminoglycans" or "GAGs" are long, linear polymers of unbranched polysaccharides consisting of a repeating disaccharide unit. The repeating unit (except for keratan) consists of an amino hexose sugar (N-acetylglucosamine or N-acetylgalactosamine) along with an acidic uronic sugar (glucuronic acid or iduronic acid) or galactose. The exception to this general structure is keratan sulfate, which has galactose in place of the acidic hexose. Glycosaminoglycans are highly polar and attract water. All of the GAGs except hyaluronan are covalently linked to one of approximately 30 different core proteins to form proteoglycans. The core protein is synthesized on the rough endoplasmic reticulum and transferred to the Golgi where nucleoside diphosphate-activated acidic and amino sugars are alternately added to the nonreducing end of the growing polysaccharide by glycosyltransferases, resulting in the characteristic repeating disaccharide structure common to the GAGs. Heparin/heparan sulfate (HS GAGs) and chondroitin sulfate/dermatan sulfate (CS GAGs) are synthesized in the Golgi apparatus, where protein cores made in the rough endoplasmic reticulum are posttranslationally modified with O-linked glycosylations by glycosyltransferases forming proteoglycans. Keratan sulfate may modify core proteins through N-linked glycosylation or O-linked glycosylation of the proteoglycan. The fourth class of GAG, hyaluronic acid, is not synthesized by the Golgi, but rather by integral membrane synthases which immediately secrete the dynamically elongated disaccharide chain. Degradation of proteoglycans during normal turnover of the extracellular matrix begins with proteolytic cleavage of the core protein by proteases in the extracellular matrix, which then enters the cell via endocytosis. The endosomes deliver their content to the lysosomes, where the proteolytic enzymes complete the degradation of the core proteins and an array of glycosidases and sulfatases hydrolyze the GAGs to monosaccharides. The lysosomes contain both endoglycosidases, which hydrolyze the long polymers into shorter oligosaccharides, and exoglycosidases that cleave individual acidic- or aminosugars from the GAG fragments. Lysosomal catabolism of GAGs proceeds in a stepwise manner from the non-reducing end (see FIG. 1). If the terminal sugar is sulfated, then the sulfate bond must be hydrolyzed by a specific sulfatase before the sugar can be removed. When the sulfate has been removed, a specific exoglycosidase then hydrolyzes the terminal sugar from the nonreducing end of the oligosaccharide, thus leaving it one sugar shorter. Degradation continues in this stepwise fashion, alternating between removal of sulfates by sulfatases and cleavage of the terminal sugars by exoglycosidases. If removal of a sulfate leaves a terminal glucosamine residue, then it must first be acetylated to N-acetylglucosamine because the lysosome lacks the enzyme required to remove glucosamine. This is accomplished by an acetyltransferase that uses acetyl-CoA as the acetyl group donor. When the glucosamine residue has been N-acetylated it can be hydrolyzed by α-N-acetylglucosaminidase, allowing the continuation of the stepwise degradation of the GAG. The terminal sugar of heparan sulfate and dermatan sulfate are sulfated, which is removed by the IDS enzyme (iduronate sulfatase). The next step is the removal of the terminal sugar, which is catalyzed by the IDUA enzyme. In subjects with MPS I, the defective IDUA enzyme is not able to remove that terminal sugar, leading to a build-up of heparan and dermatan.

The terms "subject" or "patient" are used interchangeably and refer to mammals such as human subjects and non-human primates, as well as experimental animals such as rabbits, dogs, cats, rats, mice, and other animals. Accordingly, the terms "subject" or "patient" as used herein means any mammalian subject to which the altered cells of the invention and/or proteins produced by the altered cells of the invention can be administered. Subjects of the present invention include those having MPS I disorder.

Generally, the subject is eligible for treatment for MPS I. For the purposes herein, such eligible subject is one who is experiencing, has experienced, or is likely to experience, one or more signs, symptoms or other indicators of MPS I; has been diagnosed with MPS I, whether, for example, newly diagnosed, and/or is at risk for developing MPS I. One suffering from or at risk for suffering from MPS I may optionally be identified as one who has been screened for elevated levels of GAG in tissues and/or urine.

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life.

As used herein, "delaying" or "slowing" the progression of MPS I means to prevent, defer, hinder, slow, retard, stabilize, and/or postpone development of the disease. This delay can be of varying lengths of time, depending on the history of the disease and/or individual being treated.

As used herein, "at the time of starting treatment" refers to the time period at or prior to the first exposure to an MPS I therapeutic composition such as the compositions of the invention. In some embodiments, "at the time of starting treatment" is about any of one year, nine months, six months, three months, second months, or one month prior to a MPS I drug. In some embodiments, "at the time of starting treatment" is immediately prior to coincidental with the first exposure to an MPS I therapeutic composition.

The term "wheelchair dependent" means a subject that is unable to walk through injury or illness and must rely on a wheelchair to move around.

The term "mechanical ventilator" describes a device that improves the exchange of air between a subject's lungs and the atmosphere.

As used herein, "based upon" includes (1) assessing, determining, or measuring the subject characteristics as described herein (and preferably selecting a subject suitable for receiving treatment; and (2) administering the treatment(s) as described herein.

A "symptom" of MPS I is any phenomenon or departure from the normal in structure, function, or sensation, experienced by the subject and indicative of MPS I.

"Severe MPS I" in subjects is characterized by delayed speech and developmental delay between 18 months to 3 years of age. The disease is characterized in severe MPS I subjects by organomegaly, hyperactivity and aggressiveness, neurologic deterioration, joint stiffness and skeletal deformities (including abnormal spinal bones), coarse facial features with enlarged tongue, heart valve thickening, hearing loss and hernias.

"Attenuated form MPS I" in subjects are typically diagnosed later than the severe subjects. The somatic clinical features are similar to the severe subjects, but overall disease severity in milder with, in general, slower disease progression with no or only mild cognitive impairment. Death in the untreated attenuated form is often between the ages of 20-30 years from cardiac and respiratory disease.

The term "supportive surgery" refers to surgical procedures that may be performed on a subject to alleviate symptoms that may be associated with a disease. For subjects with MPS I, such supportive surgeries may include heart valve replacement surgery, tonsillectomy and adenoidectomy, placement of ventilating tubes, repair of abdominal hernias, cervical decompression, treatment of carpal tunnel syndrome, surgical decompression of the median nerve, instrumented fusion (to stabilize and strengthen the spine), arthroscopy, hip or knee replacement, and correction of the lower limb axis, and tracheostomy (see Wraith et al. (2008) *Eur J Pediatr.* 167(3):267-277; and Scarpa et al. (2011) *Orphanet Journal of Rare Diseases,* 6:72).

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); nonsteroidal anti-inflammatory drugs (NSAIDUA); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, and dexamethasone; dihydrofolate reductase inhibitors such as methotrexate (oral or subcutaneous); hydroxycloroquine; sulfasalazine; leflunomide; cytokine or cytokine receptor antagonists including anti-interferon-alpha, -beta, or -gamma antibodies, anti-tumor necrosis factor-alpha antibodies (infliximab or adalimumab), anti-TNF-alpha immunoadhesin (etanercept), anti-tumor necrosis factor-beta antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (International Patent Publication No. WO 90/08187 published Jul. 26, 1990); streptokinase; TGF-beta; streptodornase; RNA or DNA from the host; FK506; RS-61443; deoxysperguahn; rapamycin; T-cell receptor (Cohen et al., U.S. Pat. No. 5,114,721); T-cell receptor fragments (Offner et al. (1991) *Science* 251:430-432; International Patent Publication No. WO 90/11294; Janeway (1989) *Nature* 341:482; and International Patent Publication No. WO 91/01133); and T cell receptor antibodies (EP 340,109) such as T10B9.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone, glucocorticoid and betamethasone.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

A "label" is used herein to refer to information customarily included with commercial packages of pharmaceutical formulations including containers such as vials and package inserts, as well as other types of packaging. Labels may also be of different colors.

It is to be understood that one, some, or all of the properties of the various embodiments described herein may be combined to form other embodiments of the present invention. These and other aspects of the invention will become apparent to one of skill in the art.

Nucleases

The methods described herein can make use of one or more nucleases for targeted introduction of the IDUA transgene. Non-limiting examples of nucleases include ZFNs, TALENs, homing endonucleases, CRISPR/Cas and/or Ttago guide RNAs, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding molecule (also referred to as a DNA-binding domain) and/or cleavage domain. For example, the DNA-binding domain of a naturally-occurring nuclease may be altered to bind to a selected target site (e.g., a ZFP, TALE and/or sgRNA of CRISPR/Cas that is engineered to bind to a selected target site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). In other embodiments, the nuclease comprises a system such as the CRISPR/Cas of Ttago system.

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" for example (LAGLIDADG" disclosed as SEQ ID NO: 39), see the DNA sequence for I-CreI below (Accession X01977, version x01977.1):

```
   1 gatccttgat caggacccctt gacagtttca ggtgggcagt
     ttatttgggg cgaatgcctc
  61 ctaaaaggta acggaggcgt gcaaaggttc cctcagtctg
     gacggaaatc agacattgag
 121 tgtaaaggca aaagggagct tgactgcaag acctacaagt
     cgagcagggg cgaaagaggc
 181 cttagtgatc cgacggtgcc gcgtggaagg gccgtcgctc
     aacggataaa agttactccc
 241 gggataacag gctgatcttc cccaagagtt cacatcgacg
     ggaaggtttg gcacctcgat
 301 gtcggctcat cacatcctcg gtctgtagta ggtccgaagg
     gttgggctgt tcgcccatta
 361 aagtggtacg tgagctgggt tcaaaacgta aataacactg
     cgtgtgcttg cagtaatgta
 421 agcaaagtat cggcttatat cggtgaaacc ttcctattgt
     tttaagtaca aactgtcgca
 481 taaaccacat tcgtgggcaa tagatggcaa cgccgaggga
     agaccatttc tttttggttt
 541 aataattcaa taaattaaat aaaacatctt atgaatacaa
     aatataataa agagttctta
 601 ctctacttag cagggtttgt agacggtgac ggtagcataa
     tcgctcaaat taagcctaat
 661 cagtcttata aatttaagca tcagctatca ctcgcgttcc
     aagtcacgca aaagacacag
 721 agacgttggt ttttagacaa attagtggat gaaattgggg
     ttggttatgt aagagatagg
 781 ggtagcgttt cggattatat tctaagcgaa atcaagcctt
     tgcataattt tttaacacaa
 841 ctacaacctt ttctaaaact aaaacaaaaa caagcaaatt
     tagttttaaa aattatttgg
 901 cggcttccgt cagcaaaaga atccccggac aaattcttag
     aagtttgtac atgggtggat
 961 caaattgcag ctctgaatga ttcgaagacg cgtaaaacaa
     cttctgaaac cgttcgtgct
1021 gtgctagaca gtttaagtga aaaaaagaaa tcgtccccgt
     agagacttta taaatttagc
1081 caatctctaa aagaatgttt acatacaatt tatttattgt
     tgctcgattt ataggatatt
1141 ttctcgagag tgggaaagta taatacgccg actcctgcca
     ttaacagtag caggatgaag
1201 acatagtcca tgcctttacg aaagtaaagg ggttagtttt
     aaagaccgca agttttattc
1261 ggctttaaaa tttcatgcgt gagacagttt ggtccatatc
     cggtgtaggc gttagagcat
1321 tgagagtagc cttcatagt acgagaggac ctgaaaggac
     atgccaattg tgtaccagtt
1381 ctcattccaa tgggaaacgc tgggtagcta cgcatggata
     gataactgct gaaagcatct
1441 aagtaggaag ctaaactcaa gatgagtgct ctctaaggcc
     gcggctagac aagccgttat
1501 ataggtatca ggtgtacagt cagcaatggc tttagccgag
     atatactaaa ggccgtttga
1561 ttttgacctt tataatataa ttacataacc ccttgcgggt
     aactatcgtt tatgagctaa
1621 gct
``` disclosed as SEQ ID NO:29), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J Mol. Biol.* 263:163-180; Argast et al. (1998) *J Mol. Biol.* 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996)*J Mol. Biol.* 263:163-180; Argast et al. (1998)*J Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 2007/0117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al. (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al. (1989) *Mol Gen Genet* 218:127-136 and International Patent Publication No. WO 2010/079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al. (2006) *J Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues (RVDs) at positions 12 and 13 with the identity of the contiguous nucleotides in the TAL-effector's target sequence (see Moscou and Bogdanove, (2009) *Science* 326:1501 and Boch et al. (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et al. (2010) *Genetics* epub 10.1534/genetics. 110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534, 261; 6,599,692; 6,503,717; 6,689,558; 7,030,215; 6,794, 136; 7,067,317; 7,262,054; 7,070,934; 7,361,635; 7,253, 273; and U.S. Patent Publication Nos. 2005/0064474; 2007/0218528; and 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 8,772,453; 6,479,626; 6,903,185; and 7,153,949 for exemplary linker sequences. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; and 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain of the nuclease is part of a CRISPR/Cas nuclease system, including, for example a single guide RNA (sgRNA). See, e.g., U.S. Pat. No. 8,697,359 and U.S. Patent Publication No. 2015/0056705. The CRISPR (clustered regularly interspaced short palindromic repeats) locus, which encodes RNA components of the system, and the Cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease, nickase and/or transcription factor systems.

In some embodiments, other Cas proteins may be used. Some exemplary Cas proteins include Cas9, Cpf1 (also known as Cas12a), C2c1, C2c2 (also known as Cas13a), C2c3, Cas1, Cas2, Cas4, CasX and CasY; and include engineered and natural variants thereof (Burstein et al. (2017) *Nature* 542:237-241) for example HF1/spCas9 (Kleinstiver et al. (2016) *Nature* 529:490-495; Cebrian-Serrano and Davies (2017) *Mamm Genome* 28(7):247-261); split Cas9 systems (Zetsche et al. (2015) *Nat Biotechnol* 33(2):139-142), trans-spliced Cas9 based on an intein-extein system (Troung et al. (2015) *Nucl Acid Res* 43(13):6450-8); mini-SaCas9 (Ma et al. (2018) *ACS Synth Biol* 7(4):978-985). Thus, in the methods and compositions described herein, it is understood that the term "Cas" includes all Cas variant proteins, both natural and engineered.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein. Additional non-limiting examples of RNA guided nucleases that may be used in addition to and/or instead of Cas proteins include Class 2 CRISPR proteins such as Cpf1. See, e.g., Zetsche et al. (2015) *Cell* 163:1-13.

In some embodiments, the DNA binding domain is part of a TtAgo system (see Swarts et al. (2014) *Nature* 507(7491): 258-261; Swarts et al. (2012) *PLoS One* 7(4):e35888; Sheng et al. (2014) *Proc. Natl. Acad. Sci. U.S.A.* 111(2):652-657). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al. (2005) *Mol. Cell* 19:405; Olovnikov et al. (2013) *Mol. Cell* 51:594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al., ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olovnikov et al., ibid).

Exogenous guide DNAs of arbitrary DNA sequence can be loaded onto the TtAgo protein (Swarts et al., ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. TtAgo-RNA-mediated DNA cleavage could be used to effect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

In certain embodiments the DNA-binding domains bind to albumin, e.g., DNA-binding domains of the ZFPs designated SBS-47171 and SBS-47898. See, e.g., U.S. Patent Publication No. 2015/0159172.

B. Cleavage Domains

Any suitable cleavage domain can be associated with (e.g., operatively linked) to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, U.S. Patent Publication Nos. 2003/0232410; 2005/0208489; 2005/0026157; 2005/0064474; 2006/0188987; 2006/0063231; and International Publication WO 07/014275. Likewise, TALE DNA-binding domains have been fused to nuclease domains to create TALENs. See, e.g., U.S. Pat. No. 8,586,526. CRISPR/Cas nuclease systems comprising single guide RNAs (sgRNAs) that bind to DNA and associate with cleavage domains (e.g., Cas domains) to induce targeted cleavage have also been described. See, e.g., U.S. Pat. Nos. 8,697,359 and 8,932,814 and U.S. Patent Publication No. 2015/0056705.

As noted above, the cleavage domain may be heterologous to the DNA-binding domain, for example a zinc finger DNA-binding domain and a cleavage domain from a nuclease or a TALEN DNA-binding domain and a cleavage domain from a nuclease; a sgRNA DNA-binding domain and a cleavage domain from a nuclease (CRISPR/Cas); and/or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,772,453; 8,623,618; 8,409,861; 8,034,598; 7,914,796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. U.S. Pat. Nos. 7,914, 796 and 8,034,598, the disclosures of which are incorporated by reference in their entireties. In certain embodiments, the engineered cleavage half-domain comprises mutations at positions 486, 499 and 496 (numbered relative to wild-type FokI), for instance mutations that replace the wild type Gln (Q) residue at position 486 with a Glu(E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. No. 8,772,453. In other embodiments, the engineered cleavage half domain comprises the "Sharkey" and/or "Sharkey mutations" (see Guo et al. (2010) *J Mol. Biol.* 400(1):96-107).

Engineered cleavage half-domains described herein can be prepared using any suitable method, for example, by site-directed mutagenesis of wild-type cleavage half-domains (FokI) as described in U.S. Pat. Nos. 7,888,121; 7,914,796; 8,034,598; and 8,623,618.

Alternatively, nucleases may be assembled in vivo at the nucleic acid target site using so-called "split-enzyme" technology (see, e.g. U.S. Patent Publication No. 2009/ 0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al. (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek et al. (2013) *Elife* 2:e00471. doi: 10.7554/eLife.00471; Jinek et al. (2012) *Science* 337: 816-821 and Cong, ibid).

The nuclease(s) as described herein may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

Thus, any nuclease comprising a DNA-binding domain and cleavage domain can be used. In certain embodiments, the nuclease comprises a ZFN made up of left and right ZFNs, for example a ZFN comprising a first ZFN comprising a ZFP designated SBS-47171 and a cleavage domain and a second ZFN comprising a ZFP designated SBS-47898 and a cleavage domain. In certain embodiments, the left and right (first and second) ZFNs of the ZFN are carried on the same vector and in other embodiments, the paired components of the ZFN are carried on different vectors, for example two AAV vectors, one designated SB-47171 AAV as shown in Table 1, SEQ ID NO:9 (an AAV2/6 vector carrying ZFN comprising the ZFP designated SBS-47171) and the other designated SB-47898 AAV as shown in Table 2, SEQ ID NO:12 (an AAV2/6 vector carrying ZFN comprising the ZFP designated SBS-47898).

Target Sites

As described in detail above, DNA domains can be engineered to bind to any sequence of choice in a locus, for example an albumin or other safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 2011/0301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237.

Selection of target sites; nucleases and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

In certain embodiments, the target site(s) for the DNA-binding domain(s) (is) are within an albumin gene. See, e.g., U.S. Patent Publication No. 2015/0159172.

Donors

As noted above, insertion of an exogenous sequence (also called a "donor sequence" or "donor"), for example for correction of a mutant gene or for increased expression of a gene encoding a protein lacking or deficient in MPS I disease (e.g., IDUA) is provided. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of a transgene encoding an IDUA protein for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Pat. Nos. 8,703,489 and 9,005,973. The donor sequence(s) can also be contained within a DNA MC, which may be introduced into the cell in circular or linear form. See, e.g., U.S. Patent Publication No. 2014/0335063. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., highly expressed, albumin, AAVS1, HPRT, etc.). However, it will be apparent that the donor may comprise a promoter and/or enhancer, for example a constitutive promoter or an inducible or tissue specific promoter. In some embodiments, the donor is maintained in the cell in an expression plasmid such that the gene is expressed extra-chromosomally.

The donor molecule may be inserted into an endogenous gene such that all, some or none of the endogenous gene is expressed. For example, a transgene as described herein may be inserted into an albumin or other locus such that some (N-terminal and/or C-terminal to the transgene encoding the lysosomal enzyme) or none of the endogenous albumin sequences are expressed, for example as a fusion with the transgene encoding the IDUA protein(s). In other embodiments, the transgene (e.g., with or without additional coding sequences such as for albumin) is integrated into any endogenous locus, for example a safe-harbor locus.

When endogenous sequences (endogenous or part of the transgene) are expressed with the transgene, the endogenous sequences (e.g., albumin, etc.) may be full-length sequences (wild-type or mutant) or partial sequences. Preferably the endogenous sequences are functional. Non-limiting examples of the function of these full length or partial sequences (e.g., albumin) include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the exogenous sequence (donor) comprises a fusion of a protein of interest and, as its fusion partner, an extracellular domain of a membrane protein, causing the fusion protein to be located on the surface of the cell. This allows the protein encoded by the transgene to potentially act in the serum. In the case of treatment for MPS I disease, IDUA enzyme encoded by the transgene fusion acts on the metabolic products that are accumulating in the serum from its location on the surface of the cell (e.g., RBC). In addition, if the RBC is engulfed by a splenic macrophage as is the normal course of degradation, the lysosome formed when the macrophage engulfs the cell would expose the membrane bound fusion protein to the high concentrations of metabolic products in the lysosome at the pH more naturally favorable to that enzyme.

In some cases, the donor may be an endogenous gene (IDUA) that has been modified. For instance, codon optimization may be performed on the endogenous gene to produce a donor. Furthermore, although antibody response to enzyme replacement therapy varies with respect to the specific therapeutic enzyme in question and with the individual subject, a significant immune response has been seen in many MPS I disease subjects being treated with enzyme replacement with wild-type IDUA. In addition, the relevance of these antibodies to the efficacy of treatment is also variable (see Katherine Ponder (2008) *J Clin Invest* 118(8): 2686). Thus, the methods and compositions of the current invention can comprise the generation of donor with modified sequences as compared to wild-type IDUA, including, but not limited to, modifications that produce functionally silent amino acid changes at sites known to be priming epitopes for endogenous immune responses, and/or truncations such that the polypeptide produced by such a donor is less immunogenic.

MPS I disease subjects often have neurological sequelae due the lack of the missing IDUA enzyme in the brain. Unfortunately, it is often difficult to deliver therapeutics to the brain via the blood due to the impermeability of the blood brain barrier. Thus, the methods and compositions of the invention may be used in conjunction with methods to increase the delivery of the therapeutic into the brain, including but not limited to methods that cause a transient opening of the tight junctions between cells of the brain capillaries such as transient osmotic disruption through the use of an intracarotid administration of a hypertonic mannitol solution, the use of focused ultrasound and the administration of a bradykinin analogue. Alternatively, therapeutics can be designed to utilize receptors or transport mechanisms for specific transport into the brain. Examples of specific receptors that may be used include the transferrin receptor, the insulin receptor or the low-density lipoprotein receptor related proteins 1 and 2 (LRP-1 and LRP-2). LRP is known to interact with a range of secreted proteins such as apoE, tPA, PAI-1 etc, and so fusing a recognition sequence from one of these proteins for LRP may facilitate transport of the enzyme into the brain, following expression in the liver of the therapeutic protein and secretion into the blood stream (see Gabathuler (2010) *Neurobiol Dis.* 37(1): 48-57).

In certain embodiments, the donor vectors is a vector as shown in SB-IDUA AAV (Table 5, SEQ ID NO:28).

Compositions/Systems of the Invention

The invention described herein utilizes three AAV vectors for practicing the method. Two vectors are used to deliver the right ZFN and the left ZFN and a third vector is used to provide the IDUA donor sequence (see Examples). In certain embodiments, the composition/systems comprising the 3 vectors which includes SB-47171 or SB-71557, SB-47898 or SB-71728 and SB-IDUA AAV.

Cells

Also provided herein are genetically modified cells, for example, liver cells or stem cells comprising a transgene encoding an IDUA protein, including cells produced by the methods described herein. The IDUA transgene may be expressed extra-chromosomally or can integrated in a targeted manner into the cell's genome using one or more nucleases. Unlike random integration, nuclease-mediated targeted integration ensures that the transgene is integrated into a specified gene. The transgene may be integrated anywhere in the target gene. In certain embodiments, the transgene is integrated at or near the nuclease binding and/or cleavage site, for example, within 1-300 (or any number of base pairs therebetween) base pairs upstream or downstream of the site of cleavage and/or binding site, more preferably within 1-100 base pairs (or any number of base pairs therebetween) of either side of the cleavage and/or binding site, even more preferably within 1 to 50 base pairs (or any number of base pairs therebetween) of either side of the cleavage and/or binding site. In certain embodiments, the integrated sequence does not include any vector sequences (e.g., viral vector sequences).

Any cell type can be genetically modified as described herein to comprise a transgene, including but not limited to cells or cell lines. Other non-limiting examples of genetically modified cells as described herein include T-cells (e.g., CD4+, CD3+, CD8+, etc.); dendritic cells; B-cells; autologous (e.g., subject-derived). In certain embodiments, the cells are liver cells and are modified in vivo. In certain embodiments, the cells are stem cells, including heterologous pluripotent, totipotent or multipotent stem cells (e.g., CD34+ cells, induced pluripotent stem cells (iPSCs), embryonic stem cells or the like). In certain embodiments, the cells as described herein are stem cells derived from subject.

The cells as described herein are useful in treating and/or preventing MPS I disease in a subject with the disorder, for example, by in vivo therapies. Ex vivo therapies are also provided, for example when the nuclease-modified cells can be expanded and then reintroduced into the subject using standard techniques. See, e.g., Tebas et al. (2014) *New Eng J Med* 370(10):901. In the case of stem cells, after infusion into the subject, in vivo differentiation of these precursors into cells expressing the functional protein (from the inserted donor) also occurs.

Pharmaceutical compositions (also referred to as "a formulation" or "article of manufacture" or "drug product" or "set of drug products") comprising one or more of the compositions (nucleases, IDUA donors, cells, etc.) as described herein are also provided. The pharmaceutical compositions may include the same or different types of component compositions in any concentrations. For example, provided herein is an article of manufacture comprising a set of drug products, which include three separate pharmaceutical compositions as follows: a first pharmaceutical composition comprising a purified AAV vector carrying one member of a ZFN pair (e.g., a left ZFN); a second pharmaceutical composition comprising a purified AAV vector carrying the other member of a ZFN pair (e.g., a right ZFN); and a third pharmaceutical composition comprising a purified AAV vector carrying an IDUA donor. The left ZFNs may comprise the ZFN designated 47171 (e.g., drug product designated SB-A6P-ZLEF) or the ZFN designated 71557 (e.g., drug product designated SB-A6P-ZL2) and the right ZFN may comprise the ZFN designated 47898 (e.g., drug product designated SB-A6P-ZRIGHT) or the ZFN designated 71728 (e.g., drug product designated SB-A6P-ZL2). One, two or three of the three pharmaceutical compositions may be individually formulated in phosphate buffered saline (PBS) containing CaCl2, MgCl2, NaCl, sucrose and a Poloxamer (e.g., Poloxamer P188) or in a Normal Saline (NS) formulation. Any concentration can be used, including but not limited to the concentrations shown in Table 6. Further, the article of manufacture may include any ratio of the three pharmaceutical compositions can be used, for example 1:1:8 (left ZFN:right ZFN:IDUA donor).

The pharmaceutical compositions (article of manufacture/set of drug products) are administered (e.g., intravenously) to a subject in need thereof such that IDUA is expressed in the subject, including at therapeutic levels (e.g., in plasma and/or blood leukocytes) for treatment of MPS I. The compositions may be administered separately or, preferably, the article of manufacture comprising a set of three drug products (ZFN1, ZFN2, and IDUA donor) are combined prior to administration, for example in an intravenous infusion bag. In addition, these formulations may be cryopreserved prior to administration to a subject.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger, TALEN and/or Cas protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada et al., in *Current Topics in Microbiology and Immunology* Doerfler and Bohm (eds.) (1995); and Yu et al. (1994) *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424 and WO 91/16024.

The preparation of lipid:nucleic acid complexes, including targeted liposomes such as immunolipid complexes, is well known to one of skill in the art (see, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been measured in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J. Virol.* 66:1635-1640; Sommerfelt et al. (1990) *Virol.* 176:58-59; Wilson et al. (1989) *J. Virol.* 63:2374-2378; Miller et al. (1991) *J. Virol.* 65:2220-2224; International Patent Publication No. WO 94/26877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin et al. (1984) *Mol. Cell. Biol.* 4:2072-2081; Hermonat & Muzyczka (1984) *PNAS* 81:6466-6470; and Samulski et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94(22):12133-12138). PA317/pLASN was the first therapeutic vector used in a gene therapy trial. (Blaese et al. (1995) *Science* 270:475-480). Transduction efficiencies of 50% or greater have been measured for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery system based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al. (1998) *Lancet* 351(9117): 1702-3; Kearns et al. (1996) *Gene Ther.* 9:748-55). Other AAV serotypes, including by non-limiting example, AAV1, AAV3, AAV4, AAV5, AAV6, AAV8, AAV 8.2, AAV9 and AAV rh10 and pseudotyped AAV such as AAV2/8, AAV2/5 and AAV2/6 can also be used in accordance with the present invention. In some embodiments, AAV serotypes that are capable of crossing the blood brain barrier are used.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24(1):5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual subject (e.g., lymphocytes, bone marrow aspirates, tissue biopsy) or universal donor hematopoietic stem cells, followed by reimplantation of the cells into a subject, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by an AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods of this invention contemplate the treatment and/or prevention of MPS I disease (e.g. a lysosomal storage disease). Treatment can comprise insertion of one or more corrective disease-associated genes (e.g., IDUA, etc.) into a safe harbor locus (e.g. albumin) in a cell for expression of the needed enzyme(s) and release into the blood stream. Once in the bloodstream, the secreted enzyme may be taken up by cells in the tissues, wherein the enzyme is then taken up by the lysosomes such that the GAGs are broken down. The transgene may encode a protein comprising a codon optimized transgene (e.g., IDUA); and/or a transgene in which epitopes may be removed without functionally altering the protein. In some cases, the methods comprise insertion of an episome expressing the corrective enzyme-encoding transgene into a cell for expression of the needed enzyme and release into the blood stream. Insertion into a secretory cell, such as a liver cell for release of the product into the blood stream, is particularly useful. The methods and compositions of the invention also can be used in any circumstance wherein it is desired to supply an IDUA transgene encoding one or more therapeutics in a hematopoietic stem cell such that mature cells (e.g., RBCs) derived from these cells contain the therapeutic. These stem cells can be differentiated in vitro or in vivo and may be derived from a universal donor type of cell which can be used for all subjects. Additionally, the cells may contain a transmembrane protein to traffic the cells in the body. Treatment can also comprise use of subject cells containing the therapeutic transgene where the cells are developed ex vivo and then introduced back into the subject. For example, HSC containing a suitable IDUA encoding transgene may be inserted into a subject via an autologous bone marrow transplant. Alternatively, stem cells such as muscle stem cells or iPSC which have been edited using with the IDUA encoding transgene may be also injected into muscle tissue.

Thus, this technology may be of use in a condition where a subject is deficient in some protein due to problems (e.g., problems in expression level or problems with the protein expressed as sub- or non-functioning). Particularly useful with this invention is the expression of transgenes to correct or restore functionality in subjects with MPS I disease.

By way of non-limiting examples, production of the defective or missing proteins accomplished and used to treat MPS I disease. Nucleic acid donors encoding the proteins may be inserted into a safe harbor locus (e.g. albumin or HPRT) and expressed either using an exogenous promoter or using the promoter present at the safe harbor. Alternatively, donors can be used to correct the defective gene in situ. The desired IDUA encoding transgene may be inserted into a CD34+ stem cell and returned to a subject during a bone marrow transplant. Finally, the nucleic acid donor may be be inserted into a CD34+ stem cell at a beta globin locus such that the mature red blood cell derived from this cell has a high concentration of the biologic encoded by the nucleic acid donor. The biologic-containing RBC can then be targeted to the correct tissue via transmembrane proteins (e.g. receptor or antibody). Additionally, the RBCs may be sensitized ex vivo via electrosensitization to make them more susceptible to disruption following exposure to an energy source (see International Patent Publication No. WO 2002/007752).

In some applications, an endogenous gene may be knocked out by use of the methods and compositions of the invention. Examples of this aspect include knocking out an aberrant gene regulator or an aberrant disease associated gene. In some applications, an aberrant endogenous gene may be replaced, either functionally or in situ, with a wild type version of the gene. The inserted gene may also be altered to improve the expression and/or functionality of the therapeutic IDUA protein or to reduce its immunogenicity. In some applications, the inserted IDUA encoding transgene is a fusion protein to increase its transport into a selected tissue such as the brain.

In some applications, provided herein is a method of improving or maintaining (slowing the decline) of functional ability in a human subject having MPS I as compared with a subject that has not been treated with the methods and compositions of the invention. In other applications, provided herein is a method of decreasing the need (dose level or frequency) for ERT in a subject with MPS I as compared with a subject that has not been treated with the methods and compositions of the invention. In yet another aspect, provided herein is a method of delaying the need for ERT initiation in a subject with MPS I as compared with a subject that has not been treated with the methods and compositions of the invention. In one aspect, provided herein is a method to delay, reduce or eliminate the need for supportive surgery in a subject with MPS I, comprising treating the subject with the compositions of the invention, as compared to a subject that has not received the compositions. In another aspect, provided herein is a method of delaying, reducing or preventing the need for a bone marrow transplant in a subject with MPS I as compared with a subject that has not been treated with the methods and compositions of the invention. In yet another aspect, provided herein is a method of improving the functional (delaying decline, maintenance) ability in a subject with MPS I by treating the subject with a standard dosing regimen of ERT in combination with treatment with the compositions as described herein as compared with a subject that has not been treated with the methods and compositions of the invention. In another aspect, provided herein is a method of suppressing disability progression in a human subject having MPS I as compared with a subject that has not been treated with the methods and compositions of the invention. In yet another aspect, provided herein is a method of delaying, reducing or preventing the need for the use of a medical ventilator device in a subject with MPS I as compared with a subject that has not been treated with the methods and compositions of the invention. In another aspect, provided herein is a method of delaying onset of confirmed disability progression or reducing the risk of confirmed disability progression in a human subject having MPS I as compared to a subject that that has not been treated with the methods and compositions of the invention. In one aspect of the invention, provided herein is a method of reducing, stabilizing or maintaining urine GAGs in a subject with MPS I, comprising treating the subject with the composition of the invention. In yet another aspect, provided herein is a method of extending life expectancy in a subject with MPS I as compared with a subject that has not been treated with the methods and compositions of the invention.

The following Examples relate to exemplary embodiments of the present disclosure in which the nuclease comprises a zinc finger nuclease (ZFN) or TALEN. It will be appreciated that this is for purposes of exemplification only and that other nucleases or nuclease systems can be used, for instance homing endonucleases (meganucleases) with engineered DNA-binding domains and/or fusions of naturally occurring of engineered homing endonucleases (meganucleases) DNA-binding domains and heterologous cleavage domains and/or a CRISPR/Cas system comprising an engineered single guide RNA.

EXAMPLES

Example 1

The preparation of polynucleotides and AAV vector comprising the polynucleotides is as follows: The AAV2/6 vector encoding the SB-47171 ZFN (left ZFN) comprises several structural features: the 5' and 3' ITRs of the AAV vector, the ApoE/hAAT hepatic control region and α1-anti-trypsin promoter, the human β-globin-IgG chimeric intron, the nuclear localization sequence, the ZFP 47171 ZFN binding domain, the FokI ELD nuclease domain, and a polyadenylation signal. The locations of the various elements are shown below in Table 1.

TABLE 1

Elements of SB-47171 AAV (SEQ ID NO: 9)

| Feature | Description | Position-annotation | SEQ ID NO |
|---|---|---|---|
| ITR | 5' inverted terminal repeat | 1-130- [plain text in brackets] | 1 |
| ApoE/ hAAT | ApoE Hepatic Control Region & α1-antitrypsin promoter | 141-863- underlined | 2 |
| Chimeric Intron | Human β globin- IgG chimeric intron | 867-999- *italics* | 3 |
| NLS | NLS | 1016-1036- double underline | 4 |

TABLE 1-continued

Elements of SB-47171 AAV (SEQ ID NO: 9)

| Feature | Description | Position-annotation | SEQ ID NO |
|---|---|---|---|
| 47171 | ZFP 47171 DNA-binding domain | 1055-1486- Bold | 5 |
| FokI-ELD | FokI-ELD nuclease domain | 1493-2092- lower case | 6 |
| poly A | Polyadenylation signal | 2148-2370- dashed underline | 7 |

TABLE 1-continued

Elements of SB-47171 AAV (SEQ ID NO: 9)

| Feature | Description | Position-annotation | SEQ ID NO |
|---|---|---|---|
| ITR | 3' inverted terminal repeat | 2422-2529- wavy underline | 8 |

The complete nucleotide sequence for the SB-47171 AAV2/6 vector is shown below. The specific annotations shown in Table 1 are indicated in the sequence text as shown in Table 1:

```
                                                          (SEQ ID NO: 9)
    [CTGCGCGCTC GCTCGCTCAC TGAGGCCGCC CGGGCAAAGC CCGGGCGTCG     50

GGCGACCTTT GGTCGCCCGG CCTCAGTGAG CGAGCGAGCG CGCAGAGAGG    100

GAGTGGCCAA CTCCATCACT AGGGGTTCCT]GCGGCCTAGT AGGCTCAGAG    150

GCACACAGGA GTTTCTGGGC TCACCCTGCC CCCTTCCAAC CCCTCAGTTC    200

CCATCCTCCA GCAGCTGTTT GTGTGCTGCC TCTGAAGTCC ACACTGAACA    250

AACTTCAGCC TACTCATGTC CCTAAAATGG GCAAACATTG CAAGCAGCAA    300

ACAGCAAACA CACAGCCCTC CCTGCCTGCT GACCTTGAG CTGGGGCAGA     350

GGTCAGAGAC CTCTCTGGGC CCATGCCACC TCCAACATCC ACTCGACCCC    400

TTGGAATTTC GGTGGAGAGG AGCAGAGGTT GTCCTGGCGT GGTTTAGGTA    450

GTGTGAGAGG GGTACCCGGG GATCTTGCTA CCAGTGGAAC AGCCACTAAG    500

GATTCTGCAG TGAGAGCAGA GGGCCAGCTA AGTGGTACTC TCCCAGAGAC    550

TGTCTGACTC ACGCCACCCC CTCCACCTTG GACACAGGAC GCTGTGGTTT    600

CTGAGCCAGG TACAATGACT CCTTTCGGTA AGTGCAGTGG AAGCTGTACA    650

CTGCCCAGGC AAAGCGTCCG GGCAGCGTAG GCGGGCGACT CAGATCCCAG    700

CCAGTGGACT TAGCCCCTGT TTGCTCCTCC GATAACTGGG GTGACCTTGG    750

TTAATATTCA CCAGCAGCCT CCCCCGTTGC CCCTCTGGAT CCACTGCTTA    800

AATACGGACG AGGACAGGGC CCTGTCTCCT CAGCTTCAGG CACCACCACT    850

GACCTGGGAC AGTCAGGTAA GTATCAAGGT TACAAGACAG GTTTAAGGAG    900

ACCAATAGAA ACTGGGCTTG TCGAGACAGA GAAGACTCTT GCGTTTCTGA    950

TAGGCACCTA TTGGTCTTAC TGACATCCAC TTTGCCTTTC TCTCCACAGG   1000

CAATTCGCCA TGGCCCCCAA GAAGAAGAGG AAGGTGGGCA TCCACGGGGT   1050

ACCGGCCGCA ATGGCAGAAC GGCCCTTCCA GTGCCGCATC TGCATGCGCA   1100

ACTTCAGCCA GTCGGGCAAC CTGTCCCGCC ACATCCGGAC TCATACCGGC   1150

GAAAAACCAT TCGCTTGTGA CATCTGCGGA AGAAAGTTTG CGCTGAAGCA   1200

GAACCTCTGC ATGCATACCA AGATTCACAC CGGAGAGAAG CCGTTTCAGT   1250

GTCGCATTTG CATGAGAAAG TTCGCCTGGG CCGATAACCT TCAGAATCAC   1300

ACCAAGATCC ACACCGGGGA AAAGCCGTTC CAGTGCCGGA TCTGCATGAG   1350

GAACTTCTCA ACGTCCGGAA ACCTGACCAG GCATATCCGG ACCCACACTG   1400

GGGAGAAGCC TTTCGCCTGC GACATTTGCG GTCGGAAGTT CGCCCGGCAA   1450

TCCCACTTGT GTCTCCACAC TAAGATCCAC CTGAGAGGAT CCcagctggt   1500
gaagagcgag ctggaggaga agaagtccga gctgcggcac aagctgaagt   1550
```

```
-continued
acgtgcccca cgagtacatc gagctgatcg agatcgccag aacagcacc    1600 caggaccgca tcctggagat gaaggtgatg gagttcttca tgaaggtgta    1650
cggctacagg ggaaagcacc tgggcggaag cagaaagcct gacggcgcca    1700
tctatacagt gggcagcccc atcgattacg gcgtgatcgt ggacacaaag    1750
gcctacagcg gcggctacaa tctgcctatc ggccaggccg acgagatgga    1800
gagatacgtg gaggagaacc agacccggga taagcacctc aaccccaacg    1850
agtggtggaa ggtgtaccct agcagcgtga ccgagttcaa gttcctgttc    1900
gtgagcggcc acttcaaggg caactacaag gcccagctga ccaggctgaa    1950
ccacatcacc aactgcaatg gcgccgtgct gagcgtggag gagctgctga    2000
tcggcggcga gatgatcaaa gccggcaccc tgacactgga ggaggtgcgg    2050
cgcaagttca acaacggcga gatcaacttc agatcttgat aaCTCGAGTC    2100

TAGAGGATCT CGAGCCGAAT TCCTGCAGCC CGGGGGATCA GCCTCGA̱C̱ṮG̱    2150

ṮG̱C̱C̱ṮṮC̱ṮA̱G̱ ṮṮG̱C̱C̱A̱G̱C̱C̱A̱ ṮC̱ṮG̱ṮṮG̱ṮṮṮ G̱C̱C̱C̱C̱ṮC̱C̱C̱C̱ C̱G̱ṮG̱C̱C̱ṮṮC̱C̱    2200

ṮṮG̱A̱C̱C̱C̱ṮG̱G̱ A̱A̱G̱G̱ṮG̱C̱C̱A̱C̱ ṮC̱C̱C̱A̱C̱ṮG̱ṮC̱ C̱ṮṮṮC̱C̱ṮA̱A̱Ṯ A̱A̱A̱A̱ṮG̱A̱G̱G̱A̱    2250

A̱A̱ṮṮG̱C̱A̱ṮC̱G̱ C̱A̱ṮṮG̱ṮC̱ṮG̱A̱ G̱ṮA̱G̱G̱ṮG̱ṮC̱A̱ ṮṮC̱ṮA̱ṮṮC̱ṮG̱ G̱G̱G̱G̱G̱ṮG̱G̱G̱G̱    2300

ṮG̱G̱G̱G̱C̱A̱G̱G̱A̱ C̱A̱G̱C̱A̱A̱G̱G̱G̱G̱ G̱A̱G̱G̱A̱ṮṮG̱G̱G̱ A̱A̱G̱A̱C̱A̱A̱ṮA̱G̱ C̱A̱G̱G̱C̱A̱ṮG̱C̱Ṯ    2350

G̱G̱G̱G̱A̱ṮG̱C̱G̱G̱ ṮG̱G̱G̱C̱ṮC̱ṮA̱Ṯ GGCTTCTGAG GCGGAAAGAA CCAGCTGGGG    2400

CTCGAGATCC ACTAGGGCCG CAGGAACCCC TAGTGATGGA GTTGGCCACT    2450

CCCTCTCTGC GCGCTCGCTC GCTCACTGAG GCCGCCCGGG CTTTGCCCGG    2500

GCGGCCTCAG TGAGCGAGCG AGCGCGCAG    2529
```

The AAV2/6 vector comprising SB-47898 similarly comprises several features, and these are shown below in Table 2.

TABLE 2

Elements of SB-47898 AAV (SEQ ID NO: 12)

| Feature | Description | Position- annotation | SEQ ID NO: |
|---|---|---|---|
| ITR | 5' inverted terminal repeat | 1-130- [plain text in brackets] | 1 |
| ApoE/hAAT | ApoE Hepatic Control Region & α1-antitrypsin promoter | 141-863 underlined | 2 |
| Chimeric Intron | Human β globin- IgG chimeric intron | 867-999 italics | 3 |
| NLS | NLS | 1016-1036 double underline | 4 |
| 47898 | ZFP 47898 DNA-binding domain | 1055-1570 Bold | 10 |
| FokI-KKR | FokI-KKR nuclease domain | 1577-2170 lower case | 11 |
| poly A | Polyadenylation signal | 2226-2448 dashed underline | 7 |
| ITR | 3' inverted terminal repeat | 2500-2607 wavy underline | 8 |

The complete nucleotide sequence for the SB-47898 AAV2/6 vector is shown below. The specific annotations shown in Table 2 are indicated in the sequence text as shown in Table 2.

```
                                                    (SEQ ID NO: 12)
[CTGCGCGCTC GCTCGCTCAC TGAGGCCGCC CGGGCAAAGC CCGGGCGTCG     50

GGCGACCTTT GGTCGCCCGG CCTCAGTGAG CGAGCGAGCG CGCAGAGAGG    100

GAGTGGCCAA CTCCATCACT AGGGGTTCCT]GCGGCCTAGT AGGCTCAGAG    150

GCACACAGGA GTTTCTGGGC TCACCCTGCC CCCTTCCAAC CCCTCAGTTC    200
```

| | |
|---|---|
| CCATCCTCCA GCAGCTGTTT GTGTGCTGCC TCTGAAGTCC ACACTGAACA | 250 |
| AACTTCAGCC TACTCATGTC CCTAAAATGG GCAAACATTG CAAGCAGCAA | 300 |
| ACAGCAAACA CACAGCCCTC CCTGCCTGCT GACCTTGGAG CTGGGGCAGA | 350 |
| GGTCAGAGAC CTCTCTGGGC CCATGCCACC TCCAACATCC ACTCGACCCC | 400 |
| TTGGAATTTC GGTGGAGAGG AGCAGAGGTT GTCCTGGCGT GGTTTAGGTA | 450 |
| GTGTGAGAGG GGTACCCGGG GATCTTGCTA CCAGTGGAAC AGCCACTAAG | 500 |
| GATTCTGCAG TGAGAGCAGA GGGCCAGCTA AGTGGTACTC TCCCAGAGAC | 550 |
| TGTCTGACTC ACGCCACCCC CTCCACCTTG GACACAGGAG GCTGTGGTTT | 600 |
| CTGAGCCAGG TACAATGACT CCTTTCGGTA AGTGCAGTGG AAGCTGTACA | 650 |
| CTGCCCAGGC AAAGCGTCCG GGCAGCGTAG GCGGGCGACT CAGATCCCAG | 700 |
| CCAGTGGACT TAGCCCCTGT TTGCTCCTCC GATAACTGGG GTGACCTTGG | 750 |
| TTAATATTCA CCAGCAGCCT CCCCCGTTGC CCCTCTGGAT CCACTGCTTA | 800 |
| AATACGGACG AGGACAGGGC CCTGTCTCCT CAGCTTCAGG CACCACCACT | 850 |
| GACCTGGGAC AGTCAGGTAA *GTATCAAGGT TACAAGACAG GTTTAAGGAG* | 900 |
| *ACCAATAGAA ACTGGGCTTG TCGAGACAGA GAAGACTCTT GCGTTTCTGA* | 950 |
| *TAGGCACCTA TTGGTCTTAC TGACATCCAC TTTGCCTTTC TCTCCACAGG* | 1000 |
| CAATTCGCCA TGGCCCCCAA GAAGAAGAGG AAGGTGGGCA TCCACGGGGT | 1050 |
| ACCGGCCGCA ATGGCAGAGA GGCCCTTTCA GTGCCGGATC TGCATGCGGA | 1100 |
| ACTTCTCCAC CCCACAACTT CTGGACCGAC ATATCCGCAC CCATACCGGG | 1150 |
| GAAAAGCCTT TCGCGTGCGA CATTTGCGGA CGGAAATTCG CGTTGAAGCA | 1200 |
| CAATCTCCTG ACCCACACTA AGATTCATAC TGGCGAAAAG CCGTTCCAGT | 1250 |
| GCCGCATCTG TATGAGGAAC TTCAGCGATC AGTCGAACCT GAACGCCCAC | 1300 |
| ATTCGGACTC ATACCGGAGA AAAGCCCTTT GCCTGCGATA TCTGCGGTCG | 1350 |
| CAAGTTCGCT AGGAACTTCT CACTGACCAT GCACACCAAA ATCCACACTG | 1400 |
| GAGAGCGGGG ATTCCAGTGT AGAATCTGTA TGCGCAACTT CTCCCTGCGG | 1450 |
| CACGACCTGG ACCGCCACAT CAGAACCCAC ACCGGGGAGA AGCCGTTCGC | 1500 |
| CTGCGACATC TGCGGCCGGA AGTTCGCCCA CCGGTCCAAC CTGAACAAGC | 1550 |
| ACACGAAGAT TCACCTCCGC GGATCCcagc tggtgaagag cgagctggag | 1600 |
| gagaagaagt ccgagctgcg gcacaagctg aagtacgtgc cccacgagta | 1650 |
| catcgagctg atcgagatcg ccaggaacag cacccaggac cgcatcctgg | 1700 |
| agatgaaggt gatggagttc ttcatgaagg tgtacggcta cagggaaag | 1750 |
| cacctgggcg gaagcagaaa gcctgacggc gccatctata cagtgggcag | 1800 |
| ccccatcgat tacggcgtga tcgtggacac aaaggcctac agcggcggct | 1850 |
| acaatctgcc tatcggccag gccgacgaga tgcagagata cgtgaaggag | 1900 |
| aaccagaccc ggaataagca catcaacccc aacgagtggt ggaaggtgta | 1950 |
| ccctagcagc gtgaccgagt tcaagttcct gttcgtgagc ggccacttca | 2000 |
| agggcaacta caaggcccag ctgaccaggc tgaaccgcaa aaccaactgc | 2050 |
| aatggcgccg tgctgagcgt ggaggagctg ctgatcggcg gcgagatgat | 2100 |
| caaagccggc acccctgacac tggaggaggt gcggcgcaag ttcaacaacg | 2150 |
| gcgagatcaa cttctgataa CTCGAGTCTA GAGGATCTCG AGCCGAATTC | 2200 |

-continued

```
CTGCAGCCCG GGGGATCAGC CTCGACTGTG CCTTCTAGTT GCCAGCCATC    2250

TGTTGTTTGC CCCTCCCCCG TGCCTTCCTT GACCCTGGAA GGTGCCACTC    2300

CCACTGTCCT TTCCTAATAA AATGAGGAAA TTGCATCGCA TTGTCTGAGT    2350

AGGTGTCATT CTATTCTGGG GGGTGGGGTG GGGCAGGACA GCAAGGGGGA    2400

GGATTGGGAA GACAATAGCA GGCATGCTGG GGATGCGGTG GGCTCTATGG    2450

CTTCTGAGGC GGAAAGAACC AGCTGGGGCT CGAGATCCAC TAGGGCCGCA    2500

GGAACCCCTA GTGATGGAGT TGGCCACTCC CTCTCTGCGC GCTCGCTCGC    2550

TCACTGAGGC CGCCCGGGCT TTGCCCGGGC GGCCTCAGTG AGCGAGCGAG    2600

CGCGCAG                                                   2607
```

The AAV2/6 vector comprising SB-71557 similarly comprises several features, and these are shown below in Table 3.

TABLE 3

Elements of SB-71557 AAV (SEQ ID NO: 23)

| Nucleotide Position-annotation | Feature/Description | SEQ ID NO: | Sequence |
| --- | --- | --- | --- |
| 1-130 | 5' ITR [plain text in brackets] | 1 | CTGCGCGCTCGCTCGCTCACTGAGGCCGCCCGGGCAAAGCCCGGG CGTCGGGCGACCTTTGGTCGCCCGGCCTCAGTGAGCGAGCGAGCG CGCAGAGAGGGAGTGGCCAACTCCATCACTAGGGGTTCCT |
| 156-476 | ApoE (Enhancer) underlined | 15 | AGGCTCAGAGGCACACAGGAGTTTCTGGGCTCACCCTGCCCCCTT CCAACCCCTCAGTTCCCATCCTCCAGCAGCTGTTTGTGTGCTGCC TCTGAAGTCCACACTGAACAAACTTCAGCCTACTCATGTCCCTAA AATGGGCAAACATTGCAAGCAGCAAACAGCAAACACACAGCCCTC CCTGCCTGCTGACCTTGGAGCTGGGGCAGAGGTCAGAGACCTCTC TGGGCCCATGCCACCTCCAACATCCACTCGACCCCTTGGAATTTC GGTGGAGAGGAGCAGAGGTTGTCCTGGCGTGGTTTAGGTAGTGTG AGAGGG |
| 485-877 | hAAT (Promoter) *italics* | 17 | GATCTTGCTACCAGTGGAACAGCCACTAAGGATTCTGCAGTGAGA GCAGAGGGCCAGCTAAGTGGTACTCTCCCAGAGACTGTCTGACTC ACGCCACCCCCTCCACCTTGGACACAGGACGCTGTGGTTTCTGAG CCAGGTACAATGACTCCTTTCGGTAAGTGCAGTGGAAGCTGTACA CTGCCCAGGCAAAGCGTCCGGGCAGCGTAGGCGGGCGACTCAGAT CCCAGCCAGTGGACTTAGCCCCTGTTTGCTCCTCCGATAACTGGG GTGACCTTGGTTAATATTCACCAGCAGCCTCCCCCGTTGCCCCTC TGGATCCACTGCTTAAATACGGACGAGGACAGGGCCCTGTCTCCT CAGCTTCAGGCACCACCACTGACCTGGGACAGT |
| 886-933 | 5' UTR Bold | 18 | CTTGTTCTTTTTGCAGAAGCTCAGAATAAACGCTCAACTTTGGCA GAT |
| 943-1075 | Human β globin/IgG chimeric intron | 3 | GTAAGTATCAAGGTTACAAGACAGGTTTAAGGAGACCAATAGAAA CTGGGCTTGTCGAGACAGAGAAGACTCTTGCGTTTCTGATAGGCA CCTATTGGTCTTACTGACATCCACTTTGCCTTTCTCTCCACAG |
| 1089-1154 | N-terminal peptide | 19 | GACTACAAAGACCATGACGGTGATTATAAAGATCATGACATCGAT TACAAGGATGACGATGACAAG |
| 1161-1181 | Nuclear localization signal *Bold italic* | 4 | CCCAAGAAGAAGAGGAAGGTC |

TABLE 3-continued

Elements of SB-71557 AAV (SEQ ID NO: 23)

| Nucleotide Position-annotation | Feature/Description | SEQ ID NO: | Sequence |
|---|---|---|---|
| 1200-1631 | ZFP 71557 DNA-binding domain lower case | 20 | GCCGCTATGGCTGAGAGGCCCTTCCAGTGTCGAATCTGCATGCAG AACTTCAGTCAGTCCGGCAACCTGGCCCGCCACATCCGCACCCAC ACCGGCGAGAAGCCTTTTGCCTGTGACATTTGTGGGAGGAAATTT GCCCTGAAGCAGAACCTGTGTATGCATACCAAGATACACACGGGC GAGAAGCCCTTCCAGTGTCGAATCTGCATGCAGAAGTTTGCCTGG CAGTCCAACCTGCAGAACCATACCAAGATACACACGGGCGAGAAG CCCTTCCAGTGTCGAATCTGCATGCGTAACTTCAGTACCTCCGGC AACCTGACCCGCCACATCCGCACCCACACCGGCGAGAAGCCTTTT GCCTGTGACATTTGTGGGAGGAAATTTGCCCGCCGCTCCCACCTG ACCTCCCATACCAAGATACACCTGCGG |
| 1638-2237 | FokI-ELD nuclease domain N542D <u>Dashed underline</u> | 21 | CAGCTGGTGAAGAGCGAGCTGGAGGAGAAGAAGTCCGAGCTGCGG CACAAGCTGAAGTACGTGCCCCACGAGTACATCGAGCTGATCGAG ATCGCCAGGAACAGCACCCAGGACCGCATCCTGGAGATGAAGGTG ATGGAGTTCTTCATGAAGGTGTACGGCTACAGGGGAAAGCACCTG GGCGGAAGCAGAAAGCCTGACGGCGCCATCTATACAGTGGGCAGC CCCATCGATTACGGCGTGATCGTGGACACAAAGGCCTACAGCGGC GGCTACAATCTGCCTATCGGCCAGGCCGACGAGATGGAGAGATAC GTGGAGGAGAACCAGACCCGGGATAAGCACCTCAACCCCAACGAG TGGTGGAAGGTGTACCCTAGCAGCGTGACCGAGTTCAAGTTCCTG TTCGTGAGCGGCCACTTCAAGGGCAACTACAAGGCCCAGCTGACC AGGCTGAACCACATCACCAACTGCGACGGCGCCGTGCTGAGCGTG GAGGAGCTGCTGATCGGCGGCGAGATGATCAAAGCCGGCACCCTG ACACTGGAGGAGGTGCGGCGCAAGTTCAACAACGGCGAGATCAAC TTCAGATCTTGATAA |
| 2250-2841 | WPREmut6 3'UTR <u>Dotted underline</u> | 22 | AATCAACCTCTGGATTACAAAATTTGTGAAAGATTGACTGATATT CTTAACTATGTTGCTCCTTTTACGCTGTGTGGATATGCTGCTTTA ATGCCTCTGTATCATGCTATTGCTTCCCGTACGGCTTTCGTTTTC TCCTCCTTGTATAAATCCTGGTTGCTGTCTCTTTATGAGGAGTTG TGGCCCGTTGTCCGTCAACGTGGCGTGGTGTGCTCTGTGTTTGCT GACGCAACCCCCACTGGCTGGGCATTGCCACCACCTGTCAACTC CTTTCTGGGACTTTCGCTTTCCCCCTCCCGATCGCCACGGCAGAA CTCATCGCCGCCTGCCTTGCCCGCTGCTGGACAGGGGCTAGGTTG CTGGGCACTGATAATTCCGTGGTGTTGTCGGGGAAATCATCGTCC TTTCCTTGGCTGCTCGCCTGTGTTGCCAACTGGATCCTGCGCGGG ACGTCCTTCTGCTACGTCCCTTCGGCTCTCAATCCAGCGGACCTC CCTTCCCGAGGCCTTCTGCCGGTTCTGCGGCCTCTCCCGCGTCTT CGCTTTCGGCCTCCGACGAGTCGGATCTCCCTTTGGGCCGCCTCC CCGCCTG |
| 2848-3070 | <u>Polyadenylation signal</u> | 7 | CTGTGCCTTCTAGTTGCCAGCCATCTGTTGTTTGCCCCTCCCCCG TGCCTTCCTTGACCCTGGAAGGTGCCACTCCCACTGTCCTTTCCT AATAAAATGAGGAAATTGCATCGCATTGTCTGAGTAGGTGTCATT CTATTCTGGGGGGTGGGGTGGGGCAGGACAGCAAGGGGGAGGATT GGGAAGACAATAGCAGGCATGCTGGGGATGCGGTGGGCTCTAT |
| 3088-3195 | 3' ITR [Bold text in brackets] | 8 | AGGAACCCCTAGTGATGGAGTTGGCCACTCCCTCTCTGCGCGCTC GCTCGCTCACTGAGGCCGCCCGGGCTTTGCCCGGGCGGCCTCAGT GAGCGAGCGAGCGCGCAG |

Sequence of 71557 AAV:

(SEQ ID NO: 23)

```
[CTGCGCGCTC GCTCGCTCAC TGAGGCCGCC CGGGCAAAGC CCGGGCGTCG        50

GGCGACCTTT GGTCGCCCGG CCTCAGTGAG CGAGCGAGCG CGCAGAGAGG       100

GAGTGGCCAA CTCCATCACT AGGGGTTCCT] GCGGCCTAAG CTTGAGCTCT       150

TCGAAAGGCT CAGAGGCACA CAGGAGTTTC TGGGCTCACC CTGCCCCCTT       200

CCAACCCCTC AGTTCCCATC CTCCAGCAGC TGTTTGTGTG CTGCCTCTGA       250

AGTCCACACT GAACAAACTT CAGCCTACTC ATGTCCCTAA AATGGGCAAA       300

CATTGCAAGC AGCAAACAGC AAACACACAG CCCTCCCTGC CTGCTGACCT       350

TGGAGCTGGG GCAGAGGTCA GAGACCTCTC TGGGCCCATG CCACCTCCAA       400

CATCCACTCG ACCCCTTGGA ATTTCGGTGG AGAGGAGCAG AGGTTGTCCT       450

GGCGTGGTTT AGGTAGTGTG AGAGGGGTCC CGGGGATCTT GCTACCAGTG       500

GAACAGCCAC TAAGGATTCT GCAGTGAGAG CAGAGGGCCA GCTAAGTGGT       550
```

TABLE 3-continued

Elements of SB-71557 AAV (SEQ ID NO: 23)

| Nucleotide Position-annotation | Feature/Description | SEQ ID NO: | Sequence | |
|---|---|---|---|---|
| | | | *ACTCTCCCAG AGACTGTCTG ACTCACGCCA CCCCCTCCAC CTTGGACACA* | 600 |
| | | | *GGACGCTGTG GTTTCTGAGC CAGGTACAAT GACTCCTTTC GGTAAGTGCA* | 650 |
| | | | *GTGGAAGCTG TACACTGCCC AGGCAAAGCG TCCGGGCAGC GTAGGCGGGC* | 700 |
| | | | *GACTCAGATC CCAGCCAGTG GACTTAGCCC CTGTTTGCTC CTCCGATAAC* | 750 |
| | | | *TGGGGTGACC TTGGTTAATA TTCACCAGCA GCCTCCCCCG TTGCCCCTCT* | 800 |
| | | | *GGATCCACTG CTTAAATACG GACGAGGACA GGGCCCTGTC TCCTCAGCTT* | 850 |
| | | | *CAGGCACCAC CACTGACCTG GGACAGTCCT AGGTG*CTTGT TCTTTTTGCA | 900 |
| | | | GAAGCTCAGA ATAAACGCTC AACTTTGGCA GATACTAGTC AG<u>GTAAGTAT</u> | 950 |
| | | | <u>CAAGGTTACA AGACAGGTTT AAGGAGACCA ATAGAAACTG GCTTGTCGA</u> | 1000 |
| | | | <u>GACAGAGAAG ACTCTTGCGT TTCTGATAGG CACCTATTGG TCTTACTGAC</u> | 1050 |
| | | | <u>ATCCACTTTG CCTTTCTCTC</u> CACAGGACCG GTGCCATGGA CTACAAAGAC | 1100 |
| | | | CATGACGGTG ATTATAAAGA TCATGACATC GATTACAAGG ATGACGATGA | 1150 |
| | | | CAAGATGGCC *CCCAAGAAGA AGAGGAAGGT C*GGCATTCAT GGGGTACCCg | 1200 |
| | | | ccgctatggc tgagaggccc ttccagtgtc gaatctgcat gcagaacttc | 1250 |
| | | | agtcagtccg gcaacctggc cgccacatc cgcacccaca ccggcgagaa | 1300 |
| | | | gccttttgcc tgtgacattt gtgggaggaa atttgccctg aagcagaacc | 1350 |
| | | | tgtgtatgca taccaagata cacacgggcg agaagccctt ccagtgtcga | 1400 |
| | | | atctgcatgc agaagtttgc ctggcagtcc aacctgcaga accataccaa | 1450 |
| | | | gatacacacg gcgagaagc ccttccagtg tcgaatctgc atgcgtaact | 1500 |
| | | | tcagtaccte cggcaacctg acccgccaca tccgcaccca caccggcgag | 1550 |
| | | | aagccttttg cctgtgacat tgtgggagg aaatttgccc gccgctccca | 1600 |
| | | | cctgacctcc cataccaaga tacacctgcg g<u>GGATCCCAG CTGGTGAAGA</u> | 1650 |
| | | | <u>GCGAGCTGGA GGAGAAGAAG TCCGAGCTGC GGCACAAGCT GAAGTACGTG</u> | 1700 |
| | | | <u>CCCCACGAGT ACATCGAGCT GATCGAGATC GCCAGGAACA GCACCCAGGA</u> | 1750 |
| | | | <u>CCGCATCCTG GAGATGAAGG TGATGGAGTT CTTCATGAAG GTGTACGGCT</u> | 1800 |
| | | | <u>ACAGGGGAAA GCACCTGGGC GGAAGCAGAA AGCCTGACGG CGCCATCTAT</u> | 1850 |
| | | | <u>ACAGTGGGCA GCCCCATCGA TTACGGCGTG ATCGTGGACA CAAAGGCCTA</u> | 1900 |
| | | | <u>CAGCGGCGGC TACAATCTGC CTATCGGCCA GGCCGACGAG ATGGAGAGAT</u> | 1950 |
| | | | <u>ACGTGGAGGA GAACCAGACC CGGGATAAGC ACCTCAACCC CAACGAGTGG</u> | 2000 |
| | | | <u>TGGAAGGTGT ACCCTAGCAG CGTGACCGAG TTCAAGTTCC TGTTCGTGAG</u> | 2050 |
| | | | <u>CGGCCACTTC AAGGGCAACT ACAAGGCCCA GCTGACCAGG CTGAACCACA</u> | 2100 |

TABLE 3-continued

Elements of SB-71557 AAV (SEQ ID NO: 23)

| Nucleotide Position-annotation | Feature/Description | SEQ ID NO: | Sequence | |
|---|---|---|---|---|
| | | | TCACCAACTG CGACGGCGCC GTGCTGAGCG TGGAGGAGCT GCTGATCGGC | 2150 |
| | | | GGCGAGATGA TCAAAGCCGG CACCCTGACA CTGGAGGAGG TGCGGCGCAA | 2200 |
| | | | GTTCAACAAC GGCGAGATCA ACTTCAGATC TTGATAACTC GAGTCTAGAA | 2250 |
| | | | ATCAACCTCT GGATTACAAA ATTTGTGAAA GATTGACTGA TATTCTTAAC | 2300 |
| | | | TATGTTGCTC CTTTTACGCT GTGTGGATAT GCTGCTTTAA TGCCTCTGTA | 2350 |
| | | | TCATGCTATT GCTTCCCGTA CGGCTTTCGT TTTCTCCTCC TTGTATAAAT | 2400 |
| | | | CCTGGTTGCT GTCTCTTTAT GAGGAGTTGT GGCCCGTTGT CCGTCAACGT | 2450 |
| | | | GGCGTGGTGT GCTCTGTGTT TGCTGACGCA ACCCCCACTG GCTGGGGCAT | 2500 |
| | | | TGCCACCACC TGTCAACTCC TTTCTGGGAC TTTCGCTTTC CCCCTCCCGA | 2550 |
| | | | TCGCCACGGC AGAACTCATC GCCGCCTGCC TTGCCCGCTG CTGGACAGGG | 2600 |
| | | | GCTAGGTTGC TGGGCACTGA TAATTCCGTG GTGTTGTCGG GGAAATCATC | 2650 |
| | | | GTCCTTTCCT TGGCTGCTCG CCTGTGTTGC CAACTGGATC CTGCGCGGGA | 2700 |
| | | | CGAGGCCTTC TGCCGGTTCT GCGGCCTCTC CCGCGTCTTC GCTTTCGGCC | 2750 |
| | | | CGAGGCCTTC TGCCGGTTCT GCGGCCTCTC CCGCGTCTTC GCTTTCGGCC | 2800 |
| | | | TCCGACGAGT CGGATCTCCC TTTGGGCCGC CTCCCCGCCT GGCTAGCCTG | 2850 |
| | | | TGCCTTCTAG TTGCCAGCCA TCTGTTGTTT GCCCCTCCCC CGTGCCTTCC | 2900 |
| | | | TTGACCCTGG AAGGTGCCAC TCCCACTGTC CTTTCCTAAT AAAATGAGGA | 2950 |
| | | | AATTGCATCG CATTGTCTGA GTAGGTGTCA TTCTATTCTG GGGGGTGGGG | 3000 |
| | | | TGGGGCAGGA CAGCAAGGGG GAGGATTGGG AAGACAATAG CAGGCATGCT | 3050 |
| | | | GGGGATGCGG TGGGCTCTAT GCGGCCGCGT CGAGCGC**[AGG AACCCCTAGT** | 3100 |
| | | | GATGGAGTTG GCCACTCCCT CTCTGCGCGC TCGCTCGCTC ACTGAGGCCG | 3150 |
| | | | CCCGGGCTTT GCCCGGGCGG CCTCAGTGAG CGAGCGAGCG CGCAG | 3195 |

The AAV2/6 vector comprising SB-71728 similarly comprises several features, and these are shown below in Table 4.

TABLE 4

Elements of SB-71728 AAV (SEQ ID NO: 26)

| Nucleotide Position-annotation | Feature/ Description | SEQ ID NO: | Sequence |
|---|---|---|---|
| 1-130 | 5' ITR [plain text in brackets] | 1 | CTGCGCGCTCGCTCGCTCACTGAGGCCGCCCGGGCAAAGCCCGGG CGTCGGGCGACCTTTGGTCGCCCGGCCTCAGTGAGCGAGCGAGCG CGCAGAGAGGGAGTGGCCAACTCCATCACTAGGGGTTCCT |
| 156-476 | ApoE (Enhancer) underlined | 15 | AGGCTCAGAGGCACACAGGAGTTTCTGGGCTCACCCTGCCCCCTT CCAACCCCTCAGTTCCCATCCTCCAGCAGCTGTTTGTGTGCTGCC TCTGAAGTCCACACTGAACAAACTTCAGCCTACTCATGTCCCTAA AATGGGCAAACATTGCAAGCAGCAAACAGCAAACACACAGCCCTC CCTGCCTGCTGACCTTGGAGCTGGGGCAGAGGTCAGAGACCTCTC TGGGCCCATGCCACCTCCAACATCCACTCGACCCCTTGGAATTTC GGTGGAGAGGAGCAGAGGTTGTCCTGGCGTGGTTTAGGTAGTGTG AGAGGG |
| 485-877 | hAAT (Promoter) *italics* | 17 | GATCTTGCTACCAGTGGAACAGCCACTAAGGATTCTGCAGTGAGA GCAGAGGGCCAGCTAAGTGGTACTCTCCCAGAGACTGTCTGACTC ACGCCACCCCTCCACCTTGGACACAGGACGCTGTGGTTTCTGAG CCAGGTACAATGACTCCTTTCGGTAAGTGCAGTGGAAGCTGTACA CTGCCCAGGCAAAGCGTCCGGGCAGCGTAGGCGGGCGACTCAGAT CCCAGCCAGTGGACTTAGCCCCTGTTTGCTCCTCCGATAACTGGG GTGACCTTGGTTAATATTCACCAGCAGCCTCCCCCGTTGCCCCTC TGGATCCACTGCTTAAATACGGACGAGGACAGGGCCCTGTCTCCT CAGCTTCAGGCACCACCACTGACCTGGGACAGT |
| 886-933 | 5' UTR Bold | 18 | CTTGTTCTTTTTGCAGAAGCTCAGAATAAACGCTCAACTTTGGCA GAT |
| 943-1075 | Human β globin/IgG chimeric intron | 3 | GTAAGTATCAAGGTTACAAGACAGGTTTAAGGAGACCAATAGAAA CTGGGCTTGTCGAGACAGAGAAGACTCTTGCGTTTCTGATAGGCA CCTATTGGTCTTACTGACATCCACTTTGCCTTTCTCTCCACAG |
| 1089-1154 | N-terminal peptide | 19 | GACTACAAAGACCATGACGGTGATTATAAAGATCATGACATCGAT TACAAGGATGACGATGACAAG |
| 1161-1181 | Nuclear localization signal *Bold italic* | 4 | CCCAAGAAGAAGAGGAAGGTC |
| 1200-1715 | ZFP 71728 DNA-binding domain lower case | 24 | GCCGCTATGGCTGAGAGGCCCTTCCAGTGTCGAATCTGCATGCGTAACTT CAGTCAGTCCTCCGACCTGTCCCGCCACATCCGCACCCACACCGGCGAGA AGCCTTTTGCCTGTGACATTTGTGGGAGGAAATTTGCCCTGAAGCACAAC CTGCTGACCCATACCAAGATACACACGGGCGAGAAGCCCTTCCAGTGTCG AATCTGCATGCAGAACTTCAGTGACCAGTCCAACCTGCGCGCCCACATCC GCACCCACACCGGCGAGAAGCCTTTTGCCTGTGACATTTGTGGGAGGAAA TTTGCCCGCAACTTCTCCCTGACCATGCATACCAAGATACACACCGGAGA GCGCGGCTTCCAGTGTCGAATCTGCATGCGTAACTTCAGTCTGCGCCACG ACCTGGAGCGCCACATCCGCACCCACACCGGCGAGAAGCCTTTTGCCTGT GACATTTGTGGGAGGAAATTTGCCCACCGCTCCAACCTGAACAAGCATAC CAAGATACACCTGCGG |
| 1722-2315 | FokI-KKR nuclease domain Dashed underline P478S | 25 | CAGCTGGTGAAGAGCGAGCTGGAGGAGAAGAAGTCCGAGCTGCGGCACAA GCTGAAGTACGTGCCCCACGAGTACATCGAGCTGATCGAGATCGCCAGGA ACAGCACCCAGGACCGCATCCTGGAGATGAAGGTGATGGAGTTCTTCATG AAGGTGTACGGCTACAGGGGAAAGCACCTGGGCGGAAGCAGAAAGCCTGA CGGCGCCATCTATACAGTGGGCAGCCCCATCGATTACGGCGTGATCGTGG ACACAAAGGCCTACAGCGGCGGCTACAATCTGAGCATCGCCAGGCCGAC GAGATGCAGAGATACGTGAAGGAGAACCAGACCCGGAATAAGCACATCAA CCCCAACGAGTGGTGGAAGGTGTACCCTAGCAGCGTGACCGAGTTCAAGT TCCTGTTCGTGAGCGGCCACTTCAAGGGCAACTACAAGGCCCAGCTGACC AGGCTGAACCGCAAAACCAACTGCAATGGCGCCGTGCTGAGCGTGGAGGA GCTGCTGATCGGCGGCGAGATGATCAAAGCCGGCACCCTGACACTGGAGG AGGTGCGGCGCAAGTTCAACAACGGCGAGATCAACTTCTGATAA |

TABLE 4-continued

Elements of SB-71728 AAV (SEQ ID NO: 26)

| Nucleotide Position-annotation | Feature/Description | SEQ ID NO: | Sequence |
|---|---|---|---|
| 2328-2919 | WPREmut6 3'UTR Dotted underline. | 22 | AATCAACCTCTGGATTACAAAATTTGTGAAAGATTGACTGATATT CTTAACTATGTTGCTCCTTTTACGCTGTGTGGATATGCTGCTTTA ATGCCTCTGTATCATGCTATTGCTTCCCGTACGGCTTTCGTTTTC TCCTCCTTGTATAAATCCTGGTTGCTGTCTCTTTATGAGGAGTTG TGGCCCGTTGTCCGTCAACGTGGCGTGGTGTGCTCTGTGTTTGCT GACGCAACCCCACTGGCTGGGGCATTGCCACCACCTGTCAACTC CTTTCTGGGACTTTCGCTTTCCCCCTCCCGATCGCCACGGCAGAA CTCATCGCCGCCTGCCTTGCCCGCTGCTGGACAGGGGCTAGGTTG CTGGGCACTGATAATTCCGTGGTGTTGTCGGGGAAATCATCGTCC TTTCCTTGGCTGCTCGCCTGTGTTGCCAACTGGATCCTGCGCGGG ACGTCCTTCTGCTACGTCCCTTCGGCTCTCAATCCAGCGGACCTC CCTTCCCGAGGCCTTCTGCCGGTTCTGCGGCCTCTCCCGCGTCTT CGCTTTCGGCCTCCGACGAGTCGGATCTCCCTTTGGGCCGCCTCC CCGCCTG |
| 2926-3148 | Polyadenylation signal | 7 | CTGTGCCTTCTAGTTGCCAGCCATCTGTTGTTTGCCCCTCCCCCG TGCCTTCCTTGACCCTGGAAGGTGCCACTCCCACTGTCCTTTCCT AATAAAATGAGGAAATTGCATCGCATTGTCTGAGTAGGTGTCATT CTATTCTGGGGGGTGGGGTGGGGCAGGACAGCAAGGGGGAGGATT GGGAAGACAATAGCAGGCATGCTGGGGATGCGGTGGGCTCTAT |
| 3166-3273 | 3' ITR [Bold text in brackets] | 8 | AGGAACCCCTAGTGATGGAGTTGGCCACTCCCTCTCTGCGCGCTC GCTCGCTCACTGAGGCCGCCCGGGCTTTGCCCGGGCGGCCTCAGT GAGCGAGCGAGCGCGCAG |

Complete Sequence of 71728 AAV:

(SEQ ID NO: 26)

[CTGCGCGCTC GCTCGCTCAC TGAGGCCGCC CGGGCAAAGC CCGGGCGTCG     50

GGCGACCTTT GGTCGCCCGG CCTCAGTGAG CGAGCGAGCG CGCAGAGAGG    100

GAGTGGCCAA CTCCATCACT AGGGGTTCCT] GCGGCCTAAG CTTGAGCTCT    150

TCGAAAGGCT CAGAGGCACA CAGGAGTTTC TGGGCTCACC CTGCCCCCTT    200

CCAACCCCTC AGTTCCCATC CTCCAGCAGC TGTTTGTGTG CTGCCTCTGA    250

AGTCCACACT GAACAAACTT CAGCCTACTC ATGTCCCTAA AATGGGCAAA    300

CATTGCAAGC AGCAAACAGC AAACACACAG CCCTCCCTGC CTGCTGACCT    350

TGGAGCTGGG GCAGAGGTCA GAGACCTCTC TGGGCCCATG CCACCTCCAA    400

CATCCACTCG ACCCCTTGGA ATTTCGGTGG AGAGGAGCAG AGGTTGTCCT    450

GGCGTGGTTT AGGTAGTGTG AGAGGGGTCC CGGGGATCTT GCTACCAGTG    500

GAACAGCCAC TAAGGATTCT GCAGTGAGAG CAGAGGGCCA GCTAAGTGGT    550

ACTCTCCCAG AGACTGTCTG ACTCACGCCA CCCCCTCCAC CTTGGACACA    600

GGACGCTGTG GTTTCTGAGC CAGGTACAAT GACTCCTTTC GGTAAGTGCA    650

GTGGAAGCTG TACACTGCCC AGGCAAAGCG TCCGGGCAGC GTAGGCGGGC    700

GACTCAGATC CCAGCCAGTG GACTTAGCCC CTGTTTGCTC CTCCGATAAC    750

TGGGGTGACC TTGGTTAATA TTCACCAGCA GCCTCCCCCG TTGCCCCTCT    800

GGATCCACTG CTTAAATACG GACGAGGACA GGGCCCTGTC TCCTCAGCTT    850

CAGGCACCAC CACTGACCTG GGACAGTCCT AGGTGCTTGT TCTTTTTGCA    900

GAAGCTCAGA ATAAACGCTC AACTTTGGCA GATACTAGTG AG<u>GTAAGTAT</u>    950

<u>CAAGGTTACA AGACAGGTTT AAGGAGACCA ATAGAAACTG GCTTGTCGA</u>    1000

<u>GACAGAGAAG ACTCTTGCGT TTCTGATAGG CACCTATTGG TCTTACTGAC</u>    1050

<u>ATCCACTTTG CCTTTCTCTC CACAGGACCG GTGCCATGGA</u> CTACAAAGAC    1100

CATGACGGTG ATTATAAAGA TCATGACATC GATTACAAGG ATGACGATGA    1150

TABLE 4-continued

Elements of SB-71728 AAV (SEQ ID NO: 26)

| Nucleotide Position-annotation | Feature/Description | SEQ ID NO: | Sequence |
|---|---|---|---|

CAAGATGGCC CCCAAGAAGA AGAGGAAGGT CGGCATTCAT GGGGTACCCg  1200
ccgctatggc tgagaggccc ttccagtgtc gaatctgcat gcgtaacttc  1250
agtcagtcct ccgacctgtc cgccacatc cgcacccaca ccggcgagaa  1300
gccttttgcc tgtgacattt gtgggaggaa atttgccctg aagcacaacc  1350
tgctgaccca taccaagata cacacgggcg agaagccctt ccagtgtcga  1400
atctgcatgc agaacttcag tgaccagtcc aacctgcgcg cccacatccg  1450
cacccacacc ggcgagaagc cttttgcctg tgacatttgt gggaggaaat  1500
ttgcccgcaa cttctccctg accatgcata ccaagataca caccggagag  1550
cgcggcttcc agtgtcgaat ctgcatgcgt aacttcagtc tgcgccacga  1600
cctggagcgc cacatccgca cccacaccgg cgagaagcct tttgcctgtg  1650
acatttgtgg gaggaaattt gcccaccgct ccaacctgaa caagcatacc  1700
aagatacacc tgcggGGATC CCAGCTGGTG AAGAGCGAGC TGGAGGAGAA  1750

GAAGTCCGAG CTGCGGCACA AGCTGAAGTA CGTGCCCCAC GAGTACATCG  1800

AGCTGATCGA GATCGCCAGG AACAGCACCC AGGACCGCAT CCTGGAGATG  1850

AAGGTGATGG AGTTCTTCAT GAAGGTGTAC GGCTACAGGG AAAGCACCT  1900

GGGCGGAAGC AGAAAGCCTG ACGGCGCCAT CTATACAGTG GGCAGCCCCA  1950

TCGATTACGG CGTGATCGTG GACACAAAGG CCTACAGCGG CGGCTACAAT  2000

CTGAGCATCG GCCAGGCCGA CGAGATGCAG AGATACGTGA AGGAGAACCA  2050

GACCCGGAAT AAGCACATCA ACCCCAACGA GTGGTGGAAG GTGTACCCTA  2100

GCAGCGTGAC CGAGTTCAAG TTCCTGTTCG TGAGCGGCCA CTTCAAGGGC  2150

AACTACAAGG CCCAGCTGAC CAGGCTGAAC CGCAAAACCA ACTGCAATGG  2200

CGCCGTGCTG AGCGTGGAGG AGCTGCTGAT CGGCGGCGAG ATGATCAAAG  2250

CCGGCACCCT GACACTGGAG GAGGTGCGGC GCAAGTTCAA CAACGGCGAG  2300

ATCAACTTCT GATAACTCGA GTCTAGAAAT CAACCTCTGG ATTACAAAAT  2350

TTGTGAAAGA TTGACTGATA TTCTTAACTA TGTTGCTCCT TTTACGCTGT  2400

GTGGATATGC TGCTTTAATG CCTCTGTATC ATGCTATTGC TTCCCGTACG  2450

GCTTTCGTTT TCTCCTCCTT GTATAAATCC TGGTTGCTGT CTCTTTATGA  2500

GGAGTTGTGG CCCGTTGTCC GTCAACGTGG CGTGGTGTGC TCTGTGTTTG  2550

CTGACGCAAC CCCCACTGGC TGGGGCATTG CCACCACCTG TCAACTCCTT  2600

TABLE 4-continued

Elements of SB-71728 AAV (SEQ ID NO: 26)

| Nucleotide Position-annotation | Feature/Description | SEQ ID NO: | Sequence |
|---|---|---|---|

TCTGGGACTT TCGCTTTCCC CCTCCCGATC GCCACGGCAG AACTCATCGC  2650

CGCCTGCCTT GCCCGCTGCT GGACAGGGGC TAGGTTGCTG GGCACTGATA  2700

ATTCCGTGGT GTTGTCGGGG AAATCATCGT CCTTTCCTTG GCTGCTCGCC  2750

TGTGTTGCCA ACTGGATCCT GCGCGGGACG TCCTTCTGCT ACGTCCCTTC  2800

GGCTCTCAAT CCAGCGGACC TCCCTTCCCG AGGCCTTCTG CCGGTTCTGC  2850

GGCCTCTCCC GCGTCTTCGC TTTCGGCCTC CGACGAGTCG GATCTCCCTT  2900

TGGGCCGCCT CCCCGCCTGG CTAGCCTGTG CCTTCTAGTT GCCAGCCATC  2950

TGTTGTTTGC CCCTCCCCCG TGCCTTCCTT GACCCTGGAA GGTGCCACTC  3000

CCACTGTCCT TTCCTAATAA AATGAGGAAA TTGCATCGCA TTGTCTGAGT  3050

AGGTGTCATT CTATTCTGGG GGGTGGGGTG GGGCAGGACA GCAAGGGGGA  3100

GGCCGCGTCG AGCGC[AGGAA CCCCTAGTGA TGGAGTTGGC CACTCCCTCT  3200

CTGCGCGCTC GCTCGCTCAC TGAGGCCGCC CGGGCTTTGC CGGGCGGCC  3250

TCAGTGAGCG AGCGAGCGCG CAG]

The AAV2/6 vector encoding the SB-IDUA transgene donor comprises several structural features: the 5' and 3' ITRs of the AAV vector, left and right homology arms (LA and RA) that have homology to the regions flanking the targeted cleavage site in the albumin gene, a splice acceptor derived from the human Factor IX exon 2 splice acceptor to ensure efficient joining of the transgene sequence to the albumin promoter, a codon optimized hIDUA cDNA sequence, and a polyadenylation signal sequence. The locations of the various elements are shown below in Table 5.

TABLE 5

Elements of IDUA AAV (SEQ ID NO: 28)

| Position | Feature Description | SEQ ID NO | Sequence |
|---|---|---|---|
| 1-130 | 5' ITR [plain text in brackets] | 1 | CTGCGCGCTCGCTCGCTCACTGAGGCCGCCCGGGCAAAGCCCGGGCGTCG GGCGACCTTTGGTCGCCCGGCCTCAGTGAGCGAGCGAGCGCGCAGAGAGG GAGTGGCCAACTCCATCACTAGGGGTTCCT |
| 271-550 | LA: Left homology arm *italics* | 13 | TTTATTCTATTTTCCCAGTAAAATAAAGTTTTAGTAAACTCTGCATCTTT AAAGAATTATTTTGGCATTTATTTCTAAAATGGCATAGTATTTTGTATTT GTGAAGTCTTACAAGGTTATCTTATTAATAAAATTCAAACATCCTAGGTA AAAAAAAAAAAGGTCAGAATTGTTTAGTGACTGTAATTTTCTTTTGCGC ACTAAGGAAAGTGCAAAGTAACTTAGAGTGACTGAAACTTCACAGAATAG GGTTGAAGATTGAATTCATAACTATCCCAA |
| 557-584 | SA: Splice acceptor Bold | 14 | ACTAAAGAATTATTCTTTTACATTTCAG |
| 587-2458 | hIDUA, codon optimized underlined | 27 | CACTTGGTCCACGTCGACGCTGCCAGAGCCCTGTGGCCGCTTCGAAGATT TTGGAGGTCAACGGGTTTCTGTCCTCCCCTTCCCCACTCGCAAGCAGATC AGTATGTACTGTCATGGGATCAACAGCTTAACCTCGCCTATGTCGGAGCA GTGCCTCACCGCGGGATCAAGCAAGTAAGGACACATTGGCTCCTTGAACT CGTCACCACGAGAGGATCGACGGGAAGGGGGCTTTCGTACAACTTCACTC ATCTCGATGGCTATTTGGATCTCCTCCGCGAGAATCAGTTGTTGCCAGGC TTCGAATTGATGGGATCGGCGAGCGGGCACTTTACAGACTTCGAGGACAA GCAGCAAGTGTTTGAGTGGAAGGACCTCGTGTCGTCGCTCGCGAGGAGAT ACATTGGTCGCTACGGTTTGGCGCATGTGTCAAAGTGGAACTTCGAAACG |

TABLE 5-continued

Elements of IDUA AAV (SEQ ID NO: 28)

| Feature Position | Description | SEQ ID NO | Sequence |
|---|---|---|---|
| | | | TGGAACGAGCCCGATCATCACGATTTTGACAACGTGTCAATGACCATGCA GGGTTTCCTTAACTATTACGACGCCTGTTCCGAGGGATTGAGGGCAGCAT CACCGGCGCTTCGGCTGGGAGGGCCTGGTGATAGCTTTCATACACCACCT CGATCGCCACTTTCGTGGGGGCTGCTGCGCCATTGTCACGATGGTACGAA CTTCTTCACCGGGGAAGCGGGGGTACGGCTTGATTACATCAGCCTCCACC GAAAGGGAGCGCGGTCAAGCATCTCGATTCTGGAGCAGGAGAAGGTAGTC GCTCAGCAGATCCGGCAACTCTTTCCCAAGTTCGCAGACACACCTATCTA CAATGATGAGGCAGACCCACTTGTGGGATGGTCCCTTCCGCAGCCATGGC GCGCAGATGTGACTTATGCCGCGATGGTAGTGAAAGTCATCGCCCAGCAC CAGAATCTGCTTCTTGCGAATACGACCAGCGCGTTTCTTACGCGCTTTT GTCGAACGATAATGCCTTCCTGTCATATCACCCCCATCCGTTTGCGCAGA GGACTCTTACGGCGCGATTCCAAGTGAATAACACCAGACCGCCGCACGTG CAGCTGTTGCGAAAACCCGTGTTGACTGCGATGGGGCTTCTGGCGTTGCT TGATGAGGAACAACTCTGGGCTGAAGTGTCCCAGGCGGGGACAGTACTTG ATAGCAATCATACAGTAGGCGTGTTGGCGTCGGCGCACCGACCGCAGGGA CCCGCGGATGCTTGGAGGGCAGCGGTCCTGATCTACGCCTCGGACGATAC TAGGGCACATCCCAACAGATCGGTCGCTGTCACCCTTCGCCTCAGAGGGG TCCCGCCTGGTCCCGGCTTGGTATACGTCACTAGATATCTCGACAATGGA CTGTGCAGCCCCGACGGAGAGTGGCGGAGGCTGGGACGGCCGGTGTTTCC GACAGCCGAGCAGTTTAGACGGATGAGGGCCGCTGAGGACCCCGTGGCAG CGGCACCGAGGCCCCTCCCGGCAGGAGGTCGCCTCACTCTTCGACCGGCA CTGCGGCTGCCGTCCCTTCTGCTCGTACACGTCTGCGCGCGACCCGAAAA GCCGCCTGGACAGGTAACCAGGCTCAGGGCGCTCCCCTTGACGCAGGGGC AGTTGGTACTTGTCTGGTCGGACGAACACGTGGGGTCCAAATGCTTGTGG ACGTATGAAATTCAGTTTTCCCAAGACGGGAAAGCGTACACTCCGGTGTC GCGCAAACCCTCCACGTTCAACCTCTTCGTCTTTTCCCAGACACGGGAG CCGTATCAGGGTCGTACCGAGTCAGAGCCCTCGATTATTGGGCGAGGCCT GGGCCGTTCTCGGACCCTGTACCATACTTGGAAGTGCCGGTGCCCAGGGG ACCGCCCTCGCCTGGTAATCCT |
| 2471-2695 | poly A lowercase | 7 | CTGTGCCTTCTAGTTGCCAGCCATCTGTTGTTTGCCCCTCCCCCGTGCCT TCCTTGACCCTGGAAGGTGCCACTCCCACTGTCCTTTCCTAATAAAATGA GGAAATTGCATCGCATTGTCTGAGTAGGTGTCATTCTATTCTGGGGGGTG GGGTGGGGCAGGACAGCAAGGGGGAGGATTGGGAAGACAATAGCAGGCAT GCTGGGGATGCGGTGGGCTCTATGG |
| 2702-2801 | RA: Right homology arm Double underlined | 16 | CTATCCATTGCACTATGCTTTATTTAAAAACCACAAAACCTGTGCTGTTG ATCTCATAAATAGAACTTGTATTTATATTTATTTTCATTTTAGTCTGTCT |
| 2948-3055 | 3' ITR [Bold bracketed] | 8 | AGGAACCCCTAGTGATGGAGTTGGCCACTCCCTCTCTGCGCGCTCGCTCG CTCACTGAGGCCGCCCGGGCTTTGCCCGGGCGGCCTCAGTGAGCGAGCGA GCGCGCAG |

Complete Sequence of IDUA AAV:

(SEQ ID NO: 28)

[CTGCGCGCTC GCTCGCTCAC TGAGGCCGCC CGGGCAAAGC CCGGGCGTCG    50

GGCGACCTTT GGTCGCCCGG CCTCAGTGAG CGAGCGAGCG CGCAGAGAGG    100

GAGTGGCCAA CTCCATCACT AGGGGTTCCT] GCGGCCTAAG CTTGAGCGGA    150

GTTCCAATTG TACTGTACAG AACCATGGTC ACATGTTTAA CGCTAGCGTG    200

CCGACCTGGT AAACTGATCA GTGGGTGCAC TTAGGACTGC GTCTTACGCT    250

AATCACATGC GTGCGGCCGC TTTATTCTAT TTTCCCAGTA AAATAAAGTT    300

TTAGTAAACT CTGCATCTTT AAAGAATTAT TTTGGCATTT ATTTCTAAAA    350

TGGCATAGTA TTTTGTATTT GTGAAGTCTT ACAAGGTTAT CTTATTAATA    400

AAATTCAAAC ATCCTAGGTA AAAAAAAAAA AAGGTCAGAA TTGTTTAGTG    450

ACTGTAATTT TCTTTTGCGC ACTAAGGAAA GTGCAAAGTA ACTTAGAGTG    500

ACTGAAACTT CACAGAATAG GGTTGAAGAT TGAATTCATA ACTATCCCAA    550

GGTACCACTA AAGAATTATT CTTTTACATT TCAGCGCACT TGGTCCACGT    600

CGACGCTGCC AGAGCCCTGT GGCCGCTTCG AAGATTTTGG AGGTCAACGG    650

GTTTCTGTCC TCCCCTTCCC CACTCGCAAG CAGATCAGTA TGTACTGTCA    700

TABLE 5-continued

Elements of IDUA AAV (SEQ ID NO: 28)

| Feature Position Description | SEQ ID NO Sequence | |
|---|---|---|
| | TGGGATCAAC AGCTTAACCT CGCCTATGTC GGAGCAGTGC CTCACCGCGG | 750 |
| | GATCAAGCAA GTAAGGACAC ATTGGCTCCT TGAACTCGTC ACCACGAGAG | 800 |
| | GATCGACGGG AAGGGGGCTT TCGTACAACT TCACTCATCT CGATGGCTAT | 850 |
| | TTGGATCTCC TCCGCGAGAA TCAGTTGTTG CCAGGCTTCG AATTGATGGG | 900 |
| | ATCGGCGAGC GGGCACTTTA CAGACTTCGA GGACAAGCAG CAAGTGTTTG | 950 |
| | AGTGGAAGGA CCTCGTGTCG TCGCTCGCGA GGAGATACAT TGGTCGCTAC | 1000 |
| | GGTTTGGCGC ATGTGTCAAA GTGGAACTTC GAAACGTGGA ACGAGCCCGA | 1050 |
| | TCATCACGAT TTTGACAACG TGTCAATGAC CATGCAGGGT TTCCTTAACT | 1100 |
| | ATTACGACGC CTGTTCCGAG GGATTGAGGG CAGCATCACC GGCGCTTCGG | 1150 |
| | CTGGAGGGC CTGGTGATAG CTTTCATACA CCACCTCGAT CGCCACTTTC | 1200 |
| | GTGGGGCTG CTGCGCCATT GTCACGATGG TACGAACTTC TTCACCGGGG | 1250 |
| | AAGCGGGGGT ACGGCTTGAT TACATCAGCC TCCACCGAAA GGGAGCGCGG | 1300 |
| | TCAAGCATCT CGATTCTGGA GCAGGAGAAG GTAGTCGCTC AGCAGATCCG | 1350 |
| | GCAACTCTTT CCCAAGTTCG CAGACACACC TATCTACAAT GATGAGGCAG | 1400 |
| | ACCCACTTGT GGGATGGTCC CTTCCGCAGC CATGGCGCGC AGATGTGACT | 1450 |
| | TATGCCGCGA TGGTAGTGAA AGTCATCGCC CAGCACCAGA ATCTGCTTCT | 1500 |
| | TGCGAATACG ACCAGCGCGT TTCCTTACGC GCTTTTGTCG AACGATAATG | 1550 |
| | CCTTCCTGTC ATATCACCCC CATCCGTTTG CGCAGAGGAC TCTTACGGCG | 1600 |
| | CGATTCCAAG TGAATAACAC CAGACCGCCG CACGTGCAGC TGTTGCGAAA | 1650 |
| | ACCCGTGTTG ACTGCGATGG GGCTTCTGGC GTTGCTTGAT GAGGAACAAC | 1700 |
| | TCTGGGCTGA AGTGTCCCAG GCGGGGACAG TACTTGATAG CAATCATACA | 1750 |
| | GTAGGCGTGT TGGCGTCGGC GCACCGACCG CAGGGACCCG CGGATGCTTG | 1800 |
| | GAGGGCAGCG GTCCTGATCT ACGCCTCGGA CGATACTAGG GCACATCCCA | 1850 |
| | ACAGATCGGT CGCTGTCACC CTTCGCCTCA GAGGGGTCCC GCCTGGTCCC | 1900 |
| | GGCTTGGTAT ACGTCACTAG ATATCTCGAC AATGGACTGT GCAGCCCCGA | 1950 |
| | CGGAGAGTGG CGGAGGCTGG GACGGCCGGT GTTTCCGACA GCCGAGCAGT | 2000 |
| | TTAGACGGAT GAGGGCCGCT GAGGACCCCG TGGCAGCGGC ACCGAGGCCC | 2050 |
| | CTCCCGGCAG GAGGTCGCCT CACTCTTCGA CCGGCACTGC GGCTGCCGTC | 2100 |
| | CCTTCTGCTC GTACACGTCT GCGCGCGACC CGAAAAGCCG CCTGGACAGG | 2150 |
| | TAACCAGGCT CAGGGCGCTC CCCTTGACGC AGGGGCAGTT GGTACTTGTC | 2200 |
| | TGGTCGGACG AACACGTGGG GTCCAAATGC TTGTGGACGT ATGAAATTCA | 2250 |
| | GTTTTCCCAA GACGGGAAAG CGTACACTCC GGTGTCGCGC AAACCCTCCA | 2300 |

TABLE 5-continued

Elements of IDUA AAV (SEQ ID NO: 28)

| Position | Feature Description | SEQ ID NO | Sequence |
|---|---|---|---|

| CGTTCAACCT CTTCGTCTTT TCCCCAGACA CGGGAGCCGT ATCAGGGTCG | 2350 |
| TACCGAGTCA GAGCCCTCGA TTATTGGGCG AGGCCTGGGC CGTTCTCGGA | 2400 |
| CCCTGTACCA TACTTGGAAG TGCCGGTGCC CAGGGGACCG CCCTCGCCTG | 2450 |
| GTAATCCTTG ATAAAGATCT ctgtgccttc tagttgccag ccatctgttg | 2500 |
| tttgccccte ccccgtgcct tccttgaccc tggaaggtgc cactcccact | 2550 |
| gtcctttcct aataaaatga ggaaattgca tcgcattgtc tgagtaggtg | 2600 |
| tcattctatt ctgggggtg gggtggggca ggacagcaag ggggaggatt | 2650 |
| gggaagacaa tagcaggcat gctggggatg cggtgggctc tatggACCGG | 2700 |
| TCTATCCATT GCACTATGCT TTATTTAAAA ACCACAAAAC CTGTGCTGTT | 2750 |
| GATCTCATAA ATAGAACTTG TATTTATATT TATTTTCATT TTAGTCTGTC | 2800 |
| TGGATCCACA AATTAATCGA ACCTGCAGCT GATATCGACG CTTAAGTAGG | 2850 |
| GCTTAGCAAA CGCGTCTCCA ACGTTTCGCC GTTAACACCC CACATAGTGA | 2900 |
| GTGGTCTTAG TAGTCCGGGT GTTTAAACTG AAAGATAACT CGAGCGC[AGG | 2950 |
| AACCCCTAGT GATGGAGTTG GCCACTCCCT CTCTGCGCGC TCGCTCGCTC | 3000 |
| ACTGAGGCCG CCCGGGCTTT GCCCGGGCGG CCTCAGTGAG CGAGCGAGCG | 3050 |
| CGCAG] | 3055 |

Example 2

Compositions comprising the polynucleotides and AAVs as described in Example 1 were prepared as follows: The components were supplied in three capped vials: one for ZFN1 (SB-47171, white capped and labeled SB-A6P-ZLEFT or SB-71557, labeled as SB-A6P-ZL2); ZFN2 (SB47898, blue capped and labeled SB-A6P-ZRIGHT or SB-71728, labeled as SB-A6P-ZR2); and hIDUA Donor (hIDUA, orange capped and labeled SB-A6P-HRL). The product components were all purified AAV individually formulated in phosphate buffered saline (PBS) containing CaCl2, MgCl2, NaCl, sucrose and Kolliphor® (Poloxamer) P188 or in a Normal Saline (NS) formulation. Dose calculations were performed using the subject's weight and rounded to two decimal points. The calculations were done by multiplying the cohort dose by the subject weight at baseline, and then dividing by the vg/mL concentration. The three product component volumes were added together and the total volume determined. In addition, the volume of human serum albumin (HSA) intravenous solution for addition was calculated to achieve a final concentration of 0.25% HSA and finally the PBS or NS was added the required amount to achieve the correct component concentration.

The product components were then added to an IV infusion bag containing 0.25% HSA in NS or PBS. Each product component was added separately and then the bag was mixed gently and transferred to the person responsible for infusion. The product was then infused into subjects at a rate of 100 mL/hour using an infusion pump (Sigma Spectrum).

Example 3

Study Eligibility and Exclusion Criteria

Key eligibility criteria for subjects in the study included: male or female ≥18 years of age; clinical diagnosis of attenuated MPS I (MPS HIS, MPS IS, MPS IH post-HSCT); IDUA deficiency confirmed by gene sequencing; Magnetic resonance imaging (MRI) negative for liver mass.

Key exclusion criteria for subjects in the study included: known unresponsiveness to enzyme replacement therapy; neutralizing antibodies in the serum to AAV2/6; serious intercurrent illness or clinically significant organic disease (unless secondary to MPS I) such as cardiovascular, hepatic, pulmonary, neurologic, or renal disease. Receiving anti-retroviral therapy for hepatitis B or C, or active hepatitis B or hepatitis C or human immunodeficiency virus (HIV) 1/2; lack of tolerance to laronidase treatment with significant infusion-associated reactions (IARs) or occurrence of anaphylaxis; polymorphisms in the ZFN targeted region in the albumin locus; liver fibrosis score of 3 or 4 on a 0 to 4 point scale (Desmet et al. (1994) *Hepatology* 19(6):1513-20) if subject has had a liver biopsy within 2 years of screening, markers of hepatic dysfunction; creatinine≥1.5 mg/dL; pregnant or breastfeeding female; contraindication to the use of corticosteroids; current treatment with systemic (iv or oral) immunomodulatory agent or steroid use; history of active malignancy in past 5 years; participation in prior investigational drug or medical device study within the previous 3 months; prior treatment with a gene therapy product; and elevated or abnormal α-fetoprotein.

Study Design

The study was performed on subjects with MPS I disease. The doses used in the cohorts are shown below in Table 6. Cohort 1 is considered the low dose, cohort 2 is the mid dose, and cohort 3 is the high dose. For all cohorts, total AAV dose includes 2 ZFN vectors and 1 donor vector in a fixed ratio of 1:1:8.

TABLE 6

| | | Evaluation doses | | | | |
|---|---|---|---|---|---|---|
| Cohort | Subjects | ZFN 1 (SB-41717 or 71557) vg/kg | ZFN 2 (SB-47898 or 71728) vg/kg | hIDUA donor (SB-IDUA) vg/kg | Total rAAV vg/kg | Dose Description |
| 1 | 2 | 1.00e+12 | 1.00e+12 | 8.00e+12 | 1.00e+13 | Starting dose |
| 2 | 2 | 5.00e+12 | 5.00e+12 | 4.00e+13 | 5.00e+13 | 5x starting dose |
| 3 | 5 | To be determined | | | | Maximally tolerated dose |

Subjects who received ERT prior to enrollment continued to receive ERT during the study and remain on their current schedule per standard of care; however, ERT was omitted during the week of infusion to facilitate accurate baseline testing (e.g., of urine GAG levels, and leukocyte and plasma IDUA activity) at ERT trough levels and to allow a week free of ERT after the infusion.

To minimize the potential immune response to the AAV capsid protein, the engineered ZFNs, or the endogenous hIDUA, and to preserve hepatic function, prednisone or equivalent corticosteroid was administered prophylactically starting 2 days prior to infusion, and was tapered over a period of approximately 20 weeks.

Clinical Endpoints

Primary endpoint: The primary endpoint of this study were the safety and tolerability of the composition as assessed by incidence of adverse events and significant adverse events. Additional safety evaluations included: routine hematology, chemistry, and liver function laboratory tests, vital signs, physical exam, ECG, ECHO, and concomitant medications; cranial nerve exam and muscle strength testing; serial α-fetoprotein testing and MM of liver to evaluate for liver mass. Safety assessment was performed on all subjects. All reported adverse events were coded to a standard set of terms using the Medical Dictionary for Regulatory Activities (MedDRA) AE dictionary. The frequency of each event was summarized by severity and by relatedness to the study drug material.

Key secondary endpoints included: change from baseline in: IDUA activity measured in plasma and leukocytes, total GAG, DS GAG, and HS GAG levels (expressed as a ratio to creatinine) measured in urine; AAV2/6 clearance measured by vector genomes in plasma, saliva, urine, stool, and semen by PCR. Urine GAG levels are a key biomarker of MPS I disease pathophysiology.

Key exploratory endpoints included a change from baseline in: percentage and durability of gene modification at the albumin locus in liver tissue obtained at biopsy; imaging, functional and neurocognitive testing related to MPS I; liver and cerebrospinal fluid (CSF) GAG levels and any immune response to AAV2/6 and/or ZFNs.

From consenting subjects, additional samples may be collected for future research objectives. Such future research objectives may include analysis of plasma markers of severity of disease, response to therapy (e.g., cytokines, soluble cell surface proteins, soluble receptors), and functional improvements (e.g., neurological function, musculoskeletal function), as well as determination of AAV virus inhibition, function, immunogenicity, or pharmacodynamics (e.g., antibodies, soluble receptors, AAV viral receptor inhibitors, cytokines, co-existing alternate serotype antibodies).

Statistical Analysis and Data Analysis

This was an exploratory Phase I study and thus there will be limited statistical power to evaluate efficacy and related biological endpoints. Therefore, analyses were primarily descriptive and exploratory in nature. This study will enroll 9 subjects (2 subjects in each of 2 cohorts, with potential enrollment of 5 additional subjects at the maximal tolerated dose). The selection of 2 subjects per cohort was not based on statistical calculations since this is a Phase I safety study to evaluate safety and tolerability. All tables, listings, and data summaries were performed in SAS version 9.2 or later.

Patients

The patient demographics are shown below in Table 7. Table 8 lists the exposure to treatment that each subject had at 32 weeks post trial initiation.

TABLE 7

| Patient Demographics | |
|---|---|
| Subject Characteristics | Overall (N = 3) |
| Age (Years) | |
| number of patients | 3 |
| Min-Max | 23.00, 37.00 |
| Mean (SD) | 29.00 (7.21) |
| Median | 27.00 |
| Sex, n (%) | |
| Male | 1 (33.3) |
| Female | 2 (66.7) |
| Race, n (%) | |
| Asian | 2 (66.7) |
| White | 1 (33.3) |

TABLE 8

| Treatment exposure (approximate) | | |
|---|---|---|
| Subject | Dose Cohort | Follow-Up (Weeks) |
| 1 | 1 | 22 |
| 2 | 2 | 9 |
| 3 | 2 | 5 |

Observed Adverse Events

All subjects reported treatment emergent adverse events (TEAEs), consistent with ongoing MPS I disease. Most were mild (grade 1) and resolved without treatment. In general, the study drug was administered to three subjects with attenuated MPS I at a dose of up to 5e13 vg/kg and was generally well-tolerated.

Study drug-related Adverse Events (AEs) were mild (Grade 1), and all were consistent with the ongoing MPS I disease. No SAEs were reported, and no AEs to the study drug were reported. No increase in liver function tests were reported. The AEs are shown below in Table 9.

TABLE 9

Study Drug-related Adverse Events

| Preferred Term | Cohort 1 (N = 1) n [T] | Cohort 2 (N = 2) n [T] | Overall (N = 3) n[T] |
|---|---|---|---|
| Any TEAE 1- Mild 2- Moderate | 1 [2] | 2 [4] | 3 [6] |
| Headache | 1[1] | None | 1[1] |
| Acne | | 2[2] | 2[2] |
| Upper respiratory tract infection | 1[1] | None | 1[1] |
| Musculoskeletal stiffness | None | 1[1] | 1[1] |
| Oropharyngeal pain | None | 1[1] | 1[1] |

In Table 9, 'N' indicates the total number of subjects in each treatment group; 'n' indicates the number of subjects with an adverse event for each preferred term; and '[T]' indicates the total number of adverse events.

All subjects were tapered on prophylactic prednisone without the need for increased dosing. All subjects had normal AST and ALT readings throughout the period following treatment.

Preliminary Plasma IDUA Measurements

Plasma IDUA activity was measured at trough, which was defined as in the period immediately prior to ERT dosing when possible, and no less than 96 hours after the subject's last ERT infusion. The activity of α-L-iduronidase was determined by methods known in the art (see Example 4). In this study at this initial time point, plasma IDUA activity was not significantly changed from pre-treatment values.

Leukocyte IDUA Results, Cohorts 1 and 2

Figure 2:
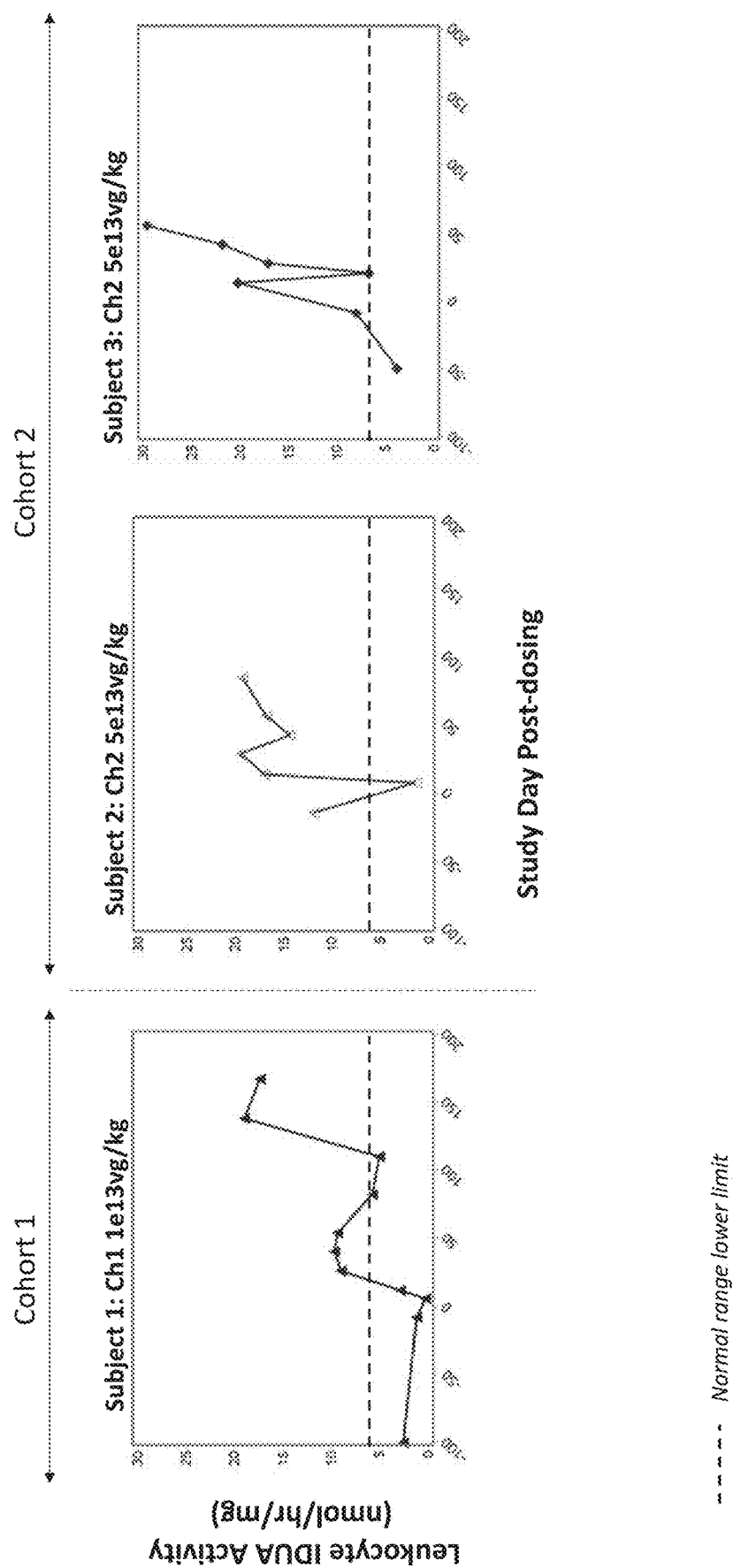
FIG. 2 depicts IDUA activity in subject leukocytes. Graphs displaying data from 3 subjects is shown where Subject 1 was in dose cohort 1 and Subject 2 and Subject 3 were in dose cohort 2. Study drug was administered on Day 0. All patients showed an increase in leukocyte IDUA activity as compared with levels prior to dosing (negative study day numbers). The horizontal dashed line in each graph depicts the normal range lower limit.
Figure 3:
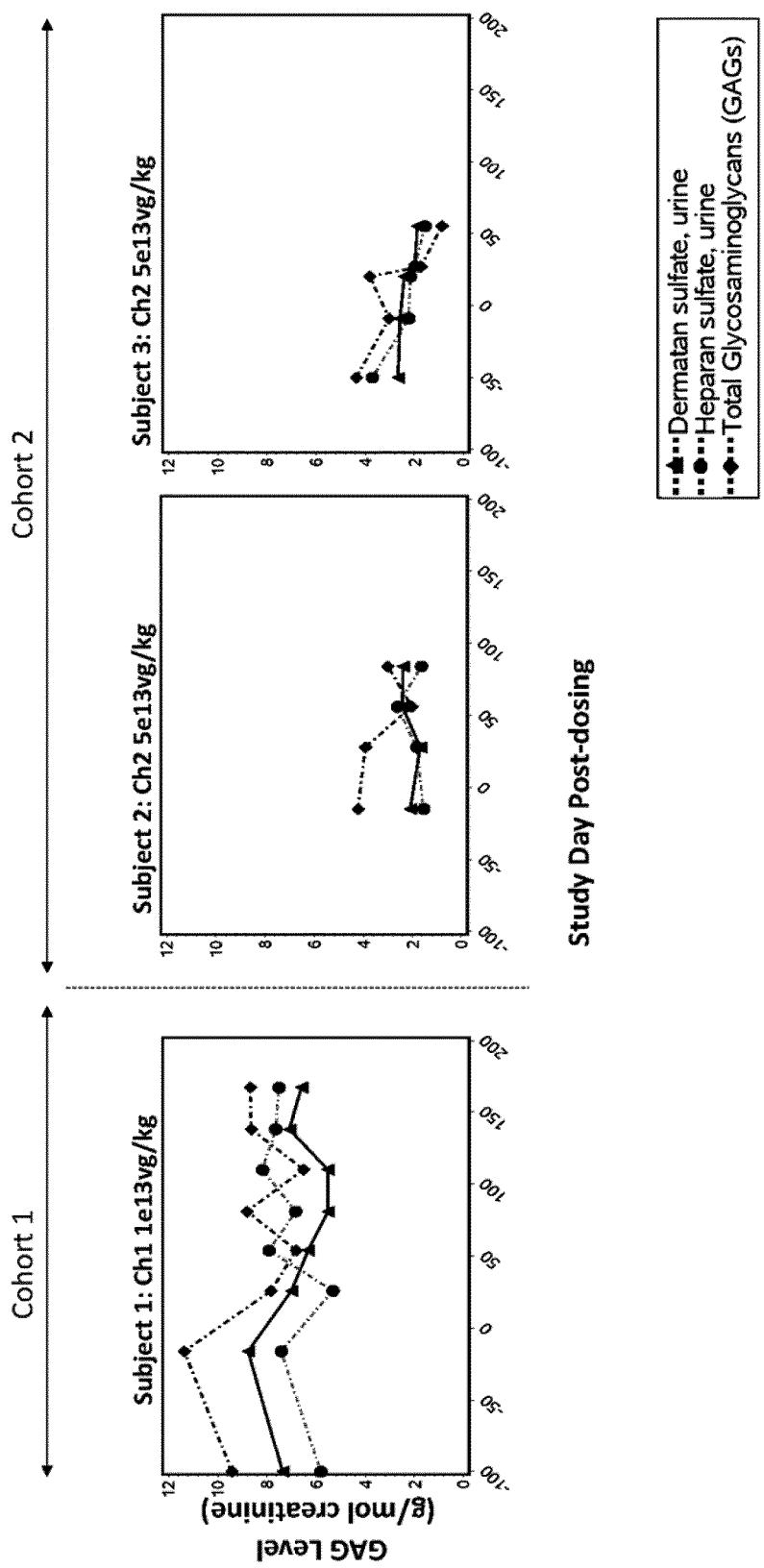
FIG. 3 depicts urine GAG levels in each subject. Graphs displaying data from the three subjects is shown where Subject 1 was in dose cohort 1 and Subject 2 and Subject 3 were in dose cohort 2. Study drug was administered on Day 0.

IDUA levels in the subject's leukocytes were analyzed using methods known in the art (see Example 4). Because the subjects were enrolled in the study at different points in time, there were different time periods of post-dosing results reported as shown in Table 8. The results demonstrated that the treated subjects had IDUA levels in their leukocytes above the normal range lower limit. Increases in leukocyte IDUA activity into the normal range were observed in all three threated subjects at both the 1e13 and 5e13 vg/kg doses. Comparison of the IDUA levels found prior to dosing (see FIG. 2, Study Day post dosing "0" indicates the day compositions disclosed herein were administered to each subject) demonstrates that each subject had an increase in leukocyte IDUA activity.

Urine Glycosaminoglycan Levels Results

Determinations were made of total urine GAG levels as well as levels of dermatan sulfate and heparan sulfate. Methods used were those known in the art (see Example 4).

The results of the urine GAG analysis are shown in FIG. 4. These results are a preliminary read at this early timepoint. As the subjects progress in the clinical study, further data points will be analyzed for loss of urine GAGs.

Summary of Results for Subjects 1-3

Also known as Hurler syndrome, MPS I is a rare inherited metabolic disease caused by a deficiency of IDUA, an enzyme needed to break down GAGs in the lysosomes. Without IDUA, the toxic buildup of GAGs in the cells can result in tissue and organ damage, musculoskeletal problems and other symptoms. The current standard-of-care treatment for MPS I is enzyme replacement therapy (ERT), given as weekly intravenous infusions. For severe MPS I patients, bone marrow transplant is also a common treatment.

The study described herein contained two dose cohorts. One patient was treated in the first cohort at a dose of 1e13 vg/kg, and 2 patients were treated in the second cohort at 5e13.

Safety data collected from all three patients showed that the administration of the study drug was generally well-tolerated with a favorable safety profile. Eight total adverse events were reported, all were mild or moderate, consistent with ongoing MPS I disease and resolved without treatment. None of the reported adverse events were determined to be related to study drug treatment. No serious adverse events or SAEs were reported and no persistent transaminitis was observed.

In MPS I, leukocyte IDUA activity is commonly used to estimate levels of IDUA enzyme in the tissues of bone marrow transplant patients, as increased IDUA activity in leukocytes is associated with improved clinical outcomes in a bone marrow transplant setting. The results indicate a dose-dependent increase in leukocyte IDUA activity, with activity levels rising above baseline and in the normal range (normal range is 6.0-71.4 nmol/hr/mg). Plasma IDUA activity was unchanged from baseline in all three patients. Plasma IDUA activity was unchanged from baseline in all three patients. This may be due to the contrary PK/PD properties of the study drug and genome editing therapy and MPS I disease biology.

Baseline urine GAG measurements for the three patients were in a range considered to be at or slightly above normal. In this limited duration data set, urine GAG measurements showed no clear trend or meaningful change. Additional follow-up is needed to determine whether any meaningful change in urine GAGs emerges. However, the early observations of increased leukocyte IDUA activity, a target tissue, observed in treated subjects treated with compositions as described herein was encouraging.

Additional studies are performed using the composition disclosed herein comprising AAV SB-71557 and AAV SB-71728 (in place of 47171 and 47898) and an AAV hIDUA Donor. In pre-clinical studies, AAV SB-71557 and AAV SB 71728 demonstrated improved cutting efficiency (5- to 30-fold) and improved expression (5- to 20-fold increase) of IDUA (see U.S. Provisional application 62/728, 226), the enzyme deficient in patients with MPS I.

Example 4

IDUA Enzyme Assay

Exemplary laboratory procedures that may be utilized are conducted as follows. To detect IDUA enzyme activity, there are many assays that can be used.

One exemplary assay is as follows: The activity of α-L-iduronidase was determined by a fluorometric assay using 4-methylumbelliferyl α-L-iduronide (Glycosynth) as the substrate according to the established assay condition (Whitley et al. (1987) *Am J Med Genet* 28:233-243; Whitley (1986) *Birth Defects Orig Artic Ser.* 22(1):7-24. The 4MU-iduronide substrate was diluted with sodium formate buffer, 0.4 M, pH 3.5 in the narrow, well-established optimal range of pH (Hopwood et al. (1979) *Clin Chim* Acta. 92:257-265, Whitley (1986), ibid), and at selected substrate concentrations. Then, 25 μL aliquots of substrate were mixed with 25 μL of biological sample (e.g. plasma, leukocytes, tissue homogenates). The mixture was incubated at 37° C. for 30 min, and 200 μL glycine carbonate buffer (pH 10.4) was added to quench the reaction. α-L-iduronidase catalyzed the cleavage of the non-fluorescent substrate (4MU-iduronide) into a fluorescent product (4-MU). 4-Methylumbelliferone (4-MU, Sigma) was used to make the standard curve. The resulting fluorescence was measured using a Bio-Tek plate reader with excitation at 355 nm and emission at 460 nm. α-L-iduronidase enzyme activity was expressed in units (nmol converted to product per hour) per mg protein as determined with a Pierce protein assay kit (Fisher). All reactions were run in triplicate.

Another exemplary fluorometric assay, using 4-methylumbelliferyl α-1-iduronide (4-MU, Glycosynth, Cheshire, UK or Sigma Aldrich, St. Louis MO) as the substrate for measuring IDUA activity in leukocytes (Isman et al. (2005) *Clin Chem* 51(3)) is as follows:

Blood is obtained from healthy adult donors with informed consent. Leukocytes are fractionated with Ficoll-Paque as follows: Blood (10 mL) is drawn into evacuated tubes (Vacutainer; Becton Dickinson) containing sodium heparin, transferred to a 40-mL plastic centrifuge tube, diluted with 20 mL of Hanks Balanced Salt Solution (HBSS), and gently mixed. The diluted blood is gently layered on 15 mL of Ficoll-Paque in a 20×150 mm centrifuge tube and centrifuged at 360 g for 50 min at room temperature; the supernatant is carefully aspirated and discarded. The mononuclear cells at the interface with the plasma are pipetted into a plastic centrifuge tube, washed with HBSS, and centrifuged twice at 170 g for 10 min. The mononuclear pellets are then rinsed with saline solution (9 g/L NaCl) to remove residual HBSS and used for the experiments (hereafter referred to as the mononuclear fraction). The mononuclear fraction contains 90-93% lymphocytes and 3-5% monocytes when evaluated by Wright staining. The granulocyte/erythrocyte fraction that is present at the bottom of the initial Ficoll-Paque separation is washed twice with isotonic saline, and the erythrocytes are subsequently removed by hypotonic lysis, giving a granulocyte fraction (hereafter referred to as granulocytes) consisting of 94-98% granulocytes. Cell pellets are stored at −20° C., and all enzyme assays are carried out within 1-5 days after isolation of the cells.

α-Iduronidase activity (EC 3.2.1.76) is determined by the method of Rome et al. (1979) *Proc Natl Acad Sci USA* 76:2331-2334). Fluorescence is measured for this and all other assays with 4-methylumbelliferone-based substrates with an excitation wavelength of 365 nm and an emission wavelength of 450 nm; the results are compared with a calibration curve prepared with 4-methylumbelliferone. Results are reported as the mean ratio (with 95% confidence intervals) of enzyme activity in matched samples.

A second assay known in the art (Aronovich et al. (1986) *Am. J. Hum. Genet*. 58:75-85) is as follows: Leukocytes were prepared by differential sedimentation on dextran followed by two cycles of hypotonic hemolysis (Lichtman 1990). For some individuals, a lymphoblastoid cell line (LCL) was prepared by transformation with Epstein-Barr virus. The activity of IDUA was measured using fluorogenic substrate 4-methylumbelliferone (MU) CC-L-iduronide (Calbiochem) and expressed as nmol MU/mg protein/h, or nmol MU/ml plasma/h, as described elsewhere (Whitley et al. (1987) *Am J Med Genet* 28:233-243). It is notable that the assay was originally developed to optimize human leukocyte IDUA activity at 37° C. with respect to reaction pH (3.3) and substrate concentration (2.85 mM, >10-fold above the Km). Under these conditions, the reaction was found to be linear with respect to reaction time for −3 h, although reactions were either 30 min or 2 h in the current study. Protein concentration was measured with Coomasie blue (Bio-Rad).

Plasma IDUA enzyme activity was according to a previously published method (Wasteson and Neufeld (1982) *Meth Enzymol* 83:573-578; Clarke et al. (1990) *Clin Genet* 37:355-362). One unit of enzyme activity was defined as the percent of $^3$H substrate converted to product. Specific enzymatic activity was reported as U/mg protein/h.

4-MU iduronide is diluted with sodium formate buffer (0.4 M, pH 3.5). Then, 25 μL aliquots of substrate (360 μM) are mixed with 25 μL aliquots of tissue homogenates. The mixture is incubated at 37° C. for 30 min, and 200 μL glycine carbonate buffer (pH 10.4) is added to quench the reaction. IDUA catalyzes the cleavage of the non-fluorescent substrate (4-MU iduronide) into a fluorescent product (4-MU). 4-methylumbelliferone (Sigma-Aldrich, St. Louis, MO) is used to make the standard curve. The resulting fluorescence is measured using a microplate reader (BioTek, Winooski, VT) with excitation at 355 nm and emission at 460 nm. IDUA enzyme activity is expressed in units (nmol converted to product per hour) per mg protein as determined with a Pierce protein assay kit (Thermo Fisher Scientific, Waltham, MA). All reactions are run in triplicate (Ou et al. (2018) *Mol Genet Metab* 123(2):105-111).

Another exemplary assay to measure IDUA activity from tissues is as follows: After sacrifice using a ketamine/xylazine cocktail (10 μL/g), mice were perfused transcardially with 1×PBS. Samples from the brain, heart, kidney, liver, spleen and lungs were immediately harvested and flash-frozen for IDUA and GAG analysis. Harvested mouse tissues were placed in 1 mL PBS in an Eppendorf tube on ice and homogenized using a motorized pestle. Then 11 μL of 10% Triton X-100 in PBS was added and the homogenate kept on ice for 10 min. Protein concentration in the clarified supernatant was estimated by the Bradford colorimetric method.

IDUA activity was assayed as follow: Briefly, 25 μl of a solution of 50 μM 4-methylumbelliferyl alpha-L-iduronide made in 0.4 M sodium formate buffer, pH 3.5, containing 0.2% Triton X-100 was added to 25 μl of tissue homogenate and incubated for 1 h at 37° C. in the dark. The reaction was quenched by adding 200 μl of 0.5 M NaOH/glycine buffer, pH 10.3. Tubes were centrifuged for 1 min at 13,000 rpm at 4° C., the supernatant transferred to a 96 wells plate, and fluorescence read at 365 nm excitation wavelength and 450 nm emission wavelength using a Spectra Max Gemini XS fluorometric plate reader (Molecular Devices, Sunnyvale, CA). Note: Sodium formate, formic acid, 4-methylumbelliferone, glycine, NaOH, Triton X-100 and sodium azide were obtained from Sigma (St. Louis, MO) and 4-methylumbelliferyl alpha-L-iduronide from Glycosynth (Warrington, Cheshire, UK). IDUA activity in the tissue samples was calculated as: Activity in ng/h=(flourometric reading of the tissue sample×A)−B, where A and B were the values obtained from the curve fit equation of the standard curve generated using pure end product (4-methylumbelliferone). Specific activity of IDUA was expressed as nmol/h/mg protein in each sample (Garcia-Rivera et al. (2007) *Brain Res Bull*. 74(6): 429-438).

Total Urine Glycosaminoglycans (GAGs) Assay and Quantitative Urine Heparan Sulfate, Dermatan Sulfate and Chondroitin Sulfate Assay by MS/MS.

A variety of assays exist to measure the level of GAGs in the urine. One exemplary assay is described as follows: Urine samples are collected during the study are analyzed for glycosaminoglycan levels using a Dimethyl Methylene Blue (DMB) Assay. Briefly, urine samples are stained for heparan sulfate by treating the sample with 1,9-dimethylmethylene blue dye resuspended in formic acid at a pH of 3.3, and measured for absorbance at a wave length of 520 nm. The concentration of heparan sulfate was normalized using the total concentration of creatinine protein identified in the urine sample. (see e.g. de Jong et al. (1989) *Clin Chem* 35(7):1472-1479).

Another exemplary assay for measuring total GAG present in a biological sample is as follows: The method involves (a) combining a serine protease (e.g., of the clotting cascade), a labeled substrate for the serine protease, an inhibitor of the serine protease, and a sample suspected of comprising one or more glycosaminoglycans under conditions and for a time suitable for cleavage of the labeled substrate by the serine protease to produce a detectable signal, (b) detecting the detectable signal, and (c) comparing the amount of detectable signal with a standard to determine the concentration of said one or more glycosaminoglycans in said sample, wherein said inhibitor of said serine protease is selected from the group consisting of heparin cofactor II and antithrombin III, and wherein said one or more glycosaminoglycans are selected from the group consisting of dermatan sulfate (DS) and heparin sulfate (HS). (See e.g. U.S. Patent Publication No. 2013/0189718).

Another exemplary assay measures the types of GAGs present and is termed a multiplex assay (Langereis et al. (2015) *PLoS One* 10(9):e0138622). This assay is based on enzymatic digestion the of heparan sulfate (HS), dermatan sulfate (DS) and keratan sulfate (KS) found in the urine, followed by quantification by LC-MS/MS. This assay is a very sensitive assay and can be used to measure the exact types of GAGs in the urine.

Another exemplary assay that can be used to determine the concentration of specific types of GAGs utilizes a RapidFire (RF, Agilent) high-throughput mass spectrometry system. Samples are absorbed to a matrix to concentrate and desalt, and then eluted directly into the MS/MS without chromatographic separation. Each sample is processed in less than ten seconds, yielding much faster throughput than conventional LC-MS/MS based methods (see Tomatsu et al. (2014) *J Anal Bioanal Tech*. March 1; 2014(Suppl 2):006.)

AAV2/6 Clearance in Plasma, Saliva, Urine, Stool and Semen

Detection of AAV in biological samples can be done by several methods known in the art. An exemplary shedding assay is for analysis of AAV2/6-donor and AAV2/6-ZFN vectors in human plasma, semen, saliva, urine, and feces samples, and to evaluate the recovery rate of DNA from the five matrices. Human plasma, semen, saliva, urine, and feces samples from human donors provided the source of matrix DNA for qPCR analysis.

DNA isolation from human Plasma: An aliquot (200 µL) of human plasma sample was thawed, treated with proteinase K in the presence of 2 µg of salmon sperm DNA, prior to DNA isolation using QIAamp DNA Mini kit. The purified plasma DNA was dissolved in 100 µL of elution buffer AE.

DNA isolation from human semen: An aliquot (up to 100 µL) of human semen sample was thawed, treated with proteinase K, and then processed for DNA isolation using QIAamp DNA Mini kit. The purified semen DNA was dissolved in 100 µL of elution buffer AE and the DNA concentration was determined by UV absorption at 260 nm with Nanodrop ND-8000 instrument.

DNA isolation from human saliva: An aliquot (up to 200 µL) of human saliva sample was thawed, treated with proteinase K, and then processed for DNA isolation using QIAamp DNA Mini kit. The purified saliva DNA was dissolved in 100 µL of elution buffer AE and the DNA concentration was determined by UV absorption at 260 nm with Nanodrop ND-8000 instrument.

DNA isolation from human urine: An aliquot (up to 200 µL) of human saliva sample was thawed, treated with proteinase K, and then processed for DNA isolation using QIAamp DNA Mini kit. The purified saliva DNA was dissolved in 100 µL of elution buffer AE and the DNA concentration was determined by UV absorption at 260 nm with Nanodrop ND-8000 instrument.

DNA isolation from human feces: An aliquot (90-110 mg) of human feces sample was partially thawed, homogenized, and treated with proteinase K prior to DNA isolation using QIAamp Fast DNA Stool Mini Kit. The purified feces DNA was dissolved in 200 µL of Buffer ATE and the DNA concentration was determined by UV absorption at 260 nm with Nanodrop ND-8000 instrument.

Each qPCR was performed on a standard 96-well plate in a 7900HT Fast Real Time PCR system. The plate with reaction mix was sealed with optical caps and all droplets spun down by centrifugation at 1500 rpm for 15 min before qPCR.

The reaction for the donor AAV (SB-IDUA, SB-A6P-HNT) amplified and detected a 91 nucleotide amplicon. The reaction for detection of the ZFN DNA (SB-47171: SB-A6P-ZLEFT or SB-71557 and SB-47898: SB-A6P-ZRIGHT or SB-71728) amplified and detected a 96 nucleotide amplicon.

Assay conditions used: Held at 50° C. for 2 minutes. Held at 95° C. for 10 minutes. 40 cycles at 95° C. for 15 seconds, and at 60° C. for 1 minute. Results were compared with a previously prepared standard curve using linearized MPS I or ZFN plasmid DNA.

Gene Modification at the Albumin Locus in Liver Tissue

Detection of gene modification through sequencing or other means is well known in the art. An exemplary assay is to determine the levels of insertions and deletions (indels) at the albumin gene in subject samples using the MiSeq next generation sequencing (NGS) platform. gDNA was isolated from liver tissue using standard procedures and diluted to 20 ng/mL. Samples were subjected to an adaptor PCR followed by a barcode PCR and loaded onto MiSeq cartridge for sequencing. Following conditions are used for PCR reactions:

PCR reaction (Adaptor): 95° C. 3 minutes, [98° C. 20 seconds, 55° C. 15 seconds, 72° C. 15 seconds], repeat bracketed steps 29 times. Final extension at 72° C. for 1 minute.

PCR reaction (Barcode): 95° C. 3 minutes, [98° C. 20 seconds, 60° C. 15 seconds, 72° C. 15 seconds], repeat bracketed steps 9 times. Final extension at 72° C. for 1 minute.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of reducing, delaying and/or eliminating: the need for additional treatment procedures, the onset, progression and/or severity of symptoms in a subject with MPS I, the method comprising administering to the subject a composition comprising first, second and third AAV vectors, the first AAV vector comprising a sequence encoding a left ZFN comprising SEQ ID NO: 23, the second AAV vector comprising a sequence encoding a right ZFN comprising SEQ ID NO: 26 and the third AAV vector comprising a sequence encoding iduronidase (IDUA).

2. The method of claim 1, wherein GAG levels in the subject are reduced, stabilized and/or GAGs are eliminated from the urine of the subject.

3. The method of claim 1, wherein IDUA levels in the subject are stabilized and/or increased.

4. The method of claim 1, wherein first, second and third AAV vectors are administered at a fixed ratio of 1:1:8.

5. The method of claim 1, wherein the additional treatment procedures that are reduced, delayed, and/or eliminated comprise enzyme replacement therapy (ERT); bone marrow transplant; and/or one or more supportive surgical procedures for orthopedic, cardiac and/or upper airway obstruction, wherein cardiac and/or upper air obstruction includes adenotonsillectomy, hernia repair, ventriculoperitoneal shunt, cardiac valve replacement, carpal tunnel release, and/or spinal decompression.

6. The method of claim 1, wherein the symptoms associated with MPS I whose onset, progression or severity are reduced, delayed or eliminated comprise a decline in functional abilities, neurologic deterioration, joint stiffness, becoming wheelchair dependent, progression of disability, the requirement for forced air positive ventilation and/or a shortened life span.

7. The method of claim 1, wherein the first and/or second AAV vectors comprise(s) one or more of the following sequences: sequences encoding small peptides; a WPRE sequence; a nuclear localization signal (NLS)-encoding sequence; a polyA signal; one or more mutations in one or more of the zinc finger protein of the zinc finger nuclease; one or more mutations in a FokI nuclease cleavage domain or cleavage half domain of the zinc finger nuclease; a promoter sequence that drives expression of the ZFN; one or more intron sequences; and/or one or more enhancer sequences.

8. The method of claim 7, wherein the sequence encoding small peptides comprises a FLAG or His tag sequence.

9. The method claim 1, wherein the sequence encoding IDUA comprises a human IDUA-encoding sequence.

10. The method of claim 9, wherein the sequence encoding IDUA comprises the sequence as shown in SEQ ID NO:27 and/or an AAV vector comprising the sequence as shown in SEQ ID NO:28.

11. The method of claim 1, further comprising measuring IDUA activity and/or level in the plasma, liver, CSF or in leukocytes in the subject before and after treatment, wherein additional therapeutic procedures are delayed, reduced or eliminated if IDUA activity is increased after treatment.

12. The method of claim 1, further comprising measuring total GAG levels, GAG comprising dermatan sulfate (DS GAG) levels, and/or GAG comprising heparan sulfate (HS GAG) levels (in the urine of the subject before and after treatment, wherein additional therapeutic procedures are delayed, reduced or eliminated if GAG, DS GAG and/or HS GAG levels are reduced after treatment.

13. The method of claim 1, further comprising measuring forced vital capacity before and after treatment, wherein additional therapeutic procedures are delayed, reduced or eliminated if pulmonary function is increased after treatment.

14. The method of claim 1, further comprising measuring distance walked before and after treatment, wherein additional therapeutic procedures are delayed, reduced or eliminated if distance walked is increased after treatment.

15. The method of claim 1, further comprising measuring joint range of motion (JROM) before and after treatment, wherein additional therapeutic procedures are delayed, reduced or eliminated if JROM is increased after treatment.

16. The method of claim 1, further comprising measuring spleen and/or liver volume before and after spleen and/or liver volume is increased after treatment.

17. The method of claim 1, further comprising measuring one or more neurocognitive abilities before and after treatment, wherein additional therapeutic procedures are delayed, reduced or eliminated if one or more of the neurocognitive abilities is increased after treatment.

18. The method of claim 1, wherein disability progression, organomegaly, hyperactivity, aggressiveness, neurologic deterioration, joint stiffness, skeletal deformities, heart valve thickening, hearing loss, corneal clouding and vision impairment, hernias, and/or upper respiratory infections are suppressed, reduced, delayed or eliminated in the subject after treatment.

19. The method of claim 1, wherein the need for the use of a medical ventilator device in the subject is stabilized, delayed, reduced or prevented after treatment.

20. The method of claim 6, wherein the onset of the subject being wheelchair dependent is delayed, reduced or prevented after treatment.

21. The method of claim 1, wherein the life expectancy of the subject is increased after treatment.

22. The method of claim 5, wherein the additional therapeutic procedure is ERT, wherein ERT is reduced or withdrawn after treatment.

23. The method of claim 5, wherein the additional therapeutic procedure is a bone marrow transplant.

24. The method of claim 1, wherein the composition is administered intravenously.

25. The method of claim 24, wherein a rate of infusion is between 10 to 200 mL/hour.

26. The method of claim 25, wherein the rate of infusion is 100 mL/hour.

27. The method of claim 1, wherein the subject is pre-medicated with a corticosteroid prior to treatment with the composition.

28. The method of claim 27, wherein the corticosteroid is prednisone.

29. The method of claim 28, wherein the subject is treated with one or more corticosteroid prior to treatment; the day of treatment; on day 7 after treatment, weekly after treatment and/or every other week up to 20 weeks after treatment.

30. The method of claim 1, wherein the subject is an adult or child with Hurler/Hurler-Scheie/Scheie syndrome, wherein Hurler/Hurler-Scheie/Scheie syndrome includes early onset MPS I, attenuated MPS I or MPS I between early onset and attenuated.

31. The method of claim 1, wherein a total dose for the subject is determined as follows: determining the subject's weight rounded to two decimal points before treatment; dividing the subject's weight by the vg/mL concentration, thereby determining the total dose to be used.

* * * * *

SEQUENCE LISTING

<160> NUMBER OF SEQ ID NOS: 39

<210> SEQ ID NO 1
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct                                                            130

<210> SEQ ID NO 2
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aggctcagag gcacacagga gtttctgggc tcaccctgcc cccttccaac ccctcagttc      60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtacccggg gatcttgcta ccagtggaac agccactaag    360
gattctgcag tgagagcaga gggccagcta agtggtactc tcccagagac tgtctgactc    420
acgccacccc ctccaccttg gacacaggac gctgtggttt ctgagccagg tacaatgact    480
cctttcggta agtgcagtgg aagctgtaca ctgcccaggc aaagcgtccg ggcagcgtag    540
gcgggcgact cagatcccag ccagtggact tagcccctgt ttgctcctcc gataactggg    600
gtgaccttgg ttaatattca ccagcagcct cccccgttgc ccctctggat ccactgctta    660
aatacggacg aggacagggc cctgtctcct cagcttcagg caccaccact gacctgggac    720
agt                                                                   723

<210> SEQ ID NO 3
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gtaagtatca aggttacaag acaggtttaa ggagaccaat agaaactggg cttgtcgaga      60
cagagaagac tcttgcgttt ctgataggca cctattggtc ttactgacat ccactttgcc    120
tttctctcca cag                                                        133

<210> SEQ ID NO 4
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 4
cccaagaaga agaggaaggt c                                             21

<210> SEQ ID NO 5
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gccgcaatgg cagaacggcc cttccagtgc cgcatctgca tgcgcaactt cagccagtcg    60
ggcaacctgt cccgccacat ccggactcat accggcgaaa aaccattcgc ttgtgacatc   120
tgcggaagaa agtttgcgct gaagcagaac ctctgcatgc ataccaagat tcacaccgga   180
gagaagccgt tcagtgtcg catttgcatg agaaagttcg cctgggccga taaccttcag    240
aatcacacca agatccacac cggggaaaag ccgttccagt gccggatctg catgaggaac   300
ttctcaacgt ccgaaaacct gaccaggcat atccggaccc acactgggga gaagcctttc   360
gcctgcgaca tttgcggtcg gaagttcgcc cggcaatccc acttgtgtct ccacactaag   420
atccacctga ga                                                      432

<210> SEQ ID NO 6
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cagctggtga agagcgagct ggaggagaag aagtccgagc tgcggcacaa gctgaagtac    60
gtgccccacg agtacatcga gctgatcgag atcgccagga acagcaccca ggaccgcatc   120
ctggagatga aggtgatgga gttcttcatg aaggtgtacg gctacagggg aaagcacctg   180
ggcggaagca gaaagcctga cggcgccatc tatacagtgg gcagcccat cgattacggc    240 gtgatcgtgg acacaaaggc ctacagcggc ggctacaatc tgcctatcgg ccaggccgac   300
gagatggaga gatacgtgga ggagaaccag acccgggata agcacctcaa ccccaacgag   360
tggtggaagg tgtaccctag cagcgtgacc gagttcaagt tcctgttcgt gagcggccac   420
ttcaagggca actacaaggc ccagctgacc aggctgaacc acatcaccaa ctgcaatggc   480
gccgtgctga gcgtggagga gctgctgatc ggcggcgaga tgatcaaagc cggcaccctg   540
acactggagg aggtgcggcg caagttcaac aacggcgaga tcaacttcag atcttgataa   600

<210> SEQ ID NO 7
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (224)..(225)
<223> OTHER INFORMATION: This region may or may not be present

<400> SEQUENCE: 7

```
ctgtgccttc tagttgccag ccatctgttg tttgccccct ccccgtgcct tccttgaccc      60
tggaaggtgc cactcccact gtcctttcct aataaaatga ggaaattgca tcgcattgtc     120
tgagtaggtg tcattctatt ctggggggtg gggtggggca ggacagcaag ggggaggatt     180
gggaagacaa tagcaggcat gctggggatg cggtgggctc tatgg                    225
```

<210> SEQ ID NO 8
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
aggaacccct agtgatggag ttggccactc cctctctgcg cgctcgctcg ctcactgagg      60
ccgcccgggc tttgcccggg cggcctcagt gagcgagcga gcgcgcag                  108
```

<210> SEQ ID NO 9
<211> LENGTH: 2529
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct gcggcctagt aggctcgaga gcacacagga gtttctgggc tcaccctgcc     180
cccttccaac ccctcagttc ccatcctcca gcagctgttt gtgtgctgcc tctgaagtcc     240
acactgaaca aacttcagcc tactcatgtc cctaaaatgg gcaaacattg caagcagcaa     300
acagcaaaca cacagccctc cctgcctgct gaccttggag ctggggcaga ggtcagagac     360
ctctctgggc ccatgccacc tccaacatcc actcgacccc ttggaatttc ggtggagagg     420
agcagaggtt gtcctggcgt ggtttaggta gtgtgagagg ggtacccggg gatcttgcta     480
ccagtggaac agccactaag gattctgcag tgagagcaga gggccagcta agtggtactc     540
tcccagagac tgtctgactc acgccacccc ctccaccttg gacacaggac gctgtggttt     600
ctgagccagg tacaatgact cctttcggta agtgcagtgg aagctgtaca ctgcccaggc     660
aaagcgtccg ggcagcgtag gcgggcgact cagatcccag ccagtggact agccccctgt     720
ttgctcctcc gataactggg gtgaccttgg ttaatattca ccagcagcct ccccgttgc      780 ccctctggat ccactgctta aatacgacg aggacagggc cctgtctcct cagcttcagg      840
caccaccact gacctgggac agtcaggtaa gtatcaaggt tacaagacag gtttaaggag     900
accaatagaa actgggcttg tcgagacaga gaagactctt gcgtttctga taggcaccta     960
ttggtcttac tgacatccac tttgcctttc tctccacagg caattcgcca tggcccccaa    1020
gaagaagagg aaggtgggca tccacggggt accggccgca atggcagaac ggcccttcca    1080
gtgccgcatc tgcatgcgca acttcagcca gtcgggcaac ctgtcccgcc acatccggac    1140
tcataccggc gaaaaaccat tcgcttgtga catctgcgga agaaagtttg cgctgaagca    1200
gaacctctgc atgcatacca agattcacac cggagagaag ccgtttcagt gtcgcatttg    1260
catgagaaag ttcgcctggg ccgataacct tcagaatcac accaagatcc acaccgggga    1320
```

```
aaagccgttc cagtgccgga tctgcatgag gaacttctca acgtccggaa acctgaccag     1380
gcatatccgg acccacactg gggagaagcc tttcgcctgc gacatttgcg gtcggaagtt     1440
cgcccggcaa tcccacttgt gtctccacac taagatccac ctgagaggat cccagctggt     1500
gaagagcgag ctggaggaga agaagtccga gctgcggcac aagctgaagt acgtgcccca     1560
cgagtacatc gagctgatcg agatcgccag gaacagcacc caggaccgca tcctggagat     1620
gaaggtgatg gagttcttca tgaaggtgta cggctacagg ggaaagcacc tgggcggaag     1680
cagaaagcct gacggcgcca tctatacagt gggcagcccc atcgattacg gcgtgatcgt     1740
ggacacaaag gcctacagcg gcggctacaa tctgcctatc ggccaggccg acgagatgga     1800
gagatacgtg gaggagaacc agacccggga taagcacctc aaccccaacg agtggtggaa     1860
ggtgtaccct agcagcgtga ccgagttcaa gttcctgttc gtgagcggcc acttcaaggg     1920
caactacaag gcccagctga ccaggctgaa ccacatcacc aactgcaatg cgccgtgct      1980 gagcgtggag gagctgctga tcggcggcga gatgatcaaa gccggcaccc tgacactgga     2040
ggaggtgcgg cgcaagttca caacggcga gatcaacttc agatcttgat aactcgagtc      2100
tagaggatct cgagccgaat tcctgcagcc cggggatca gcctcgactg tgccttctag      2160
ttgccagcca tctgttgttt gcccctcccc cgtgccttcc ttgaccctgg aaggtgccac     2220
tcccactgtc ctttcctaat aaaatgagga aattgcatcg cattgtctga gtaggtgtca     2280
ttctattctg gggggtgggg tggggcagga cagcaagggg gaggattggg aagacaatag     2340
caggcatgct ggggatgcgg tgggctctat ggcttctgag gcggaaagaa ccagctgggg     2400
ctcgagatcc actagggccg caggaacccc tagtgatgga gttggccact ccctctctgc     2460
gcgctcgctc gctcactgag gccgcccggg cttgcccgg gcggcctcag tgagcgagcg     2520
agcgcgcag                                                            2529

<210> SEQ ID NO 10
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gccgcaatgg cagagaggcc ctttcagtgc cggatctgca tgcggaactt ctccacccca       60
caacttctgg accgacatat ccgcacccat accggggaaa agcctttcgc gtgcgacatt      120
tgcggacgga aattcgcgtt gaagcacaat ctcctgaccc acactaagat tcatactggc      180
gaaaagccgt tccagtgccg catctgtatg aggaacttca gcgatcagtc gaacctgaac      240
gcccacattc ggactcatac cggagaaaag ccctttgcct gcgatatctg cggtcgcaag      300
ttcgctagga acttctcact gaccatgcac accaaaatcc acactggaga gcggggattc      360
cagtgtagaa tctgtatgcg caacttctcc ctgcggcacg acctgaccg ccacatcaga       420 acccacaccg gggagaagcc gttcgcctgc gacatctgcg gccggaagtt cgcccaccgg      480
tccaacctga caagcacac gaagattcac ctccgc                                 516

<210> SEQ ID NO 11
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 11

```
cagctggtga agagcgagct ggaggagaag aagtccgagc tgcggcacaa gctgaagtac    60
gtgccccacg agtacatcga gctgatcgag atcgccagga acagcaccca ggaccgcatc   120
ctggagatga aggtgatgga gttcttcatg aaggtgtacg gctacagggg aaagcacctg   180
ggcggaagca gaaagcctga cggcgccatc tatacagtgg gcagccccat cgattacggc   240
gtgatcgtgg acacaaaggc ctacagcggc ggctacaatc tgcctatcgg ccaggccgac   300
gagatgcaga gatacgtgaa ggagaaccag accccggaata agcacatcaa ccccaacgag   360
tggtggaagg tgtaccctag cagcgtgacc gagttcaagt tcctgttcgt gagcggccac   420
ttcaagggca actacaaggc ccagctgacc aggctgaacc gcaaaaccaa ctgcaatggc   480
gccgtgctga gcgtggagga gctgctgatc ggcggcgaga tgatcaaagc cggcaccctg   540
acactggagg aggtgcggcg caagttcaac aacggcgaga tcaacttcctg ataa         594
```

<210> SEQ ID NO 12
<211> LENGTH: 2607
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct gcggcctagt aggctcagag gcacacagga gtttctgggc tcaccctgcc   180
cccttccaac ccctcagttc ccatcctcca gcagctgttt gtgtgctgcc tctgaagtcc   240
acactgaaca aacttcagcc tactcatgtc cctaaaatgg gcaaacattg caagcagcaa   300
acagcaaaca cacagccctc cctgcctgct gaccttggag ctggggcaga ggtcagagac   360
ctctctgggc ccatgccacc tccaacatcc actcgacccc ttggaatttc ggtggagagg   420
agcagaggtt gtcctggcgt ggtttaggta gtgtgagagg ggtacccggg gatcttgcta   480
ccagtggaac agccactaag gattctgcag tgagagcaga gggccagcta agtggtactc   540
tcccagagac tgtctgactc acgccacccc ctccaccttg gacacaggac gctgtggttt   600
ctgagccagg tacaatgact cctttcggta agtgcagtgg aagctgtaca ctgcccaggc   660
aaagcgtccg ggcagcgtag gcgggcgact cagatcccag ccagtggact tagcccctgt   720
ttgctcctcc gataactggg gtgaccttgg ttaatattca ccagcagcct ccccgttgc    780
ccctctggat ccactgctta aatacggacg aggacagggc cctgtctcct cagcttcagg   840
caccaccact gacctgggac agtcaggtaa gtatcaaggt tacaagacag gtttaaggag   900
accaatagaa actgggcttg tcgagacaga gaagactctt gcgtttctga taggcaccta   960
ttggtcttac tgacatccac tttgcctttc tctccacagg caattcgcca tggccccaa   1020
gaagaagagg aaggtgggca tccacggggt accggccgca atggcagaga ggccctttca   1080
gtgccggatc tgcatgcgga acttctccac cccacaactt ctggaccgac atatccgcac   1140
ccataccggg gaaaagcctt tcgcgtgcga catttgcgga cggaaattcg cgttgaagca   1200
caatctcctg acccacacta agattcatac tggcgaaaag ccgttccagt gccgcatctg   1260
tatgaggaac ttcagcgatc agtcgaacct gaacgcccac attcggactc ataccggaga   1320
aaagcccttt gcctgcgata tctgcggtcg caagttcgct aggaacttct cactgaccat   1380
```

```
gcacaccaaa atccacactg gagagcgggg attccagtgt agaatctgta tgcgcaactt    1440
ctccctgcgg cacgacctgg accgccacat cagaacccac accggggaga agccgttcgc    1500
ctgcgacatc tgcggccgga agttcgccca ccggtccaac ctgaacaagc acacgaagat    1560
tcacctccgc ggatcccagc tggtgaagag cgagctggag gagaagaagt ccagctgcg     1620 gcacaagctg aagtacgtgc cccacgagta catcgagctg atcgagatcg ccaggaacag    1680
cacccaggac cgcatcctgg agatgaaggt gatggagttc ttcatgaagg tgtacggcta    1740
caggggaaag cacctgggcg gaagcagaaa gcctgacggc gccatctata cagtgggcag    1800
ccccatcgat tacggcgtga tcgtggacac aaaggcctac agcggcggct acaatctgcc    1860
tatcggccag gccgacgaga tgcagagata cgtgaaggag aaccagaccc ggaataagca    1920
catcaacccc aacgagtggt ggaaggtgta ccctagcagc gtgaccgagt tcaagttcct    1980
gttcgtgagc ggccacttca agggcaacta caaggcccag ctgaccaggc tgaaccgcaa    2040
aaccaactgc aatggcgccg tgctgagcgt ggaggagctg ctgatcggcg gcgagatgat    2100
caaagccggc accctgacac tggaggaggt gcggcgcaag ttcaacaacg gcgagatcaa    2160
cttctgataa ctcgagtcta gaggatctcg agccgaattc ctgcagcccg ggggatcagc    2220
ctcgactgtg ccttctagtt gccagccatc tgttgtttgc ccctcccccg tgccttcctt    2280
gaccctggaa ggtgccactc ccactgtcct ttcctaataa aatgaggaaa ttgcatcgca    2340
ttgtctgagt aggtgtcatt ctattctggg gggtggggtg gggcaggaca gcaaggggga    2400
ggattgggaa gacaatagca ggcatgctgg ggatgcggtg ggctctatgg cttctgaggc    2460
ggaaagaacc agctggggct cgagatccac tagggccgca ggaaccccta gtgatggagt    2520
tggccactcc ctctctgcgc gctcgctcgc tcactgaggc cgcccgggct ttgcccgggc    2580
ggcctcagtg agcgagcgag cgcgcag                                        2607

<210> SEQ ID NO 13
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tttattctat tttcccagta aaataaagtt ttagtaaact ctgcatcttt aaagaattat      60
tttggcattt atttctaaaa tggcatagta ttttgtattt gtgaagtctt acaaggttat     120
cttattaata aaattcaaac atcctaggta aaaaaaaaaa aaggtcagaa ttgtttagtg     180 actgtaatttt tcttttgcgc actaaggaaa gtgcaaagta acttagagtg actgaaactt     240
cacagaatag ggttgaagat tgaattcata actatcccaa                            280

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
actaaagaat tattcttta catttcag                                          28

<210> SEQ ID NO 15
```

```
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
aggctcagag gcacacagga gtttctgggc tcaccctgcc cccttccaac ccctcagttc    60
ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctggggcaga ggtcagagac ctctctgggc ccatgccacc   240
tccaacatcc actcgacccc ttggaatttc ggtggagagg agcagaggtt gtcctggcgt   300
ggtttaggta gtgtgagagg g                                             321

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ctatccattg cactatgctt tatttaaaaa ccacaaaacc tgtgctgttg atctcataaa    60
tagaacttgt atttatattt attttcattt tagtctgtct                        100

<210> SEQ ID NO 17
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gatcttgcta ccagtggaac agccactaag gattctgcag tgagagcaga gggccagcta    60
agtggtactc tcccagagac tgtctgactc acgccacccc ctccaccttg gacacaggac   120
gctgtggttt ctgagccagg tacaatgact cctttcggta agtgcagtgg aagctgtaca   180
ctgcccaggc aaagcgtccg ggcagcgtag gcgggcgact cagatcccag ccagtggact   240
tagcccctgt ttgctcctcc gataactggg gtgaccttgg ttaatattca ccagcagcct   300
cccccgttgc ccctctggat ccactgctta aatacggacg aggacagggc cctgtctcct   360
cagcttcagg caccaccact gacctgggac agt                                393

<210> SEQ ID NO 18
<211> LENGTH: 50
<212> TYPE: DNA
<213> ORGANISM: Xenopus sp.
<220> FEATURE:
<221> NAME/KEY: misc_feature
<222> LOCATION: (1)..(2)
<223> OTHER INFORMATION: This region may or may not be present

<400> SEQUENCE: 18
tgcttgttct ttttgcagaa gctcagaata aacgctcaac tttggcagat               50

<210> SEQ ID NO 19
<211> LENGTH: 66
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 19

```
gactacaaag accatgacgg tgattataaa gatcatgaca tcgattacaa ggatgacgat    60
gacaag                                                               66
```

<210> SEQ ID NO 20
<211> LENGTH: 432
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
gccgctatgg ctgagaggcc cttccagtgt cgaatctgca tgcagaactt cagtcagtcc    60
ggcaacctgg cccgccacat ccgcacccac accggcgaga agccttttgc ctgtgacatt   120
tgtgggagga aatttgccct gaagcagaac ctgtgtatgc ataccaagat acacacgggc   180
gagaagccct tccagtgtcg aatctgcatg cagaagtttg cctggcagtc caacctgcag   240
aaccatacca agatacacac gggcgagaag cccttccagt gtcgaatctg catgcgtaac   300
ttcagtacct ccggcaacct gacccgccac atccgcaccc acaccggcga agcctttt    360 gcctgtgaca tttgtgggag gaaatttgcc cgccgctccc acctgacctc ccataccaag   420
atacacctgc gg                                                       432
```

<210> SEQ ID NO 21
<211> LENGTH: 600
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
cagctggtga agagcgagct ggaggagaag aagtccgagc tgcggcacaa gctgaagtac    60
gtgccccacg agtacatcga gctgatcgag atcgccagga acagcaccca ggaccgcatc   120
ctggagatga aggtgatgga gttcttcatg aaggtgtacg gctacagggg aaagcacctg   180
ggcggaagca gaaagcctga cggcgccatc tatacagtgg gcagccccat cgattacggc   240
gtgatcgtgg acacaaaggc ctacagcggc ggctacaatc tgcctatcgg ccaggccgac   300
gagatggaga gatacgtgga ggagaaccag acccgggata agcacctcaa ccccaacgag   360
tggtggaagg tgtaccctag cagcgtgacc gagttcaagt tcctgttcgt gagcggccac   420
ttcaagggca actacaaggc ccagctgacc aggctgaacc acatcaccaa ctgcgacggc   480
gccgtgctga gcgtggagga gctgctgatc ggcggcgaga tgatcaaagc cggcaccctg   540
acactggagg aggtgcggcg caagttcaac aacggcgaga tcaacttcag atcttgataa   600
```

<210> SEQ ID NO 22
<211> LENGTH: 592
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
aatcaacctc tggattacaa aatttgtgaa agattgactg atattcttaa ctatgttgct    60
ccttttacgc tgtgtggata tgctgcttta atgcctctgt atcatgctat tgcttcccgt   120
acggctttcg ttttctcctc cttgtataaa tcctggttgc tgtctcttta tgaggagttg   180
tggcccgttg tccgtcaacg tggcgtggtg tgctctgtgt ttgctgacgc aaccccccact  240 ggctggggca ttgccaccac ctgtcaactc ctttctggga ctttcgcttt ccccctcccg   300
atcgccacgg cagaactcat cgccgcctgc cttcccgct gctggacagg gctaggttg    360 ctgggcactg ataattccgt ggtgttgtcg gggaaatcat cgtcctttcc ttggctgctc   420
gcctgtgttg ccaactggat cctgcgcggg acgtccttct gctacgtccc ttcggctctc   480
aatccagcgg acctcccttc ccgaggcctt ctgccggttc tgcggcctct cccgcgtctt   540
cgctttcggc ctccgacgag tcggatctcc ctttgggccg cctccccgcc tg           592
```

<210> SEQ ID NO 23
<211> LENGTH: 3195
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 23

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct gcggcctaag cttgagctct tcgaaaggct cagaggcaca caggagtttc   180
tgggctcacc ctgccccctt ccaacccctc agttcccatc ctccagcagc tgtttgtgtg   240
ctgcctctga gtccacact gaacaaactt cagcctactc atgtccctaa aatgggcaaa    300
cattgcaagc agcaaacagc aaacacacag ccctccctgc ctgctgacct tggagctggg   360
gcagaggtca gagacctctc tgggcccatg ccacctccaa catccactcg acccctttgga  420 atttcggtgg agaggagcag aggttgtcct ggcgtggttt aggtagtgtg agaggggtcc   480
cggggatctt gctaccagtg aacagccac taaggattct gcagtgagag cagagggcca    540
gctaagtggt actctcccag agactgtctg actcacgcca cccctccac cttggacaca    600 ggacgctgtg gttctgagc caggtacaat gactcctttc ggtaagtgca gtggaagctg    660
tacactgccc aggcaaagcg tccgggcagc gtaggcgggc gactcagatc ccagccagtg   720
gacttagccc ctgtttgctc ctccgataac tgggtgacc ttggttaata ttcaccagca    780
gcctcccccg ttgcccctct ggatccactg cttaaatacg gacgaggaca gggccctgtc   840
tcctcagctt caggcaccac cactgacctg ggacagtcct aggtgcttgt tcttttttgca  900 gaagctcaga ataaacgctc aactttggca gatactagtc aggtaagtat caaggttaca    960
agacaggttt aaggagacca atagaaactg ggcttgtcga gacagagaag actcttgcgt   1020
ttctgatagg cacctattgg tcttactgac atccactttg cctttctctc cacaggaccg   1080
gtgccatgga ctacaaagac catgacggtg attataaaga tcatgacatc gattacaagg   1140
atgacgatga caagatggcc cccaagaaga gaggaaggt cggcattcat ggggtacccg    1200
ccgctatggc tgagaggccc ttccagtgtc gaatctgcat gcagaacttc agtcagtccg   1260
gcaacctggc ccgccacatc cgcacccaca ccggcgagaa gccttttgcc tgtgacattt   1320
gtgggaggaa atttgccctg aagcagaacc tgtgtatgca taccaagata cacacggcg   1380 agaagccctt ccagtgtcga atctgcatgc agaagtttgc ctggcagtcc aacctgcaga   1440
```

```
accataccaa gatacacacg ggcgagaagc ccttccagtg tcgaatctgc atgcgtaact    1500
tcagtacctc cggcaacctg acccgccaca tccgcaccca caccggcgag aagccttttg    1560
cctgtgacat tgtgggagg aaatttgccc gccgctccca cctgacctcc cataccaaga    1620
tacacctgcg gggatcccag ctggtgaaga gcgagctgga ggagaagaag tccgagctgc    1680
ggcacaagct gaagtacgtg ccccacgagt acatcgagct gatcgagatc gccaggaaca    1740
gcacccagga ccgcatcctg gagatgaagg tgatggagtt cttcatgaag gtgtacggct    1800 acagggaaa gcacctgggc ggaagcagaa agcctgacgg cgccatctat acagtgggca    1860
gccccatcga ttacggcgtg atcgtggaca caaaggccta cagcggcggc tacaatctgc    1920
ctatcggcca ggccgacgag atggagagat acgtggagga gaaccagacc cgggataagc    1980
acctcaaccc caacgagtgg tggaaggtgt accctagcag cgtgaccgag ttcaagttcc    2040
tgttcgtgag cggccacttc aagggcaact acaaggccca gctgaccagg ctgaaccaca    2100
tcaccaactg cgacggcgcc gtgctgagcg tggaggagct gctgatcggc ggcgagatga    2160
tcaaagccgg caccctgaca ctggaggagg tgcggcgcaa gttcaacaac ggcgagatca    2220
acttcagatc ttgataactc gagtctagaa atcaacctct ggattacaaa atttgtgaaa    2280
gattgactga tattcttaac tatgttgctc cttttacgct gtgtggatat gctgctttaa    2340
tgcctctgta tcatgctatt gcttcccgta cggctttcgt tttctcctcc ttgtataaat    2400
cctggttgct gtctctttat gaggagttgt ggcccgttgt ccgtcaacgt ggcgtggtgt    2460
gctctgtgtt tgctgacgca accccactg gctggggcat gccaccacc tgtcaactcc    2520 tttctgggac tttcgctttc cccctcccga tcgccacggc agaactcatc gccgcctgcc    2580
ttgcccgctg ctggacaggg gctaggttgc tgggcactga taattccgtg gtgttgtcgg    2640
ggaaatcatc gtccttttcct tggctgctcg cctgtgttgc caactggatc ctgcgcggga    2700
cgtccttctg ctacgtccct tcggctctca atccagcgga cctcccttcc cgaggccttc    2760
tgccggttct gcggcctctc ccgcgtcttc gctttcggcc tccgacgagt cggatctccc    2820
tttgggccgc ctccccgcct ggctagcctg tgccttctag ttgccagcca tctgttgttt    2880
gcccctcccc cgtgccttcc ttgaccctgg aaggtgccac tcccactgtc ctttcctaat    2940
aaaatgagga aattgcatcg cattgtctga gtaggtgtca ttctattctg ggggtgggg    3000 tggggcagga cagcaagggg gaggattggg aagacaatag caggcatgct ggggatgcgg    3060
tgggctctat gcggccgcgt cgagcgcagg aaccccctagt gatggagttg gccactccct    3120
ctctgcgcgc tcgctcgctc actgaggccg cccgggcttt gcccgggcgg cctcagtgag    3180
cgagcgagcg cgcag                                                    3195
```

<210> SEQ ID NO 24
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gccgctatgg ctgagaggcc cttccagtgt cgaatctgca tgcgtaactt cagtcagtcc      60
tccgacctgt cccgccacat ccgcacccac accggcgaga agccttttgc ctgtgacatt     120
tgtgggagga aatttgccct gaagcacaac ctgctgaccc ataccaagat acacacgggc     180
gagaagccct ccagtgtcg aatctgcatg cagaacttca gtgaccagtc caacctgcgc     240
```

-continued

```
gcccacatcc gcacccacac cggcgagaag ccttttgcct gtgacatttg tgggaggaaa      300
tttgcccgca acttctccct gaccatgcat accaagatac acaccggaga gcgcggcttc      360
cagtgtcgaa tctgcatgcg taacttcagt ctgcgccacg acctggagcg ccacatccgc      420
acccacaccg gcgagaagcc ttttgcctgt gacatttgtg ggaggaaatt tgcccaccgc      480
tccaacctga acaagcatac caagatacac ctgcgg                                516
```

<210> SEQ ID NO 25
<211> LENGTH: 594
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 25

```
cagctggtga agagcgagct ggaggagaag aagtccgagc tgcggcacaa gctgaagtac      60
gtgccccacg agtacatcga gctgatcgag atcgccagga acagcaccca ggaccgcatc      120
ctggagatga aggtgatgga gttcttcatg aaggtgtacg gctacagggg aaagcacctg      180
ggcggaagca gaaagcctga cggcgccatc tatacagtgg gcagcccat cgattacggc       240 gtgatcgtgg acacaaaggc ctacagcggc ggctacaatc tgagcatcgg ccaggccgac      300
gagatgcaga gatacgtgaa ggagaaccag acccggaata gcacatcaa ccccaacgag       360 tggtggaagg tgtaccctag cagcgtgacc gagttcaagt tcctgttcgt gagcggccac      420
ttcaagggca actacaaggc ccagctgacc aggctgaacc gcaaaaccaa ctgcaatggc      480
gccgtgctga gcgtggagga gctgctgatc ggcggcgaga tgatcaaagc cggcaccctg      540
acactggagg aggtgcggcg caagttcaac aacggcgaga tcaacttctg ataa            594
```

<210> SEQ ID NO 26
<211> LENGTH: 3273
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 26

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact      120
aggggttcct gcggcctaag cttgagctct tcgaaaggct cagaggcaca caggagtttc      180
tgggctcacc ctgccccctt ccaaccctc agttcccatc ctccagcagc tgtttgtgtg      240
ctgcctctga agtccacact gaacaaactt cagcctactc atgtccctaa aatgggcaaa      300
cattgcaagc agcaaacagc aaacacacag ccctccctgc ctgctgacct tggagctggg      360
gcagaggtca gagacctctc tgggcccatg ccacctccaa catccactcg acccttggga      420
atttcggtgg agaggagcag aggttgtcct ggcgtggttt aggtagtgtg agagggtcc       480 cggggatctt gctaccagtg aacagccac taaggattct gcagtgagag cagagggcca       540
gctaagtggt actctcccag agactgtctg actcacgcca ccccctccac cttgacaca       600 ggacgctgtg gtttctgagc caggtacaat gactcctttc ggtaagtgca gtggaagctg      660
tacactgccc aggcaaagcg tccgggcagc gtaggcgggc gactcagatc ccagccagtg      720
gacttagccc ctgtttgctc ctccgataac tggggtgacc ttggttaata ttcaccagca      780
```

```
gcctcccccg ttgcccctct ggatccactg cttaaatacg gacgaggaca gggccctgtc    840
tcctcagctt caggcaccac cactgacctg ggacagtcct aggtgcttgt tcttttttgca   900 gaagctcaga ataaacgctc aactttggca gatactagtc aggtaagtat caaggttaca    960
agacaggttt aaggagacca atagaaactg ggcttgtcga gacagagaag actcttgcgt   1020
ttctgatagg cacctattgg tcttactgac atccactttg cctttctctc cacaggaccg   1080
gtgccatgga ctacaaagac catgacggtg attataaaga tcatgacatc gattacaagg   1140
atgacgatga caagatggcc cccaagaaga agaggaaggt cggcattcat ggggtacccg   1200
ccgctatggc tgagaggccc ttccagtgtc gaatctgcat gcgtaacttc agtcagtcct   1260
ccgacctgtc ccgccacatc cgcacccaca ccggcgagaa gccttttgcc tgtgacattt   1320
gtgggaggaa atttgccctg aagcacaacc tgctgaccca taccaagata cacacgggcg   1380
agaagccctt ccagtgtcga atctgcatgc agaacttcag tgaccagtcc aacctgcgcg   1440
cccacatccg cacccacacc ggcgagaagc cttttgcctg tgacatttgt gggaggaaat   1500
ttgcccgcaa cttctccctg accatgcata ccaagataca caccggagag cgcggcttcc   1560
agtgtcgaat ctgcatgcgt aacttcagtc tgcgccacga cctggagcgc cacatccgca   1620
cccacaccgg cgagaagcct tttgcctgtg acatttgtgg gaggaaattt gcccaccgct   1680
ccaacctgaa caagcatacc aagatacacc tgcgggatc ccagctggtg aagagcgagc   1740
tggaggagaa gaagtccgag ctgcggcaca gctgaagta cgtgccccac gagtacatcg   1800
agctgatcga gatcgccagg aacagcaccc aggaccgcat cctggagatg aaggtgatgg   1860
agttcttcat gaaggtgtac ggctacaggg aaaagcacct gggcggaagc agaaagcctg   1920
acggcgccat ctatacagtg ggcagcccca tcgattacgg cgtgatcgtg gacacaaagg   1980
cctacagcgg cggctacaat ctgagcatcg gccaggccga cgagatgcag agatacgtga   2040
aggagaacca gacccggaat aagcacatca accccaacga gtggtggaag gtgtacccta   2100
gcagcgtgac cgagttcaag ttcctgttcg tgagcggcca cttcaagggc aactacaagg   2160
cccagctgac caggctgaac cgcaaaacca actgcaatgg cgccgtgctg agcgtggagg   2220
agctgctgat cggcggcgag atgatcaaag ccggcaccct gacactggag gaggtgcggc   2280
gcaagttcaa caacggcgag atcaacttct gataactcga gtctagaaat caacctctgg   2340
attacaaaat ttgtgaaaga ttgactgata ttcttaacta tgttgctcct tttacgctat   2400
gtggatatgc tgctttaatg cctctgtatc atgctattgc ttcccgtacg ctttcgtttt   2460
tctcctcctt gtataaatcc tggttgctgt ctctttatga ggagttgtgg cccgttgtcc   2520
gtcaacgtgg cgtggtgtgc tctgtgtttg ctgacgcaac ccccactggc tggggcattg   2580
ccaccacctg tcaactcctt tctgggactt tcgctttccc cctcccgatc gccacggcag   2640
aactcatcgc cgcctgcctt gcccgctgct ggacaggggc taggttgctg ggcactgata   2700
attccgtggt gttgtcgggg aaatcatcgt cctttccttg gctgctcgcc tgtgttgcca   2760
actggatcct gcgcgggacg tccttctgct acgtcccttc ggctctcaat ccagcggacc   2820
tcccttcccg aggccttctg ccggttctgc ggcctctccc gcgtcttcgc tttcggcctc   2880
cgacgagtcg gatctccctt tgggccgcct ccccgcctgg ctagcctgtg ccttctagtt   2940
gccagccatc tgttgtttgc ccctcccccg tgccttcctt gaccctggaa ggtgccactc   3000
ccactgtcct ttcctaataa aatgaggaaa ttgcatcgca ttgtctgagt aggtgtcatt   3060
ctattctggg gggtggggtg gggcaggaca gcaaggggga ggattgggaa gacaatagca   3120
ggcatgctgg ggatgcggtg ggctctatgc ggccgcgtcg agcgcaggaa cccctagtga   3180
```

```
tggagttggc cactccctct ctgcgcgctc gctcgctcac tgaggccgcc cgggctttgc    3240
ccgggcggcc tcagtgagcg agcgagcgcg cag                                  3273

<210> SEQ ID NO 27
<211> LENGTH: 1872
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cacttggtcc acgtcgacgc tgccagagcc ctgtggccgc ttcgaagatt ttggaggtca      60
acgggtttct gtcctcccct tccccactcg caagcagatc agtatgtact gtcatgggat     120
caacagctta acctcgccta tgtcggagca gtgcctcacc gcgggatcaa gcaagtaagg     180
acacattggc tccttgaact cgtcaccacg agaggatcga cgggaagggg gctttcgtac     240
aacttcactc atctcgatgg ctatttggat ctcctccgcg agaatcagtt gttgccaggc     300
ttcgaattga tgggatcggc gagcgggcac tttacagact cgaggacaa gcagcaagtg      360 tttgagtgga aggacctcgt gtcgtcgctc gcgaggagat acattggtcg ctacggtttg     420
gcgcatgtgt caaagtggaa cttcgaaacg tggaacgagc ccgatcatca cgattttgac     480
aacgtgtcaa tgaccatgca gggtttcctt aactattacg acgcctgttc cgagggattg     540
agggcagcat caccggcgct tcggctggga gggcctggtg atagctttca tacaccacct     600
cgatcgccac tttcgtgggg gctgctgcgc cattgtcacg atggtacgaa cttcttcacc     660
ggggaagcgg gggtacggct tgattacatc agcctccacc gaaagggagc gcggtcaagc     720
atctcgattc tggagcagga gaaggtagtc gctcagcaga tccggcaact cttteccaag     780 ttcgcagaca cacctatcta caatgatgag gcagaccccac ttgtgggatg gtcccttccg     840
cagccatggc gcgcagatgt gacttatgcc gcgatggtag tgaaagtcat cgcccagcac     900
cagaatctgc ttcttgcgaa tacgaccagc gcgtttcctt acgcgctttt gtcgaacgat     960 aatgcctttcc tgtcatatca ccccccatccg tttgcgcaga ggactcttac ggcgcgattc    1020
caagtgaata acaccagacc gccgcacgtg cagctgttgc gaaaacccgt gttgactgcg    1080
atggggcttc tggcgttgct tgatgaggaa caactctggg ctgaagtgtc ccaggcgggg    1140
acagtacttg atagcaatca tacagtaggc gtgttggcgt cggcgcaccg accgcaggga    1200
cccgcggatg cttggagggc agcggtcctg atctacgcct cggacgatac tagggcacat    1260
cccaacagat cggtcgctgt caccccttcgc ctcagagggg tcccgcctgg tcccggcttg    1320
gtatacgtca ctagatatct cgacaatgga ctgtgcagcc ccgacggaga gtggcggagg    1380
ctgggacggc cggtgttttcc gacagccgag cagtttagac ggatgagggc cgctgaggac    1440
cccgtggcag cggcaccgag gcccctcccg gcaggaggtc gcctcactct tcgaccggca    1500
ctgcggctgc cgtcccttct gctcgtacac gtctgcgcgc gacccgaaaa gccgcctgga    1560
caggtaacca ggctcagggc gctccccttg acgcaggggc agttggtact tgtctggtcg    1620
gacgaacacg tggggtccaa atgcttgtgg acgtatgaaa ttcagttttc caagacggg     1680 aaagcgtaca ctccggtgtc gcgcaaaccc tccacgttca acctcttcgt cttttcccca    1740
gacacgggag ccgtatcagg gtcgtaccga gtcagagccc tcgattattg ggcgaggcct    1800
gggccgttct cggaccctgt accatacttg gaagtgccgg tgcccagggg accgccctcg    1860
cctggtaatc ct                                                        1872
```

<210> SEQ ID NO 28
<211> LENGTH: 3055
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 28

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggcctaag | cttgagcgga | gttccaattg | tactgtacag | aaccatggtc | 180 |
| acatgtttaa | cgctagcgtg | ccgacctggt | aaactgatca | gtgggtgcac | ttaggactgc | 240 |
| gtcttacgct | aatcacatgc | gtgcggccgc | tttattctat | tttcccagta | aaataaagtt | 300 |
| ttagtaaact | ctgcatcttt | aaagaattat | tttggcattt | atttctaaaa | tggcatagta | 360 |
| ttttgtattt | gtgaagtctt | acaaggttat | cttattaata | aaattcaaac | atcctaggta | 420 |
| aaaaaaaaaa | aaggtcagaa | ttgtttagtg | actgtaattt | tcttttgcgc | actaaggaaa | 480 |
| gtgcaaagta | acttagagtg | actgaaactt | cacagaatag | ggttgaagat | tgaattcata | 540 |
| actatcccaa | ggtaccacta | aagaattatt | cttttacatt | tcagcgcact | tggtccacgt | 600 |
| cgacgctgcc | agagccctgt | ggccgcttcg | aagattttgg | aggtcaacgg | gtttctgtcc | 660 |
| tccccttccc | cactcgcaag | cagatcagta | tgtactgtca | tgggatcaac | agcttaacct | 720 |
| cgcctatgtc | ggagcagtgc | ctcaccgcgg | gatcaagcaa | gtaaggacac | attggctcct | 780 |
| tgaactcgtc | accacgagag | gatcgacggg | aaggggctt | tcgtacaact | tcactcatct | 840 |
| cgatggctat | ttggatctcc | tccgcgagaa | tcagttgttg | ccaggcttcg | aattgatggg | 900 |
| atcggcgagc | gggcacttta | cagacttcga | ggacaagcag | caagtgtttg | agtggaagga | 960 |
| cctcgtgtcg | tcgctcgcga | ggagatacat | tggtcgctac | ggtttggcgc | atgtgtcaaa | 1020 |
| gtggaacttc | gaaacgtgga | acgagcccga | tcatcacgat | tttgacaacg | tgtcaatgac | 1080 |
| catgcagggt | ttccttaact | attacgacgc | ctgttccgag | ggattgaggg | cagcatcacc | 1140 |
| ggcgcttcgg | ctgggagggc | ctggtgatag | cttttcataca | ccacctcgat | cgccactttc | 1200 |
| gtgggggctg | ctgcgccatt | gtcacgatgg | tacgaacttc | ttcaccgggg | aagcgggggt | 1260 |
| acggcttgat | tacatcagcc | tccaccgaaa | gggagcgcgg | tcaagcatct | cgattctgga | 1320 |
| gcaggagaag | gtagtcgctc | agcagatccg | gcaactcttt | cccaagttcg | cagacacacc | 1380 |
| tatctacaat | gatgaggcag | acccacttgt | gggatggtcc | cttccgcagc | catggcgcgc | 1440 |
| agatgtgact | tatgccgcga | tggtagtgaa | agtcatcgcc | cagcaccaga | atctgcttct | 1500 |
| tgcgaatacg | accagcgcgt | ttccttacgc | gcttttgtcg | aacgataatg | ccttcctgtc | 1560 |
| atatcacccc | catccgtttg | cgcagaggac | tcttacggcg | cgattccaag | tgaataacac | 1620 |
| cagaccgccg | cacgtgcagc | tgttgcgaaa | acccgtgttg | actgcgatgg | ggcttctggc | 1680 |
| gttgcttgat | gaggaacaac | tctgggctga | agtgtcccag | gcggggacag | tacttgatag | 1740 |
| caatcataca | gtaggcgtgt | tggcgtcggc | gcaccgaccg | cagggacccg | cggatgcttg | 1800 |
| gagggcagcg | gtcctgatct | acgcctcgga | cgatactagg | gcacatccca | acagatcggt | 1860 |
| cgctgtcacc | cttcgcctca | gaggggtccc | gcctggtccc | ggcttggtat | acgtcactag | 1920 |
| atatctcgac | aatggactgt | gcagcccga | cggagtgg | cggaggctgg | gacggccggt | 1980 |
| gtttccgaca | gccgagcagt | ttagacggat | gagggccgct | gaggaccccg | tggcagcggc | 2040 |

-continued

```
accgaggccc ctcccggcag gaggtcgcct cactcttcga ccggcactgc ggctgccgtc    2100
ccttctgctc gtacacgtct gcgcgcgacc cgaaaagccg cctggacagg taaccaggct    2160
cagggcgctc cccttgacgc aggggcagtt ggtacttgtc tggtcggacg aacacgtggg    2220
gtccaaatgc ttgtggacgt atgaaattca gttttcccaa gacggaaag cgtacactcc    2280 ggtgtcgcgc aaaccctcca cgttcaacct cttcgtcttt tccccagaca cgggagccgt    2340
atcagggtcg taccgagtca gagccctcga ttattgggcg aggcctgggc cgttctcgga    2400
ccctgtacca tacttggaag tgccggtgcc caggggaccg ccctcgcctg gtaatccttg    2460
ataaagatct ctgtgccttc tagttgccag ccatctgttg tttgcccctc ccccgtgcct    2520
tccttgaccc tggaaggtgc cactcccact gtcctttcct aataaaatga ggaaattgca    2580
tcgcattgtc tgagtaggtg tcattctatt ctgggggtg gggtggggca ggacagcaag    2640
ggggaggatt gggaagacaa tagcaggcat gctggggatg cggtgggctc tatggaccgg    2700
tctatccatt gcactatgct ttatttaaaa accacaaaac ctgtgctgtt gatctcataa    2760
atagaacttg tatttatatt tattttcatt ttagtctgtc tggatccaca aattaatcga    2820
acctgcagct gatatcgacg cttaagtagg gcttagcaaa cgcgtctcca acgtttcgcc    2880
gttaacaccc cacatagtga gtggtcttag tagtccgggt gtttaaactg aaagataact    2940
cgagcgcagg aaccctagt gatggagttg gccactccct ctctgcgcgc tcgtcgctc    3000 actgaggccg cccgggcttt gcccgggcgg cctcagtgag cgagcgagcg cgcag          3055
```

<210> SEQ ID NO 29
<211> LENGTH: 1623
<212> TYPE: DNA
<213> ORGANISM: Chlamydomonas reinhardtii

<400> SEQUENCE: 29

```
gatccttgat caggacccct tgacagttca ggtgggcagt ttatttgggg cgaatgcctc      60
ctaaaaggta acggaggcgt gcaaaggttc cctcagtctg gacggaaatc agacattgag     120
tgtaaaggca aagggagct tgactgcaag acctacaagt cgagcagggg cgaaagaggc     180
cttagtgatc cgacggtgcc gcgtggaagg gccgtcgctc aacggataaa agttactccc     240
gggataacag gctgatcttc cccaagagtt cacatcgacg ggaaggtttg gcacctcgat     300
gtcggctcat cacatcctcg gtctgtagta ggtccgaagg gttgggctgt cgcccatta     360 aagtggtacg tgagctgggt tcaaaacgta ataacactg cgtgtgcttg cagtaatgta     420
agcaaagtat cggcttatat cggtgaaacc ttcctattgt tttaagtaca aactgtcgca     480
taaaccacat tcgtgggcaa tagatggcaa cgccgaggga agaccatttc ttttttggttt    540 aataattcaa taaattaaat aaaacatctt atgaatacaa aatataataa agagttctta     600
ctctacttag cagggtttgt agacggtgac ggtagcataa tcgctcaaat taagcctaat     660
cagtcttata aatttaagca tcagctatca ctcgcgttcc aagtcacgca aaagacacag     720
agacgttggt ttttagacaa attagtggat gaaattgggg ttggttatgt aagagatagg    780
ggtagcgttt cggattatat tctaagcgaa atcaagcctt tgcataattt tttaacacaa     840
ctacaacctt ttctaaaact aaaacaaaaa caagcaaatt tagttttaaa aattatttgg    900
cggcttccgt cagcaaaaga atccccggac aaattcttag aagtttgtac atgggtggat    960
caaattgcag ctctgaatga ttcgaagacg cgtaaaacaa cttctgaaac cgttcgtgct    1020
gtgctagaca gtttaagtga aaaaagaaa tcgtccccgt agagacttta taaatttagc    1080
```

-continued

```
caatctctaa aagaatgttt acatacaatt tatttattgt tgctcgattt ataggatatt    1140
ttctcgagag tgggaaagta taatacgccg actcctgcca ttaacagtag caggatgaag    1200
acatagtcca tgcctttacg aaagtaaagg ggttagtttt aaagaccgca agttttattc    1260
ggctttaaaa tttcatgcgt gagacagttt ggtccatatc cggtgtaggc gttagagcat    1320
tgagagtagc ctttcatagt acgagaggac ctgaaaggac atgccaattg tgtaccagtt    1380
ctcattccaa tgggaaacgc tgggtagcta cgcatggata gataactgct gaaagcatct    1440
aagtaggaag ctaaactcaa gatgagtgct ctctaaggcc gcggctagac aagccgttat    1500
ataggtatca ggtgtacagt cagcaatggc tttagccgag atatactaaa ggccgtttga    1560
ttttgacctt tataatataa ttacataacc ccttgcgggt aactatcgtt tatgagctaa    1620
gct                                                                 1623
```

```
<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Tyr Lys Asp Asp Asp Lys
1               5

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 32
<211> LENGTH: 7
<212> TYPE: PRT
<213> ORGANISM: Simian virus 40

<400> SEQUENCE: 32

Pro Lys Lys Lys Arg Lys Val
1               5

<210> SEQ ID NO 33
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 33

Pro Ala Ala Lys Arg Val Lys Leu Asp
1               5

<210> SEQ ID NO 34
<211> LENGTH: 10
```

```
<212> TYPE: PRT
<213> ORGANISM: Hepatitis delta virus

<400> SEQUENCE: 34

Glu Gly Ala Pro Pro Ala Lys Arg Ala Arg
1               5                   10

<210> SEQ ID NO 35
<211> LENGTH: 8
<212> TYPE: PRT
<213> ORGANISM: Unknown
<220> FEATURE:
<223> OTHER INFORMATION: Description of Unknown:
      polyoma T protein

<400> SEQUENCE: 35

Val Ser Arg Lys Arg Pro Arg Pro
1               5

<210> SEQ ID NO 36
<211> LENGTH: 18
<212> TYPE: PRT
<213> ORGANISM: Unknown
<220> FEATURE:
<223> OTHER INFORMATION: Description of Unknown:
      NLS sequence

<400> SEQUENCE: 36

Lys Arg Pro Ala Ala Thr Lys Lys Ala Gly Gln Ala Lys Lys Lys Lys
1               5                   10                  15

Leu Asp

<210> SEQ ID NO 37
<211> LENGTH: 38
<212> TYPE: PRT
<213> ORGANISM: Unknown
<220> FEATURE:
<223> OTHER INFORMATION: Description of Unknown:
      NLS sequence

<400> SEQUENCE: 37

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 38
<211> LENGTH: 17
<212> TYPE: PRT
<213> ORGANISM: Unknown
<220> FEATURE:
<223> OTHER INFORMATION: Description of Unknown:
      NLS sequence

<400> SEQUENCE: 38

Pro Lys Thr Arg Arg Arg Pro Arg Arg Ser Gln Arg Lys Arg Pro Pro
1               5                   10                  15
```

```
Thr

<210> SEQ ID NO 39
<211> LENGTH: 9
<212> TYPE: PRT
<213> ORGANISM: Unknown
<220> FEATURE:
<223> OTHER INFORMATION: Description of Unknown:
      "LAGLIDADG" family motif

<400> SEQUENCE: 39

Leu Ala Gly Leu Ile Asp Ala Asp Gly
1               5
```